(12) United States Patent
Boyce et al.

(10) Patent No.: US 7,858,641 B2
(45) Date of Patent: Dec. 28, 2010

(54) SUBSTITUTED DIHYDROISOQUINOLINONE COMPOUNDS

(75) Inventors: Rustum S. Boyce, San Francisco, CA (US); Natalia Aurrecoechea, Oakland, CA (US); Daniel Chu, Santa Clara, CA (US); Aaron Smith, Union City, CA (US); Bryan Chang, Cambridge, MA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 679 days.

(21) Appl. No.: 11/248,040

(22) Filed: Oct. 11, 2005

(65) Prior Publication Data

US 2006/0030573 A1 Feb. 9, 2006

(51) Int. Cl.
*A61K 31/47* (2006.01)
(52) U.S. Cl. .................. 514/314; 544/402; 546/176
(58) Field of Classification Search ................ 514/314; 544/402; 546/176
See application file for complete search history.

(56) References Cited

U.S. PATENT DOCUMENTS

| | | | |
|---|---|---|---|
| 3,177,218 A | 4/1965 | Brown | |
| 4,128,643 A | 12/1978 | Merkel et al. | |
| 4,211,867 A | 7/1980 | Rasmussen | |
| 4,287,341 A | 9/1981 | Hess et al. | |
| 4,496,571 A | 1/1985 | Yellin et al. | |
| 4,626,537 A | 12/1986 | Dave et al. | |
| 4,732,916 A | 3/1988 | Satoh et al. | |
| 4,748,165 A | 5/1988 | Jones et al. | |
| 4,874,864 A | 10/1989 | Schnur et al. | |
| 4,948,891 A | 8/1990 | Schnur et al. | |
| 4,948,901 A | 8/1990 | Schnur et al. | |
| 5,086,057 A | 2/1992 | Sasagawa | |
| 5,124,328 A | 6/1992 | Fisher et al. | |
| 5,352,704 A | 10/1994 | Okuyama et al. | |
| 5,362,902 A | 11/1994 | Barnish et al. | |
| 5,547,966 A | 8/1996 | Atwal et al. | |
| 5,637,439 A | 6/1997 | Kaneko et al. | |
| 5,731,408 A | 3/1998 | Hadley et al. | |
| 5,750,573 A | 5/1998 | Bianchi et al. | |
| 5,885,985 A | 3/1999 | Macdonald et al. | |
| 5,889,025 A | 3/1999 | Lohray et al. | |
| 5,952,381 A | 9/1999 | Chen et al. | |
| 5,962,530 A | 10/1999 | Engel et al. | |
| 6,020,349 A | 2/2000 | Ankersen et al. | |
| 6,030,985 A | 2/2000 | Gentile et al. | |
| 6,054,556 A | 4/2000 | Huby et al. | |
| 6,060,589 A | 5/2000 | Stark et al. | |
| 6,127,343 A | 10/2000 | Andersen et al. | |
| 6,180,603 B1 | 1/2001 | Frey, II | |
| 6,225,331 B1 | 5/2001 | Cupps et al. | |
| 6,313,093 B1 | 11/2001 | Frey, II | |
| 6,391,878 B2 | 5/2002 | Cupps et al. | |
| 6,716,840 B2 | 4/2004 | Chu et al. | |
| 6,995,269 B2 | 2/2006 | Renhowe et al. | |
| 7,034,033 B2 | 4/2006 | Boyce et al. | |
| 7,368,453 B2 | 5/2008 | Boyce et al. | |
| 2002/0137939 A1 | 9/2002 | Renhowe et al. | |
| 2002/0193595 A1 | 12/2002 | Chu et al. | |
| 2003/0195187 A1 | 10/2003 | Boyce et al. | |
| 2003/0207814 A1 | 11/2003 | Boyce et al. | |
| 2003/0229025 A1 | 12/2003 | Xiao et al. | |
| 2005/0059662 A1 | 3/2005 | Boyce et al. | |
| 2006/0235019 A1 | 10/2006 | Boyce et al. | |

FOREIGN PATENT DOCUMENTS

| | | |
|---|---|---|
| DE | 31 08 322 | 12/1981 |
| EP | 0343894 | 11/1989 |
| WO | WO 96/24580 | 8/1996 |
| WO | WO 97/19911 | 6/1997 |
| WO | WO 97/41119 | 11/1997 |
| WO | WO 98/07420 | 2/1998 |
| WO | WO 99/64002 | 12/1999 |
| WO | WO 00/03973 | 1/2000 |
| WO | WO 00/17191 | 3/2000 |
| WO | WO 00/74679 | 12/2000 |
| WO | WO 01/04103 | 1/2001 |
| WO | WO 01/10842 | 2/2001 |
| WO | WO 01/55106 | 8/2001 |
| WO | WO 01/55107 | 8/2001 |
| WO | WO 01/55109 | 8/2001 |
| WO | WO 01/70337 | 9/2001 |
| WO | WO 01/70708 | 9/2001 |
| WO | WO 02/18327 | 3/2002 |

(Continued)

OTHER PUBLICATIONS

Jordan, V. C. Nature Reviews: Drug Discovery, 2, 2003, p. 205.*

(Continued)

*Primary Examiner*—James O Wilson
*Assistant Examiner*—Douglas M Willis
(74) *Attorney, Agent, or Firm*—Vinit Kathardekar; Michael G. Smith

(57) ABSTRACT

A variety of low molecular weight, guanidino-containing dihydroisoquinolinoines capable of acting as MC4-R agonists are provided. The compounds are useful in treating MC4-R mediated diseases. The compounds have the structure ID where the values of the variable are defined herein.

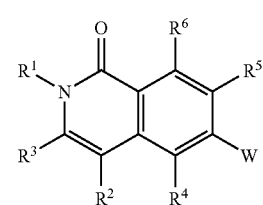

9 Claims, No Drawings

FOREIGN PATENT DOCUMENTS

| WO | WO 02/062766 | 8/2002 |
|---|---|---|
| WO | WO 02/062776 | 8/2002 |
| WO | WO 02/081443 | 10/2002 |
| WO | WO 03/072056 | 9/2003 |
| WO | WO 03/099818 | 12/2003 |
| WO | WO 2005/051391 | 6/2005 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*

Vippagunta, et al. Advanced Drug Delivery Reviews, 48, 2001, p. 18.*

Wolff, Manfred E., Ed. Burger's Medicinal Chemistry and Drug Discovery—Fifth Edition, New York: John Wiley & Sons, 1996, vol. 1, pp. 975-976.*

Asagarasu, A. et al., "Synthesis of Dipeptide-Type Human Immunodeficiency Virus (HIV) Protease Inhibitors with a Binding Unit to GP120," Chem. Pharm. Bull., vol. 46, No. 5, pp. 867-870, 1998, published by Pharmaceutical Society of Japan.

Banker, G.S., et al., "Modern Pharmaceutices, 3ed.," Marcel Dekker, New York, 1996, pp. 451-596.

Cupps et al. (1998): STN International, CAPLUS database, Columbus (Ohio), Accession No. 1998: 388504.

Fehm, H. L. et al., "The Melanocortin Melanocyte-Stimulating Hormone/Adrenocorticotropin$_{4-10}$ Decreases Body Fat in Humans," J. Clin. Endocrinology & Metabolism, vol. 86, No. 3, pp. 1144-1148, 2001, published by the Endocrine Society.

Fisher, et al., Int. J. Obes. Relat. Metab. Diord., 23, Suppl. I: 54-58, 1999.

Fong, T. M. et al., "ART (Protein Product of Agouti-Related Transcript) as an Antagonist of MC-3 and MC-4 Receptors," Biochemical and Biophysical Res. Comm., vol. 237, pp. 629-631, 1997, published by Academic Press.

Goodfellow, et al., Curr. Top. Med. Chem. 3(8): 855-83, 2003.

Hadley, M. E. et al., "The Proopiomelanocortin System," Ann. N. Y. Acad. Sci., 885:1, pp. 1-21, 1999.

Huszar, D. et al., "Targeted Disruption of the Melanocortin-4 Receptor Results in Obesity in Mice," Cell, vol. 88, pp. 131-141, Jan. 10, 1997, published by Cell Press.

Julia, M. et al., "Amidines and guanidines related to congocidine. III. Urea and trazene diamidines," Bull. Soc. Chim. Fr., No. 1, pp. 376-382, 1968, published by Masson Editeur, Paris, France.

Kiefer, L.L. et al., "Mutations in the Carboxyl Terminus of the Agouti Protein Decrease Agouti Inhibition of Ligand Binding to the Melanocortin Receptors," Biochemistry, vol. 36, pp. 2084-2090, 1997, published by American Chemical Society.

Lu, D. et al., "Agouti protein is an antagonist of the melanocyte-stimulating-hormone receptor," Nature, vol. 371, pp. 799-802, Oct. 27, 1994.

Mountjoy, K. G. et al., "The Cloning of a Family of Genes That Encode the Melanocortin Receptors," Science, vol. 257, pp. 1248-1251, Aug. 28, 1992.

Ollmann, M. M. et al., "Antagonism of Central melanocortin Receptors in Vitro and in Vivo by Agouti-Related Protein," Science, vol. 278, pp. 135-138, Oct. 3, 1997.

Rossi, M. et al., "A C-terminal fragment of Agouti-related protein increases feeding and antagonizes the effect of alpha-melanocyte stimulating hormone in vivo," Endocrinology, vol. 139, No. 10, pp. 4428-4431, 1998, published by The Endocrine Society.

Runti, C.; DeNardo, M.; Ulian F., "Fusaric Acid Derivatives and Analogues as Possible Antihypertensive Drugs," Il Farmaco Edizione Scientifica, vol. 36(4), pp. 260-268 (1981), published in Italy by the Society of Italian Pharmaceutical Science. This is an English-language document.

Smith, R. A. et al., "Discovery and Parallel Synthesis of a New Class of Cathepsin K Inhibitors," Bioorganic & Medicinal Chemistry Letters, vol. 11, pp. 2951-2954, 2001, published by Elsevier Science Ltd.

Smolnik, R. et al., "Brain Potentials and Attention after Acute and Subchronic Intranasal Administration of ACTH 4-10 and Desacetyl-α-MSH in Humans," Neuroendocrinology, vol. 70, pp. 63-72, 1999, published by S. Karger AG, Basel.

West, Anthony R., Solid State Chemistry and its Applications, Wiley, New York, 1988, pp. 358-365.

International Preliminary Report on Patentability and Written Opinion for PCT/US2004/039020 dated May 22, 2006.

International Search Report for PCT/US2004/039020 dated Apr. 19, 2005.

Supplementary European Search Report for EP 04811698.2 dated Oct. 14, 2008.

Examination Report for EP 03738964.0 dated Aug. 5, 2008.

Examination Report for EP 03738964.0 dated Jan. 31, 2008.

International Preliminary Examination Report for PCT/US03/16442 dated Feb. 17, 2004.

International Search Report for PCT/US03/16442 dated Oct. 9, 2003.

Supplementary European Search Report for EP 03738964.0 dated Jul. 25, 2006.

Examination Report for EP 04776069.9 dated Mar. 25, 2008.

International Preliminary Report on Patentability for PCT/US2004/015959 dated Sep. 8, 2005.

International Search Report for PCT/US2004/015959 dated Oct. 22, 2004.

* cited by examiner

SUBSTITUTED DIHYDROISOQUINOLINONE COMPOUNDS

CROSS-REFERENCES TO RELATED APPLICATIONS

This application, claims priority to U.S. Provisional Application No. 60/382,762 filed May 23, 2002, and U.S. Provisional Application No. 60/441,019 filed Jan. 17, 2003, the entire disclosures of which are incorporated herein by reference and for all purposes.

FIELD OF THE INVENTION

This invention relates to melanocortin-4 receptor (MC4-R) agonists and methods of their preparation. The invention also relates to methods of treating melanocortin-4 receptor-mediated diseases, such as obesity or diabetes, by activating the melanocortin-4 receptor with compounds provided herein.

BACKGROUND OF THE INVENTION

Melanocortins are peptide products resulting from post-translational processing of pro-opiomelanocortin and are known to have a broad array of physiological activities. The natural melanocortins include the different types of melanocyte stimulating hormone (α-MSH, β-MSH, γ-MSH) and ACTH. Of these, α-MSH and ACTH are considered to be the main endogenous melanocortins.

The melanocortins mediate their effects through melanocortin receptors (MC-Rs), a subfamily of G-protein coupled receptors. There are at least five different receptor subtypes (MC1-R to MC5-R). MC1-R mediates pigmentation of the hair and skin. MC2-R mediates the effects of ACTH on steroidogenesis in the adrenal gland. MC3-R and MC4-R are predominantly expressed in the brain. MC5-R is considered to have a role in the exocrine gland system.

The melanocortin-4 receptor (MC4-R) is a seven-transmembrane receptor. MC4-R may participate in modulating the flow of visual and sensory information, coordinate aspects of somatomotor control, and/or participate in the modulation of autonomic outflow to the heart. K. G. Mountjoy et al., *Science*, 257:1248-125 (1992). Significantly, inactivation of this receptor by gene targeting has resulted in mice that develop a maturity onset obesity syndrome associated with hyperphagia, hyperinsulinemia, and hyperglycemia. D. Husznar et al., *Cell*, 88(1): 131-41 (1997). MC4-R has also been implicated in other disease states including erectile disorders, cardiovascular disorders, neuronal injuries or disorders, inflammation, fever, cognitive disorders, and sexual behavior disorders. M. E. Hadley and C. Haskell-Luevano, *The proopiomelanocortin system*, Ann. N.Y. Acad. Sci., 885:1 (1999).

Furthermore, observations in connection with endogenous MC4-R antagonists indicate that MC4-R is implicated in endogenous energy regulation. For example, an agouti protein is normally expressed in the skin and is an antagonist of the cutaneous MC receptor involved in pigmentation, MC1-R. M. M. Ollmann et al., *Science*, 278:135-138 (1997). However, overexpression of agouti protein in mice leads to a yellow coat color due to antagonism of MC1-R and increased food intake and body weight due to antagonism of MC4-R. L. L. Kiefer et al., *Biochemistry*, 36: 2084-2090 (1997); D. S. Lu et al., *Nature*, 371:799-802 (1994). Agouti related protein (AGRP), an agouti protein homologue, antagonizes MC4-R but not MC1-R. T. M. Fong et al., *Biochem. Biophys. Res. Commun.* 237:629-631 (1997). Administration of AGRP in mice increases food intake and causes obesity but does not alter pigmentation. M. Rossi et al., *Endocrinology*, 139:4428-4431 (1998). Together, this research indicates that MC4-R participates in energy regulation, and therefore, identifies this receptor as a target for a rational drug design for the treatment of obesity.

In connection with MC4-R and its uncovered role in the etiology of obesity and food intake, the prior art includes reports of compounds and compositions that act as agonists or antagonists of MC4-R. As examples, U.S. Pat. No. 6,060,589 describes polypeptides that are capable of modulating signaling activity of melanocortin receptors. Also, U.S. Pat. Nos. 6,054,556 and 5,731,408 describe families of agonists and antagonists for MC4-R receptors that are lactam heptapeptides having a cyclic structure. WO 01/10842 discloses MC4-R binding compounds having a multitude of structures and methods of using such compounds to treat MC4-R associated disorders. Some of the compounds described include amidino- and guanidino-containing arenes and heteroarenes.

Various other classes of compounds have been disclosed as having MC4-R agonist activity. For example, WO 01/70708 and WO 00/74679 disclose MC4-R agonists that are piperidine compounds and derivatives, while WO 01/70337 and WO 99/64002 disclose MC-R agonists that are spiropiperidine derivatives. Other known melanocortin receptor agonists include aromatic amine compounds containing amino acid residues, particularly tryptophan residues, as disclosed in WO 01/55106. Similar agonists are disclosed in WO 01/055107 which comprise aromatic amine compounds containing tertiary amide or tertiary amine groups. Finally, WO 01/055109 discloses melanocortin receptor agonists comprising aromatic amines which are generally bisamides separated by a nitrogen-containing alkyl linker.

Guanidine-containing compounds having a variety of biological activities are also known in the prior art. For example, U.S. Pat. No. 4,732,916 issued to Satoh et al. discloses guanidine compounds useful as antiulcer agents; U.S. Pat. Nos. 4,874,864, 4,949,891, and 4,948,901 issued to Schnur et al. and EP 0343 894 disclose guanidino compounds useful as protease inhibitors and as anti-plasmin and anti-thrombin agents; and U.S. Pat. No. 5,352,704 issued to Okuyama et al. discloses a guanidino compound useful as an antiviral agent. Guanidine-containing compounds are also disclosed in other references. For example, U.S. Pat. No. 6,030,985 issued to Gentile et al. discloses guanidine compounds useful for treating and preventing conditions in which inhibition of nitric oxide synthetase is beneficial such as stroke, schizophrenia, anxiety, and pain. U.S. Pat. No. 5,952,381 issued to Chen et al. discloses certain guanidine compounds for use in selectively inhibiting or antagonizing $\alpha_v\beta_3$ integrins.

Various 5-, 6-, and 7-membered fully saturated 1-azacarbocyclic-2-ylidene derivatives of guanidine are disclosed as having anti-secretory and hypoglycemic activities by U.S. Pat. No. 4,211,867 issued to Rasmussen. Such compounds are also taught as useful for the treatment of cardiovascular disease. Other guanidine derivatives are disclosed by U.S. Pat. No. 5,885,985 issued to Macdonald et al. as useful in therapy to treat inflammation. Various guanidinobenzamide compounds are disclosed in WO 02/18327. The guanidinobenzamides are disclosed as useful for treating obesity and type II diabetes.

Nevertheless, there remains a need for potent and specific agonists of MC4-R that are low molecular weight small molecules. Methods of treating a melanocortin-4 receptor mediated disease, such as obesity, with such non-peptide drugs, are also particularly desirable.

SUMMARY OF THE INVENTION

The instant invention provides potent and specific agonists of MC4-R that are low molecular weight small molecules. Thus, there has been provided, in accordance with one aspect of the invention, compounds of formula IA, IB, or IC:

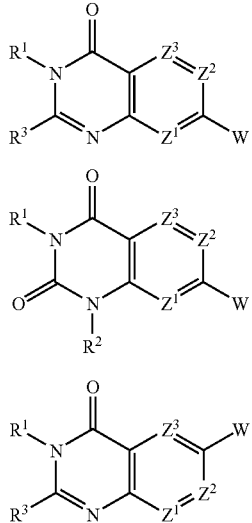

wherein $Z^1$ is selected from the group consisting of $CR^4$ and N;
$Z^2$ is selected from the group consisting of $CR^5$ and N;
$Z^3$ is selected from the group consisting of $CR^6$ and N;
$R^1$ is selected from the group consisting of substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;
$R^2$ is selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups;
$R^3$ is selected from the group consisting of H, and substituted and unsubstituted arylalkyl, heteroarylalkyl, alkoxy, alkylamino, dialkylamino, aryl, heteroaryl, heterocyclyl, cycloalkyl, heterocyclylalkyl, cycloalkylalkyl, alkenyl, alkynyl, and alkyl groups;
$R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;
W is a group of formula IIA or IIB;

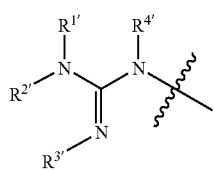

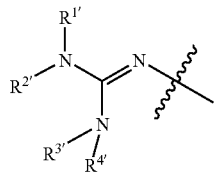

$R^{1'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;
$R^{2'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;
or $R^{1'}$ and $R^{2'}$, together with the nitrogen to which they are bound, form a substituted or unsubstituted heterocyclyl or heteroaryl group;
$R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups; and
$R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups.

Compounds provided by the invention further include prodrugs of the compound of formula IA, IB, and IC, pharmaceutically acceptable salts thereof, stereoisomers thereof, tautomers thereof, hydrates thereof, hydrides thereof, or solvates thereof.

The invention further provides compounds of formula IA and IC in which $R^3$ is H.

The invention further provides compounds of formula IA, IB, and IC in which $Z^1$ is a $CR^4$ group, $Z^2$ is a $CR^5$ group, and $Z^3$ is a $CR^6$ group. In some such embodiments, at least one of $R^4$, $R^5$, or $R^6$ is a F.

The invention further provides compounds of formula IA, IB, and IC in which at least one of $Z^1$, $Z^2$, or $Z^3$ is N. In some such embodiments, $Z^1$ is N. In other such embodiments, $Z^2$ is N.

The invention further provides compounds of formula IA, IB, and IC in which $R^{3'}$ is selected from the group consisting of substituted and unsubstituted cycloalkyl, polycyclic cycloalkyl, alkenyl, alkyl, and aryl groups. In other embodiments of compounds of formula IA, IB, and IC, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of compounds of formula IA, IB, and IC, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl (polycyclic cycloalkyl), fluoromethyl(polycyclic cycloalkyl), and fluoro(polycyclic cycloalkyl) groups.

The invention further provides compounds of formula IA, IB, and IC in which $R^{1'}$ is H and $R^{2'}$ is selected from the group consisting of substituted and unsubstituted alkyl, arylalkyl, and heteroarylalkyl groups. In still other embodiments of compounds of formula IA, IB, and IC, $R^{1'}$ is H and $R^{2'}$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still other embodiments of compounds of formula IA, IB, and IC, $R^{1'}$ and $R^{2'}$ may be the same or different and are each independently selected from the group consisting of substituted and unsubstituted alkyl, arylalkyl, and heteroarylalkyl groups. In still other embodiments of compounds of formula IA, IB, and IC, $R^{1'}$ and $R^{2'}$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In still other embodiments of compounds of formula IA, IB, and IC, $R^{1'}$ and $R^{2'}$, together with the nitrogen to which they are bound, form a substituted or unsubstituted heterocyclyl group. In still other embodiments of compounds of formula IA, IB, and IC, $R^{1'}$ and $R^{2'}$, together with the nitrogen to which they are bound, form a substituted or unsubstituted saturated heterocyclyl group comprising at least one heteroatom selected from the group consisting of O, S, and N, in addition to the nitrogen atom to which $R^{1'}$ and $R^{2'}$ are bound. In still other embodiments of compounds of formula IA, IB, and IC, $R^{1'}$ and $R^{2'}$, together with the nitrogen to which they are bound, form a substituted or unsubstituted piperazino, morpholino, pyrrolidino, piperidino, homopiperazino, or azepino group. In still other embodiments of compounds of formula IA, IB, and IC, $R^{1'}$ and $R^{2'}$, together with the nitrogen to which they are bound, form a piperazino group optionally substituted by one or two methyl groups.

The invention further provides compounds of formula IA, IB, and IC in which $R^1$ is a 2,4-disubstituted phenylethyl group. In still other embodiments of compounds of formula IA, IB, and IC, $R^1$ is selected from the group consisting of 2,4-dihalophenylethyl, and 2,4-dialkylphenylethyl groups. In still other embodiments of compounds of formula IA, IB, and IC, $R^1$ is selected from the group consisting of phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl groups, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl) ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups.

In still further embodiments, the invention provides compounds of formula IA, IB and IC in which $R^1$ is a substituted or unsubstituted alkenyl group such as a substituted or unsubstituted allyl group or a substituted or unsubstituted vinyl group.

The invention further provides compounds of formula IB in which $R^2$ is H.

In still further embodiments, the invention provides compounds of formula IA and IC in which $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups.

The instant invention provides a second group of potent and specific agonists of MC4-R that are low molecular weight small molecules. Thus, there has been provided, in accordance with one aspect of the invention, compounds of formula IA and IC:

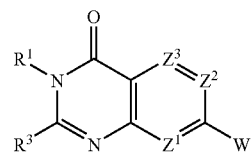

IA

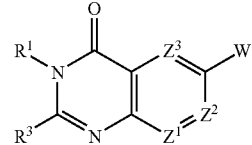

IC wherein

Z¹ is selected from the group consisting of CR⁴ and N;

Z² is selected from the group consisting of CR⁵ and N;

Z³ is selected from the group consisting of CR⁶ and N;

R¹ is selected from the group consisting of H, substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;

R³ is selected from the group consisting of substituted and unsubstituted arylalkyl, heteroarylalkyl, alkoxy, aryloxyalkyl, alkylamino, dialkylamino, aryl, heteroaryl, heterocyclyl, cycloalkyl, heterocyclylalkyl, cycloalkylalkyl, alkenyl, alkynyl, alkyl groups, and —C(═NH)-heterocyclyl groups, and groups of formula -LR⁷;

R⁴, R⁵, and R⁶ are independently selected from the group consisting of H, Cl, I, F, Br, OH, NH₂, CN, NO₂, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

W is a group of formula IIA or IIB;

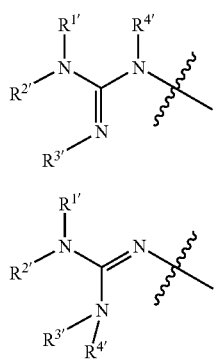

R¹' is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;

R²' is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;

or R¹' and R²', together with the nitrogen to which they are bound, form a substituted or unsubstituted heterocyclyl or heteroaryl group;

R³' is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups;

R⁴' is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups;

L is selected from the group consisting of a covalent bond, —CH₂—, —O—, —S—, and —NH—;

R⁷ is selected from the group consisting of substituted and unsubstituted arylaminoalkyl, aryl, and aryloxyalkyl groups or is selected from a group of formula IIC;

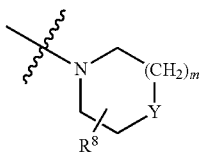

wherein Y is selected from the group consisting of CH₂, O, S, and NR⁹ where R⁹ is selected from the group consisting of H, and substituted or unsubstituted alkyl groups;

R⁸ is selected from the group consisting of H, a halogen, hydroxyl, carboxylic acid, and substituted or unsubstituted alkyl, amino, alkylamino, dialkylamino, alkylaminoalkyl, heterocyclyl, alkoxy, carbonyl, and aminocarbonyl groups; and m is an integer selected from 0, 1, and 2.

In some aspects of the invention, compounds provided of the second group of potent and specific agonists of MC4-R further include prodrugs of the compounds of formula IA and IC, pharmaceutically acceptable salts thereof, stereoisomers thereof, tautomers thereof, hydrates thereof, hydrides thereof, or solvates thereof.

In some aspects of the invention of compounds of the second group of potent and specific agonists of MC4-R, the invention further provides compounds of formula IA and IC in which R¹ is H or an alkyl group such as a methyl, ethyl, propyl, butyl, or pentyl group. In some such embodiments, R¹ is H whereas in other such embodiments, R¹ is a methyl group.

In some aspects of the invention of compounds of the second group of potent and specific agonists of MC4-R, the invention further provides compounds of formula IA and IC in which Z¹ is a CR⁴ group, Z² is a CR⁵ group, and Z³ is a CR⁶ group. In some such embodiments, at least one of R⁴, R⁵ or R⁶ is a F.

In some aspects of the invention of compounds of the second group of potent and specific agonists of MC4-R, the invention further provides compounds of formula IA and IC in which at least one of Z¹, Z², or Z³ is N. In some such embodiments, Z¹ is N. In other such embodiments, Z² is N.

In some aspects of the invention of compounds of the second group of potent and specific agonists of MC4-R, the invention further provides compounds of formula IA and IC in which R³' is selected from the group consisting of substituted and unsubstituted cycloalkyl, polycyclic cycloalkyl, alkenyl, alkyl, and aryl groups. In other embodiments of the second group of compounds of formula IA and IC, R³' is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2- dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of the second group of compounds of formula IA and IC, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl (polycyclic cycloalkyl), fluoromethyl(polycyclic cycloalkyl), and fluoro(polycyclic cycloalkyl) groups.

In some aspects of the invention of compounds of the second group of potent and specific agonists of MC4-R, the invention further provides compounds of formula IA and IC in which $R^{1'}$ is H and $R^{2'}$ is selected from the group consisting of substituted and unsubstituted alkyl, arylalkyl, and heteroarylalkyl groups. In still other embodiments of the second group of compounds of formula IA and IC, $R^{1'}$ is H and $R^{2'}$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still other embodiments of the second group of compounds of formula IA and IC, $R^{1'}$ and $R^{2'}$ may be the same or different and are each independently selected from the group consisting of substituted and unsubstituted alkyl, arylalkyl, and heteroarylalkyl groups. In still other embodiments of the second group of compounds of formula IA and IC, $R^{1'}$ and $R^{2'}$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In still other embodiments of the second group of compounds of formula IA and IC, $R^{1'}$ and $R^{2'}$, together with the nitrogen to which they are bound, form a substituted or unsubstituted heterocyclyl group. In still other embodiments of the second group of compounds of formula IA and IC, $R^{1'}$ and $R^{2'}$, together with the nitrogen to which they are bound, form a substituted or unsubstituted saturated heterocyclyl group comprising at least one heteroatom selected from the group consisting of O, S, and N, in addition to the nitrogen atom to which $R^{1'}$ and $R^{2'}$ are bound. In still other embodiments of the second group of compounds of formula IA and IC, $R^{1'}$ and $R^{2'}$, together with the nitrogen to which they are bound, form a substituted or unsubstituted piperazino, morpholino, pyrrolidino, piperidino, homopiperazino, or azepino group. In still other embodiments of the second group of compounds of formula IA and IC, $R^{1'}$ and $R^{2'}$, together with the nitrogen to which they are bound, form a piperazino group optionally substituted by one or two methyl groups.

In some aspects of the invention of compounds of the second group of potent and specific agonists of MC4-R, the invention further provides compounds of formula IA and IC in which $R^1$ is a 2,4-disubstituted phenylethyl group. In still other embodiments of the second group of compounds of formula IA and IC, $R^1$ is selected from the group consisting of 2,4-dihalophenylethyl, and 2,4-dialkylphenylethyl groups. In still other embodiments of the second group of compounds of formula IA and IC, $R^1$ is selected from the group consisting of phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl groups, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups.

In still further embodiments, the invention provides compounds of formula IA and IC in which $R^1$ is a substituted or unsubstituted alkenyl group such as a substituted or unsubstituted allyl group or a substituted or unsubstituted vinyl group.

In still further embodiments, the invention provides compounds of formula IA and IC in which $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups.

In some aspects of the invention of compounds of the second group of potent and specific agonists of MC4-R, the invention further provides compounds of formula IA and IC in which $R^3$ is a 2,4-disubstituted phenylethyl group. In still other embodiments of the second group of compounds of formula IA and IC, $R^3$ is selected from the group consisting of 2,4-dihalophenylethyl, and 2,4-dialkylphenylethyl groups. In still other embodiments of the second group of compounds of formula IA and IC, $R^3$ is selected from the group consisting of phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl groups, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some of the embodiments described in this paragraph, $R^1$ is H or is an alkyl group having from one to eight carbon atoms. In some of the embodiments described in this paragraph, $R^1$ is H whereas in other such embodiments $R^1$ is a methyl, ethyl, or propyl group.

In some aspects of the invention of compounds of the second group of potent and specific agonists of MC4-R, the invention further provides compounds of formula IA and IC in which $R^3$ is a substituted alkyl group such as a substituted or unsubstituted aryloxyalkyl group or a substituted or unsubstituted heteroaryloxyalkyl group. In some such embodiments, $R^3$ is a substituted or unsubstituted aryloxymethyl group. In some such embodiments, of the second group of compounds of formula IA and IC, $R^3$ is selected from the group consisting of —$CH_2$—O-aryl groups where the aryl group is substituted with one or more halogen group such as with one or more Cl or F. In some such embodiments, the aryl group is additionally substituted with an alkoxy group such as a methoxy or ethoxy group. In some embodiments of the second group of compounds of formula IA and IC, $R^3$ is a —$CH_2$—O-aryl group where the aryl group is selected from the group consisting of 2,4-difluorophenyl, 4-fluorophenyl, 2-fluorophenyl, 2-fluoro-4-methoxyphenyl, 2,4-dichlorophenyl, 4-chlorophenyl, 2-chlorophenyl, and 2-chloro-4-methoxyphenyl groups. In other embodiments of the second group of compounds of formula IA and IC, $R^3$ is a heterocyclylalkyl group. In some other embodiments of compounds of formula IA and IC, $R^3$ is a substituted or unsubstituted arylalkoxyalkyl group or a heteroarylalkoxyalkyl group.

In some aspects of the invention of compounds of the second group of potent and specific agonists of MC4-R, the invention further provides compounds of formula IA and IC in which $R^3$ is a substituted or unsubstituted heterocyclylalkyl group. In some such embodiments, $R^3$ is a substituted or unsubstituted heterocyclylmethyl group. In some such embodiments, the heterocyclyl group is selected from the group consisting of substituted and unsubstituted 1H-tetrazole, piperazine, piperidine, imidazole, and morpholine groups. In some such embodiments, $R^3$ is a —$CH_2$-heterocyclyl group where the heterocyclyl group is a 1H-tetrazole, an imidazole, an N-methylpiperazine, a 4-hydroxypiperidine, a 3-hydroxypiperidine, or a morpholine. In still other embodiments of the second group of compounds of formula IA and IC, $R^3$ is a heterocyclyl group. In some embodiments of the second group of compounds of formula IA and IC, $R^3$ is a substituted or unsubstituted piperazinyl group such as an N-methylpiperazinyl group, is a substituted or unsubstituted pyridine group, is a substituted or unsubstituted tetrazole group, is a substituted or unsubstituted cycloalkyl group such as a 4-methylcyclohexyl group, or is a substituted or unsubstituted phenyl group. In yet other embodiments of the second group of compounds of formula IA and IC, $R^3$ is an alkoxyalkyl group such as a methoxyalkyl group or an ethoxyalkyl group. In some such embodiments, $R^3$ is a an alkoxyalkyl group such as an alkoxymethyl group such as a methoxymethyl group.

The instant invention provides a third group of potent and specific agonists of MC4-R that are low molecular weight small molecules. Thus, there has been provided, in accordance with one aspect of the invention, compounds of formula ID:

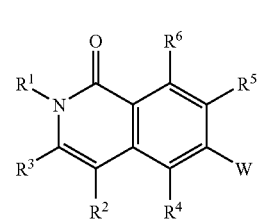

ID wherein $R^1$ is selected from the group consisting of H, substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;

$R^2$ and $R^3$ are independently selected from the group consisting of —H, substituted and unsubstituted arylalkyl, heteroarylalkyl, alkoxy, aryloxyalkyl, alkylamino, dialkylamino, aryl, heteroaryl, heterocyclyl, cycloalkyl, heterocyclylalkyl, cycloalkylalkyl, alkenyl, alkynyl, alkyl groups, and —C(=NH)-heterocyclyl groups, and groups of formula -$LR^7$;

$R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

W is a group of formula IIA or IIB;

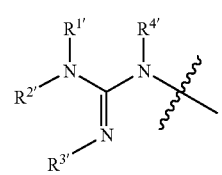

IIA

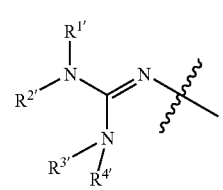

IIB $R^{1'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;

$R^{2'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;

or $R^{1'}$ and $R^{2'}$, together with the nitrogen to which they are bound, form a substituted or unsubstituted heterocyclyl or heteroaryl group;

$R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups;

$R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups;

L is selected from the group consisting of a covalent bond, —CH$_2$—, —O—, —S—, and —NH—;

$R^7$ is selected from the group consisting of substituted and unsubstituted arylaminoalkyl, aryl, and aryloxyalkyl groups or is selected from a group of formula IIC;

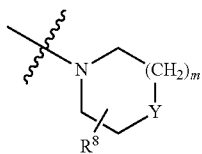

IIC wherein Y is selected from the group consisting of CH$_2$, O, S, and NR$^9$ where R$^9$ is selected from the group consisting of H, and substituted or unsubstituted alkyl groups;

$R^8$ is selected from the group consisting of H, a halogen, hydroxyl, carboxylic acid, and substituted or unsubstituted alkyl, amino, alkylamino, dialkylamino, alkylaminoalkyl, heterocyclyl, alkoxy, carbonyl, and aminocarbonyl groups; and m is an integer selected from 0, 1, and 2.

In some aspects of the invention, compounds provided of the third group of potent and specific agonists of MC4-R further include prodrugs of the compounds of formula ID, pharmaceutically acceptable salts thereof, stereoisomers thereof, tautomers thereof, hydrates thereof, hydrides thereof, or solvates thereof.

In some aspects of the invention of compounds of the third group of potent and specific agonists of MC4-R, the invention further provides compounds of formula ID in which $R^1$ is H or an alkyl group such as a methyl, ethyl, propyl, butyl, or pentyl group. In some such embodiments, $R^1$ is H whereas in other such embodiments, $R^1$ is a methyl group.

In some aspects of the invention of compounds of the third group of potent and specific agonists of MC4-R, the invention further provides compounds of formula ID in which $R^2$ is H or an alkyl group such as a methyl, ethyl, propyl, butyl, or pentyl group.

In some aspects of the invention of compounds of the third group of potent and specific agonists of MC4-R, the invention further provides compounds of formula ID in which at least one of $R^4$, $R^5$, or $R^6$ is a F.

In some aspects of the invention of compounds of the third group of potent and specific agonists of MC4-R, the invention further provides compounds of formula ID in which $R^{3'}$ is selected from the group consisting of substituted and unsubstituted cycloalkyl, polycyclic cycloalkyl, alkenyl, alkyl, and aryl groups. In other embodiments of the third group of compounds of formula ID, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of the third group of compounds of formula ID, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups.

In some aspects of the invention of compounds of the third group of potent and specific agonists of MC4-R, the invention further provides compounds of formula ID in which $R^{1'}$ is H and $R^{2'}$ is selected from the group consisting of substituted and unsubstituted alkyl, arylalkyl, and heteroarylalkyl groups. In still other embodiments of the third group of compounds of formula ID, $R^{1'}$ is H and $R^{2'}$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still other embodiments of the third group of compounds of formula ID, $R^{1'}$ and $R^{2'}$ may be the same or different and are each independently selected from the group consisting of substituted and unsubstituted alkyl, arylalkyl, and heteroarylalkyl groups. In still other embodiments of the third group of compounds of formula ID, $R^{1'}$ and $R^{2'}$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In still other embodiments of the third group of compounds of formula ID, $R^{1'}$ and $R^{2'}$, together with the nitrogen to which they are bound, form a substituted or unsubstituted heterocyclyl group. In still other embodiments of the third group of compounds of formula ID, $R^{1'}$ and $R^{2'}$, together with the nitrogen to which they are bound, form a substituted or unsubstituted saturated heterocyclyl group comprising at least one heteroatom selected from the group consisting of O, S, and N, in addition to the nitrogen atom to which $R^{1'}$ and $R^{2'}$ are bound. In still other embodiments of the third group of compounds of formula ID, $R^{1'}$ and $R^{2'}$, together with the nitrogen to which they are bound, form a substituted or unsubstituted piperazino, morpholino, pyrrolidino, piperidino, homopiperazino, or azepino group. In still other embodiments of the third group of compounds of formula ID, $R^{1'}$ and $R^{2'}$, together with the nitrogen to which they are bound, form a piperazino group optionally substituted by one or two methyl groups.

In some aspects of the invention of compounds of the third group of potent and specific agonists of MC4-R, the invention further provides compounds of formula ID in which $R^1$ is a 2,4-disubstituted phenylethyl group. In still other embodiments of the third group of compounds of formula ID, $R^1$ is selected from the group consisting of 2,4-dihalophenylethyl, and 2,4-dialkylphenylethyl groups. In still other embodiments of the third group of compounds of formula ID, $R^1$ is selected from the group consisting of phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl groups, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups.

In still further embodiments, the invention provides compounds of formula ID in which $R^1$ is a substituted or unsubstituted alkenyl group such as a substituted or unsubstituted allyl group or a substituted or unsubstituted vinyl group.

In still further embodiments, the invention provides compounds of formula ID in which $R^2$ is H or a substituted or unsubstituted alkyl group.

In still further embodiments, the invention provides compounds of formula ID in which $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups.

In some aspects of the invention of compounds of the third group of potent and specific agonists of MC4-R, the invention further provides compounds of formula ID in which $R^3$ is a 2,4-disubstituted phenylethyl group. In still other embodiments of the third group of compounds of formula ID, $R^3$ is selected from the group consisting of 2,4-dihalophenylethyl, and 2,4-dialkylphenylethyl groups. In still other embodiments of the third group of compounds of formula ID, $R^3$ is selected from the group consisting of phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl groups, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some of the embodiments described in this paragraph, $R^1$ is H or is an alkyl group having from one to eight carbon atoms. In some of the embodiments described in this paragraph, $R^1$ is H whereas in other such embodiments $R^1$ is a methyl, ethyl, or propyl group.

In some aspects of the invention of compounds of the third group of potent and specific agonists of MC4-R, the invention further provides compounds of formula ID in which $R^3$ is a substituted alkyl group such as a substituted or unsubstituted aryloxyalkyl group or a substituted or unsubstituted heteroaryloxyalkyl group. In some such embodiments, $R^3$ is a substituted or unsubstituted aryloxymethyl group. In some such embodiments, of the third group of compounds of formula ID, $R^3$ is selected from the group consisting of —CH$_2$—O-aryl groups where the aryl group is substituted with one or more halogen group such as with one or more Cl or F. In some such embodiments, the aryl group is additionally substituted with an alkoxy group such as a methoxy or ethoxy group. In some embodiments of the third group of compounds of formula ID, $R^3$ is a —CH$_2$—O-aryl group where the aryl group is selected from the group consisting of 2,4-difluorophenyl, 4-fluorophenyl, 2-fluorophenyl, 2-fluoro-4-methoxyphenyl, 2,4-dichlorophenyl, 4-chlorophenyl, 2-chlorophenyl, and 2-chloro-4-methoxyphenyl groups. In other embodiments of the third group of compounds of formula ID, $R^3$ is a heterocyclylalkyl group. In some other embodiments of compounds of formula ID, $R^3$ is a substituted or unsubstituted arylalkoxyalkyl group or a heteroarylalkoxyalkyl group.

In some aspects of the invention of compounds of the third group of potent and specific agonists of MC4-R, the invention further provides compounds of formula ID in which $R^3$ is a substituted or unsubstituted heterocyclylalkyl group. In some such embodiments, $R^3$ is a substituted or unsubstituted heterocyclylmethyl group. In some such embodiments, the heterocyclyl group is selected from the group consisting of substituted and unsubstituted 1H-tetrazole, piperazine, piperidine, imidazole, and morpholine groups. In some such embodiments, $R^3$ is a —CH$_2$-heterocyclyl group where the heterocyclyl group is a 1H-tetrazole, an imidazole, an N-methylpiperazine, a 4-hydroxypiperidine, a 3-hydroxypiperidine, or a morpholine. In still other embodiments of the third group of compounds of formula ID, $R^3$ is a heterocyclyl group. In some embodiments of the third group of compounds of formula ID, $R^3$ is a substituted or unsubstituted piperazinyl group such as an N-methylpiperazinyl group, is a substituted or unsubstituted pyridine group, is a substituted or unsubstituted tetrazole group, is a substituted or unsubstituted cycloalkyl group such as a 4-methylcyclohexyl group, or is a substituted or unsubstituted phenyl group. In yet other embodiments of the third group of compounds of formula ID, $R^3$ is an alkoxyalkyl group such as a methoxyalkyl group or an ethoxyalkyl group. In some such embodiments, $R^3$ is a an alkoxyalkyl group such as an alkoxymethyl group such as a methoxymethyl group.

The instant invention provides a fourth group of potent and specific agonists of MC4-R that are low molecular weight small molecules. Thus, there has been provided, in accordance with one aspect of the invention, compounds of formula IE:

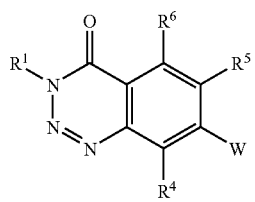

IE wherein $R^1$ is selected from the group consisting of H, substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups;

$R^4$, $R^5$, and $R^6$ are independently selected from the group consisting of H, Cl, I, F, Br, OH, NH$_2$, CN, NO$_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups;

W is a group of formula IIA or IIB;

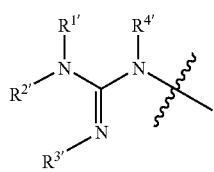

IIA

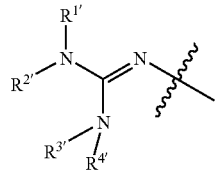

IIB $R^{1'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;

$R^{2'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups;

or $R^{1'}$ and $R^{2'}$, together with the nitrogen to which they are bound, form a substituted or unsubstituted heterocyclyl or heteroaryl group;

$R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups; and $R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups.

In some aspects of the invention, compounds provided of the fourth group of potent and specific agonists of MC4-R further include prodrugs of the compounds of formula IE, pharmaceutically acceptable salts thereof, stereoisomers thereof, tautomers thereof, hydrates thereof, hydrides thereof, or solvates thereof.

In some aspects of the invention of compounds of the fourth group of potent and specific agonists of MC4-R, the invention further provides compounds of formula IE in which $R^1$ is H or an alkyl group such as a methyl, ethyl, propyl, butyl, or pentyl group. In some such embodiments, $R^1$ is H whereas in other such embodiments, $R^1$ is a methyl group.

In some aspects of the invention of compounds of the fourth group of potent and specific agonists of MC4-R, the invention further provides compounds of formula IE in which at least one of $R^4$, $R^5$, or $R^6$ is a F.

In some aspects of the invention of compounds of the fourth group of potent and specific agonists of MC4-R, the invention further provides compounds of formula IE in which $R^{3'}$ is selected from the group consisting of substituted and unsubstituted cycloalkyl, polycyclic cycloalkyl, alkenyl, alkyl, and aryl groups. In other embodiments of the fourth group of compounds of formula IE, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4- dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of the fourth group of compounds of formula IE, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups.

In some aspects of the invention of compounds of the fourth group of potent and specific agonists of MC4-R, the invention further provides compounds of formula IE in which $R^{1'}$ is H and $R^{2'}$ is selected from the group consisting of substituted and unsubstituted alkyl, arylalkyl, and heteroarylalkyl groups. In still other embodiments of the fourth group of compounds of formula IE, $R^{1'}$ is H and $R^{2'}$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still other embodiments of the fourth group of compounds of formula IE, $R^{1'}$ and $R^{2'}$ may be the same or different and are each independently selected from the group consisting of substituted and unsubstituted alkyl, arylalkyl, and heteroarylalkyl groups. In still other embodiments of the fourth group of compounds of formula IE, $R^{1'}$ and $R^{2'}$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups.

In still other embodiments of the fourth group of compounds of formula IE, $R^{1'}$ and $R^{2'}$, together with the nitrogen to which they are bound, form a substituted or unsubstituted heterocyclyl group. In still other embodiments of the fourth group of compounds of formula IE, $R^{1'}$ and $R^{2'}$, together with the nitrogen to which they are bound, form a substituted or unsubstituted saturated heterocyclyl group comprising at least one heteroatom selected from the group consisting of O, S, and N, in addition to the nitrogen atom to which $R^{1'}$ and $R^{2'}$ are bound. In still other embodiments of the fourth group of compounds of formula IE, $R^{1'}$ and $R^{2'}$, together with the nitrogen to which they are bound, form a substituted or unsubstituted piperazino, morpholino, pyrrolidino, piperidino, homopiperazino, or azepino group. In still other embodiments of the fourth group of compounds of formula IE, $R^{1'}$ and $R^{2'}$, together with the nitrogen to which they are bound, form a piperazino group optionally substituted by one or two methyl groups.

In some aspects of the invention of compounds of the fourth group of potent and specific agonists of MC4-R, the invention further provides compounds of formula IE in which $R^1$ is a 2,4-disubstituted phenylethyl group. In still other embodiments of the fourth group of compounds of formula IE, $R^1$ is selected from the group consisting of 2,4-dihalophenylethyl, and 2,4-dialkylphenylethyl groups. In still other embodiments of the fourth group of compounds of formula IE, $R^1$ is selected from the group consisting of phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl groups, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups.

In still further embodiments, the invention provides compounds of formula IE in which $R^1$ is a substituted or unsubstituted alkenyl group such as a substituted or unsubstituted allyl group or a substituted or unsubstituted vinyl group.

There has also been provided, in accordance with another aspect of the invention, a composition such as a pharmaceutical formulation or medicament comprising a compound according to the instant invention and a pharmaceutically acceptable carrier. The invention further provides the use of the compounds of the invention in preparing a medicament for use in treating an MC4-R mediated disease. In some embodiments, such a disease is obesity or type II diabetes.

There has also been provided, in accordance with another aspect of the invention, a method of treating an MC4-R mediated disease, comprising administering to a subject in need thereof, a compound or composition of the instant invention.

In one embodiment, a disease to be treated by those methods of the instant invention is obesity or type II diabetes.

In one embodiment, a compound or composition of the invention is intranasally administered.

In one embodiment, a compound or composition of the invention is administered to a human subject.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENT

The instant invention relates to novel classes of small molecule melanocortin-4 receptor (MC4-R) agonists. These compounds can be formulated into compositions and are useful in activating MC4-R, or in the treatment of MC4-R-mediated diseases, such as obesity, type II diabetes, erectile dysfunction, polycystic ovary disease, complications resulting from or associated with obesity and diabetes, and Syndrome X.

The following definitions are used throughout this specification.

Alkyl groups include straight chain and branched alkyl groups having from 1 to about 8 carbon atoms. Examples of straight chain alkyl groups include methyl, ethyl, propyl, butyl, pentyl, hexyl, heptyl, and octyl groups. Examples of branched alkyl groups, include, but are not limited to, isopropyl, sec-butyl, t-butyl, and isopentyl groups. Representative substituted alkyl groups may be substituted one or more times with, for example, amino, thio, alkoxy, or halo groups such as F, Cl, Br, and I groups.

Cycloalkyl groups are cyclic alkyl groups such as, but not limited to, cyclopropyl, cyclobutyl, cyclopentyl, cyclohexyl, cycloheptyl, and cyclooctyl groups. Cycloalkyl groups also includes rings that are substituted with straight or branched chain alkyl groups as defined above, and further include cycloalkyl groups that are substituted with other rings including fused rings such as, but not limited to, decalinyl, tetrahydronaphthyl, and indanyl. Cycloalkyl groups also include polycyclic cycloalkyl groups such as, but not limited to, norbornyl, adamantyl, born, camphenyl, isocamphenyl, and carenyl groups. Representative substituted cycloalkyl groups may be mono-substituted or substituted more than once, such as, but not limited to, 2,2-, 2,3-, 2,4-2, 5 or 2,6-disubstituted cyclohexyl groups or mono-, di- or tri-substituted norbornyl or cycloheptyl groups, which may be substituted with, for example, alkyl, alkoxy, amino, thio, cyano, or halo groups.

Alkenyl groups are straight chain, branched or cyclic lower alkyl groups having 2 to about 8 carbon atoms, and further including at least one double bond, as exemplified, for instance, by vinyl, propenyl, 2-butenyl, 3-butenyl, isobutenyl, cyclohexenyl, cyclopentenyl, cyclohexadienyl, butadienyl, pentadienyl, and hexadienyl groups among others.

Alkynyl groups are straight chain or branched lower alkyl groups having 2 to about 8 carbon atoms, and further including at least one triple bond, as exemplified by groups, including, but not limited to, ethynyl, propynyl, and butynyl groups.

Aryl groups are cyclic aromatic hydrocarbons that do not contain heteroatoms. Thus aryl groups include, but are not limited to, phenyl, azulene, heptalene, biphenylene, indacene, fluorene, phenanthrene, triphenylene, pyrene, naphthacene, chrysene, biphenyl, anthracenyl, and naphthenyl groups. Although the phrase "aryl groups" includes groups containing fused rings, such as fused aromatic-aliphatic ring systems, it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once, such as, but not limited to, 2-, 3-, 4-, 5-, or 6-substituted phenyl or benzyl groups, which may be substituted with groups including, but not limited to, amino, alkoxy, alkyl, cyano, or halo.

Cycloalkylalkyl groups are alkyl groups as defined above in which a hydrogen or carbon bond of an alkyl group is replaced with a bond to a cycloalkyl group as defined above.

Arylalkyl groups are alkyl groups as defined above in which a hydrogen or carbon bond of an alkyl group is replaced with a bond to an aryl group as defined above.

Heterocyclyl groups are nonaromatic ring compounds containing 3 or more ring members, of which, one or more is a heteroatom such as, but not limited to, N, O, and S. The phrase "heterocyclyl group" includes fused ring species including those comprising fused aromatic and nonaromatic groups. The phrase also includes polycyclic ring systems containing a heteroatom such as, but not limited to, quinuclidyl. However, the phrase does not include heterocyclyl groups that have other groups, such as alkyl or halo groups, bonded to one of the ring members. Rather, these are referred to as "substituted heterocyclyl groups". Heterocyclyl groups include, but are not limited to, piperazino, morpholino, thiomorpholino, pyrrolidino, piperidino and homopiperazino groups. Representative substituted heterocyclyl groups may be mono-substituted or substituted more than once, such as, but not limited to, morpholino or piperazino groups, which are 2-, 3-, 4-, 5-, or 6-substituted, or disubstituted with groups including, but not limited to, amino, alkoxy, alkyl, cyano, or halo.

Heteroaryl groups are aromatic ring compounds containing 3 or more ring members, of which, one or more is a heteroatom such as, but not limited to, N, O, and S. Heteroaryl groups include, but are not limited to, groups such as furan, thiophene, pyrrole, isopyrrole, diazole, imidazole, isoimidazole, triazole, dithiole, oxathiole, isoxazole, oxazole, thiazole, isothiazole, oxadiazole, oxatriazole, dioxazole, oxathiazole, pyran, dioxin, pyridine, pyrimidine, pyridazine, pyrazine, triazine, oxazine, isoxazine, oxathiazine, azepin, oxepin, thiepin, diazepine, benzofuran, and isobenzofuran. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups". Representative substituted heteroaryl groups may be substituted one or more times with groups including, but not limited to, amino, alkoxy, alkyl, cyano, or halo.

Heterocyclylalkyl groups are alkyl groups as defined above in which a hydrogen or carbon bond of an alkyl group is replaced with a bond to a heterocyclyl group as defined above.

Heteroarylalkyl groups are alkyl groups as defined above in which a hydrogen or carbon bond of an alkyl group is replaced with a bond to a heteroaryl group as defined above.

Aminocarbonyl groups are groups of the formula RR'NC(O)—, wherein R or R' may be the same or different, and each is independently selected from H, or substituted or unsubstituted alkyl, cycloalkyl, aryl, heterocyclyl or heteroaryl groups, as defined above.

In general, "substituted" refers to a group as defined above in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles.

Substituted cycloalkyl, substituted aryl, substituted heterocyclyl and substituted heteroaryl also include rings and fused ring systems in which a bond to a hydrogen atom is replaced with a bond to a carbon atom. Therefore, substituted cycloalkyl, substituted aryl, substituted heterocyclyl and substituted heteroaryl groups may also be substituted with alkyl groups as defined above.

Pharmaceutically acceptable salts include a salt with an inorganic base, organic base, inorganic acid, organic acid, or basic or acidic amino acid. As salts of inorganic bases, the invention includes, for example, alkali metals such as sodium or potassium, alkali earth metals such as calcium and magnesium or aluminum, and ammonia. As salts of organic bases, the invention includes, for example, trimethylamine, triethylamine, pyridine, picoline, ethanolamine, diethanolamine, triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

The term "protected" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

Prodrugs, as used in the context of the instant invention, includes those derivatives of the instant compounds which undergo in vivo metabolic biotransformation, by enzymatic or nonenzymatic processes, such as hydrolysis, to form a compound of the invention. Prodrugs can be employed to improve pharmaceutical or biological properties, as for example solubility, melting point, stability and related physicochemical properties, absorption, pharmacodynamics and other delivery-related properties.

The instant invention provides potent and specific agonists of MC4-R that are low molecular weight small molecules. In accordance with one aspect of the invention, the invention provides compounds of formula IA, IB, and IC. Compounds of the invention further include prodrugs of compounds of formula IA, IB, and IC, pharmaceutically acceptable salts thereof, stereoisomers thereof, tautomers thereof, hydrates thereof, hydrides thereof, or solvates thereof.

Compounds of formula IA, IB, and IC have the following structure.

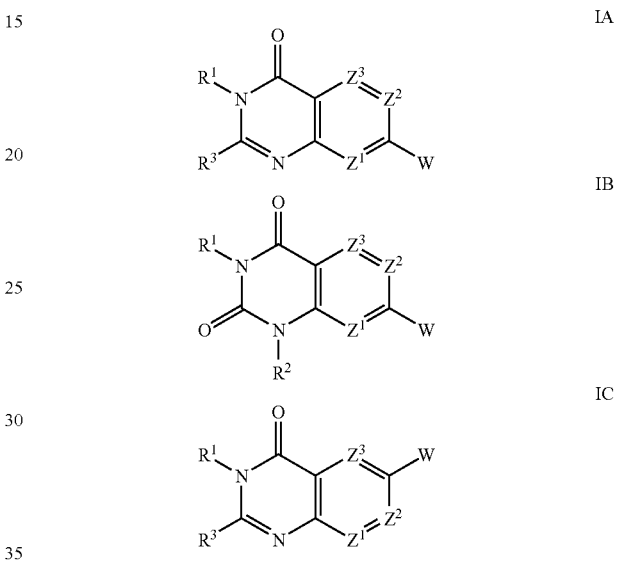

In compounds of formula IA, IB, and IC, $Z^1$ is selected from the group consisting of $CR^4$ and N. In some embodiments of the compounds of formula IA, IB, and IC, $Z^1$ is a $CR^4$ group whereas in other embodiments, $Z^1$ is a N.

In compounds of formula IA, IB, and IC, $Z^2$ is selected from the group consisting of $CR^5$ and N. In some embodiments of the compounds of formula IA, IB, and IC, $Z^2$ is a $CR^5$ group whereas in other embodiments, $Z^2$ is a N.

In compounds of formula IA, IB, and IC, $Z^3$ is selected from the group consisting of $CR^6$ and N. In some embodiments of the compounds of formula IA, IB, and IC, $Z^3$ is a $CR^6$ group whereas in other embodiments, $Z^3$ is a N.

In some embodiments of compounds of formula IA, IB, and IC, $Z^1$ is a $CR^4$ group, $Z^2$ is a $CR^5$ group, and $Z^3$ is a $CR^6$ group. Thus, in some embodiments of compounds of formula IA, IB, and IC, the ring that includes $Z^1$, $Z^2$, and $Z^3$ may be a carbocyclic aromatic ring. In some embodiments of compounds of formula IA, IB, and IC, where $Z^1$ is a $CR^4$ group, $Z^2$ is a $CR^5$ group, and $Z^3$ is a $CR^6$ group, at least one of $R^4$, $R^5$, or $R^6$ is a halogen such as Cl or F. In other such embodiments, at least one of $R^4$, $R^5$, or $R^6$ is a F.

In some embodiments of compounds of formula IA, IB, and IC, at least one of $Z^1$, $Z^2$, or $Z^3$ is a N.

In compounds of formula IA, IB, and IC, $R^1$ is selected from the group consisting of substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups. In some embodiments of the compounds of formula IA, IB, and IC, $R^1$ is a 2,4-disubstituted phenylethyl group. In other embodiments of the compounds of formula IA, IB, and IC, $R^1$ is selected from 2,4-dihalophenylethyl and 2,4-dialkylphenylethyl groups. In still other embodiments of the compounds of formula IA, IB, and IC, $R^1$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl) ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups.

In some embodiments, the invention provides compounds of formula IA, IB and IC in which $R^1$ is a substituted or unsubstituted alkenyl group such as a substituted or unsubstituted allyl group or a substituted or unsubstituted vinyl group.

In compounds of formula IB, $R^2$ is selected from the group consisting of H, and substituted and unsubstituted alkyl, alkenyl, alkynyl, cycloalkyl, aryl, heteroaryl, heterocyclyl, arylalkyl, heteroarylalkyl, cycloalkylalkyl, alkylcarbonyl, and arylcarbonyl groups. In some embodiments of the compounds of formula IB, $R^2$ is H.

In compounds of formula IA and IC, $R^3$ is selected from the group consisting of H, and substituted and unsubstituted arylalkyl, heteroarylalkyl, alkoxy, alkylamino, dialkylamino, aryl, heteroaryl, heterocyclyl, cycloalkyl, heterocyclylalkyl, cycloalkylalkyl, alkenyl, alkynyl, and alkyl groups. In some embodiments of the compounds of formula IA and IC, $R^3$ is H. In still further embodiments, the invention provides compounds of formula IA and IC in which $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups.

In compounds of formula IA, IB, and IC, $R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups. In some embodiments of compounds of formula IA, IB, and IC, $R^4$, $R^5$, and $R^6$ are selected from H or a halogen such as Cl or F. In other embodiments of compounds of formula IA, IB, and IC, at least one of $R^4$, $R^5$, or $R^6$ is a F whereas in other embodiments of compounds of formula IA, IB, and IC, $R^4$, $R^5$, and $R^6$ are all H.

In compounds of formula IA, IB, and IC, W is a group of formula IIA or IIB having the following structure.

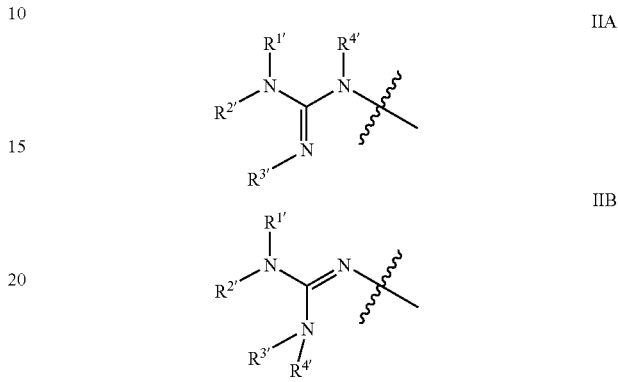

In compounds of formula IA, IB, and IC, $R^{1'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, and $R^{2'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups. In compounds of formula IA, IB, and IC, $R^{1'}$ and $R^{2'}$, together with the nitrogen atom to which they are both bound, may alternatively form a substituted or unsubstituted heterocyclyl or heteroaryl group. In one embodiment of compounds of formula IA, IB, and IC, $R^{1'}$ is H and $R^{2'}$ is selected from the group consisting of substituted and unsubstituted alkyl, arylalkyl, and heteroarylalkyl groups. In still other embodiments of compounds of formula IA, IB, and IC, $R^{1'}$ is H and $R^{2'}$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still further embodiments of compounds of formula IA, IB, and IC, $R^{1'}$ and $R^{2'}$ may be the same or different and are each independently selected from the group consisting of substituted and unsubstituted alkyl, arylalkyl, and heteroarylalkyl groups. In yet other embodiments of compounds of formula IA, IB, and IC, $R^{1'}$ and $R^{2'}$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still other embodiments of compounds of formula IA, IB, and IC, $R^{1'}$ and $R^{2'}$, together with the nitrogen to which they are bound, form a substituted or unsubstituted heterocyclyl group. In other embodiments of compounds of formula IA, IB, and IC, $R^{1'}$ and $R^{2'}$, together with the nitrogen to which they are bound, form a substituted or unsubstituted saturated heterocyclyl group comprising at least one heteroatom selected from the group consisting of O, S, and N, in addition to the nitrogen atom to which $R^{1'}$ and $R^{2'}$ are bound. In another embodiment of compounds of formula IA, IB, and IC, $R^{1'}$ and $R^{2'}$, together with the nitrogen atom to which they are bound, form a substituted or unsubstituted heterocyclyl ring containing at least two nitrogen atoms. In still another embodiment of compounds of formula IA, IB, and IC, $R^{1'}$ and $R^{2'}$, together with the nitrogen atom to which they are bound, form a substituted or unsubstituted heterocyclyl ring containing at least one oxygen atom and one nitrogen atom. In yet other embodiments of compounds of formula IA, IB, and IC, $R^{1'}$ and $R^{2'}$, together with the nitrogen to which they are bound, form a substituted or unsubstituted piperazino, morpholino, pyrrolidino, piperidino, homopiperazino, or azepino group. In still further embodiments of compounds of formula IA, IB, and IC, $R^{1'}$ and $R^{2'}$, together with the nitrogen to which they are bound, form a piperazino group optionally substituted by one or two alkyl groups or in one embodiment by one or two methyl groups.

In compounds of formula IA, IB, and IC, $R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups. In one embodiment of compounds of formula IA, IB, and IC, $R^{3'}$ is selected from the group consisting of substituted and unsubstituted cycloalkyl, polycyclic cycloalkyl, alkenyl, alkyl, and aryl groups. In still other embodiments of compounds of formula IA, IB, and IC, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of compounds of formula IA, IB, and IC, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups. By way of nonlimiting example, suitable $R^{3'}$ cycloalkyl, cyclohexyl, and polycyclic cycloalkyl groups that include fluorine, include, but are not limited to, the following structures:

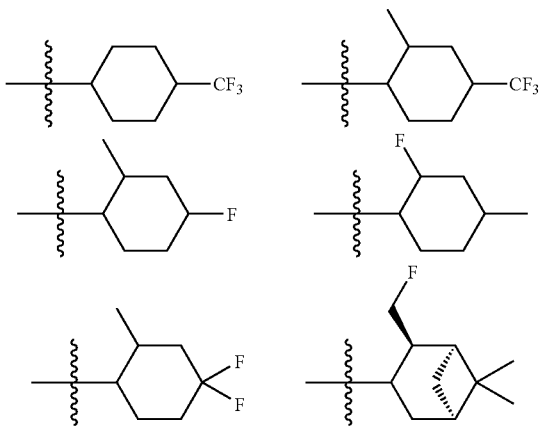

In compounds of formula IA, IB, and IC, $R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups. In one embodiment of compounds of formula IA, IB, and IC, $R^{4'}$ is H.

In one embodiment of the compounds of formula IA, the compounds of formula IA are selected from the group consisting of compounds having the formula IIIA, IIIB, IIIC, IIID, IIIE, IIIF, and IIIG such as shown below where $R^1$, W, $R^{1'}$, $R^{2'}$, $R^{3'}$, and $R^{4'}$ have the same values as those described above with respect to the compounds and various embodiments of formula IA, IB, and IC.

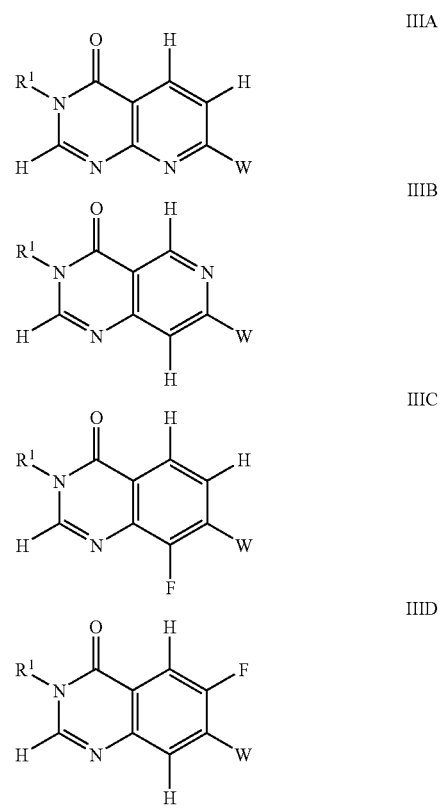

-continued

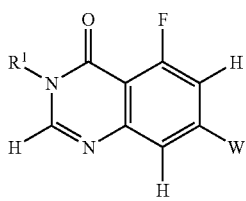
IIIE

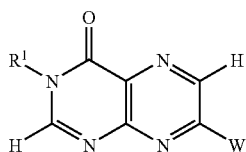
IIIF

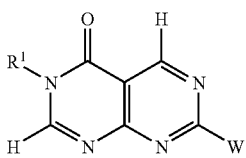
IIIG

In an embodiment of the compounds of formula IB, the compounds of formula IB are selected from the group consisting of compounds having the formula IVA and IVB such as shown below where $R^1$, W, $R^{1'}$, $R^{2'}$, $R^{3'}$, and $R^{4'}$ have the same values as those described above with respect to the compounds of formula IA, IB, and IC.

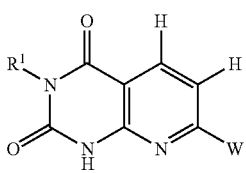
IVA

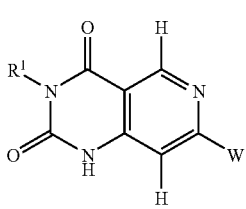
IVB

The instant invention provides a second group of compounds that are potent and specific agonists of MC4-R that are low molecular weight small molecules. Thus, in accordance with one aspect of the invention, the invention provides a second group of compounds of formula IA and IC. Compounds of the invention further include prodrugs of compounds of formula IA and IC, pharmaceutically acceptable salts thereof, stereoisomers thereof, tautomers thereof, hydrates thereof, hydrides thereof, or solvates thereof.

Compounds of formula IA and IC have the following structure.

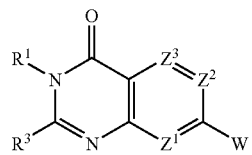
IA

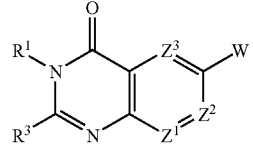
IC

In the second group of compounds of formula IA and IC, $Z^1$ is selected from the group consisting of $CR^4$ and N. In some embodiments of the second compounds of formula IA and IC, $Z^1$ is a $CR^4$ group whereas in other embodiments, $Z^1$ is a N.

In the second group of compounds of formula IA and IC, $Z^2$ is selected from the group consisting of $CR^5$ and N. In some embodiments of the second group of compounds of formula IA and IC, $Z^2$ is a $CR^5$ group whereas in other embodiments, $Z^2$ is a N.

In the second group of compounds of formula IA and IC, $Z^3$ is selected from the group consisting of $CR^6$ and N. In some embodiments of the second group of compounds of formula IA and IC, $Z^3$ is a $CR^6$ group whereas in other embodiments, $Z^3$ is a N.

In some embodiments of the second group of compounds of formula IA and IC, $Z^1$ is a $CR^4$ group, $Z^2$ is a $CR^5$ group, and $Z^3$ is a $CR^6$ group. Thus, in some embodiments of the second group of compounds of formula IA and IC, the ring that includes $Z^1$, $Z^2$, and $Z^3$ may be a carbocyclic aromatic ring. In some embodiments of the second group of compounds of formula IA and IC, where $Z^1$ is a $CR^4$ group, $Z^2$ is a $CR^5$ group, and $Z^3$ is a $CR^6$ group, at least one of $R^4$, $R^5$, or $R^6$ is a halogen such as Cl or F. In other such embodiments, at least one of $R^4$, $R^5$, or $R^6$ is a F.

In some embodiments of the second group of compounds of formula IA and IC, at least one of $Z^1$, $Z^2$, or $Z^3$ is a N.

In the second group of compounds of formula IA and IC, $R^1$ is selected from the group consisting of H, substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups. In some embodiments of the second group of compounds of formula IA and IC, $R^1$ is a 2,4-disubstituted phenylethyl group. In other embodiments of the second group of compounds of formula IA and IC, $R^1$ is selected from 2,4-dihalophenylethyl and 2,4-dialkylphenylethyl groups. In still other embodiments of the second group of compounds of formula IA and IC, $R^1$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4- fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some embodiments of the second group of compounds, $R^1$ is a H or is an alkyl group having from one to eight carbon atoms. In some such embodiments, $R^1$ is H whereas in other such embodiments, $R^1$ is a methyl, ethyl, or propyl group. In some such embodiments, $R^1$ is a methyl group.

In still further embodiments, the invention provides compounds of formula IA and IC in which $R^1$ is a substituted or unsubstituted alkenyl group such as a substituted or unsubstituted allyl group or a substituted or unsubstituted vinyl group.

In the second group of compounds of formula IA and IC, $R^3$ is selected from the group consisting of substituted and unsubstituted arylalkyl, heteroarylalkyl, alkoxy, alkoxyalkyl, aryloxyalkyl, alkylamino, dialkylamino, aryl, heteroaryl, heterocyclyl, cycloalkyl, heterocyclylalkyl, cycloalkylalkyl, alkenyl, alkynyl, alkyl groups, and —C(=NH)-heterocyclyl groups, and groups of formula -L$R^7$. In some embodiments of the second group of compounds of formula IA and IC, $R^3$ is a 2,4-disubstituted phenylethyl group. In other embodiments of the second group of compounds of formula IA and IC, $R^3$ is selected from 2,4-dihalophenylethyl and 2,4-dialkylphenylethyl groups. In still other embodiments of the second group of compounds of formula IA and IC, $R^3$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some embodiments of the second group of compounds, $R^3$ has any of the values described in this paragraph, and $R^1$ is H or is a substituted or unsubstituted alkyl group. In some such embodiments, $R^1$ is H.

In some aspects of the invention of compounds of the second group of potent and specific agonists of MC4-R, the invention further provides compounds of formula IA and IC in which $R^3$ is a substituted or unsubstituted alkyl group such as a substituted or unsubstituted aryloxyalkyl group or a substituted or unsubstituted heteroaryloxyalkyl group. In some such embodiments, $R^3$ is a substituted or unsubstituted aryloxymethyl group. In some such embodiments, of the second group of compounds of formula IA and IC, $R^3$ is selected from the group consisting of —CH$_2$—O-aryl groups where the aryl group is substituted with one or more halogen group such as with one or more Cl or F. In some such embodiments, the aryl group is additionally substituted with an alkoxy group such as a methoxy or ethoxy group. In some embodiments of the second group of compounds of formula IA and IC, $R^3$ is a —CH$_2$—O-aryl group where the aryl group is selected from the group consisting of 2,4-difluorophenyl, 4-fluorophenyl, 2-fluorophenyl, 2-fluoro-4-methoxyphenyl, 2,4-dichlorophenyl, 4-chlorophenyl, 2-chlorophenyl, and 2-chloro-4-methoxyphenyl groups. In other embodiments of the second group of compounds of formula IA and IC, $R^3$ is a heterocyclylalkyl group. In some other embodiments, of compounds of formula IA and IC, $R^3$ is a substituted or unsubstituted arylalkoxyalkyl group or a heteroarylalkoxyalkyl group.

In some aspects of the invention of compounds of the second group of potent and specific agonists of MC4-R, the invention further provides compounds of formula IA and IC in which $R^3$ is a substituted or unsubstituted heterocyclylalkyl group. In some such embodiments, $R^3$ is a substituted or unsubstituted heterocyclylmethyl group. In some such embodiments, the heterocyclyl group is selected from the group consisting of substituted and unsubstituted 1H-tetrazole, piperazine, piperidine, imidazole, and morpholine groups. In some such embodiments, $R^3$ is a —CH$_2$-heterocyclyl group where the heterocyclyl group is a 1H-tetrazole, an imidazole, an N-methylpiperazine, a 4-hydroxypiperidine, a 3-hydroxypiperidine, or a morpholine. In still other embodiments of the second group of compounds of formula IA and IC, $R^3$ is a heterocyclyl group. In some embodiments of the second group of compounds of formula IA and IC, $R^3$ is a substituted or unsubstituted piperazinyl group such as an N-methylpiperazinyl group, is a substituted or unsubstituted pyridine group, is a substituted or unsubstituted tetrazole group, is a substituted or unsubstituted cycloalkyl group such as a 4-methylcyclohexyl group, or is a substituted or unsubstituted phenyl group. In yet other embodiments of the second group of compounds of formula IA and IC, $R^3$ is an alkoxyalkyl group such as a methoxyalkyl group or an ethoxyalkyl group. In some such embodiments, $R^3$ is a an alkoxyalkyl group such as an alkoxymethyl group such as a methoxymethyl group.

In some other embodiments of the second group of compounds of formula IA and IC, $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups In some embodiments of the second group of compounds of formula IA and IC, $R^1$ is an arylalkyl group such as those described above for $R^3$. In some such embodiments, $R^1$ is a substituted or unsubstituted phenylethyl group and $R^3$ is an alkyl group such as a methyl group. In other embodiments of the second group of compounds, $R^1$ is an alkyl group such as a methyl group and $R^3$ is selected from substituted aryloxyalkyl groups, phenylaminoalkyl groups or groups of -$LR^7$ where $R^7$ is a group formula IIC.

In the second group of compounds of formula IA and IC, $R^4$, $R^5$, and $R^6$ are independently selected from the group consisting of H, Cl, I, F, Br, OH, $NH_2$, CN, $NO_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups. In some embodiments of the second group of compounds of formula IA and IC, $R^4$, $R^5$, and $R^6$ are selected from H or a halogen such as Cl or F. In other embodiments of the second group of compounds of formula IA and IC, at least one of $R^4$, $R^5$, or $R^6$ is a F whereas in other embodiments of the second group of compounds of formula IA and IC, $R^4$, $R^5$, and $R^6$ are all H.

In the second group of compounds of formula IA and IC, W is a group of formula IIA or IIB having the following structure.

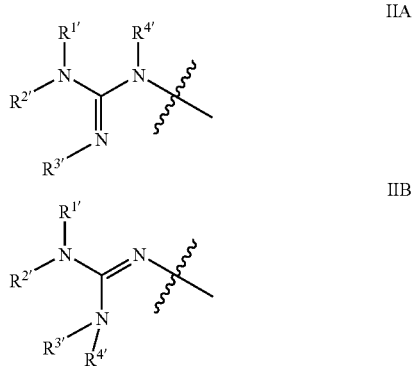

In the second group of compounds of formula IA and IC, $R^{1'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, and $R^{2'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups. In the second group of compounds of formula IA and IC, $R^{1'}$ and $R^{2'}$, together with the nitrogen atom to which they are both bound, may alternatively form a substituted or unsubstituted heterocyclyl or heteroaryl group. In one embodiment of the second group of compounds of formula IA and IC, $R^{1'}$ is H and $R^{2'}$ is selected from the group consisting of substituted and unsubstituted alkyl, arylalkyl, and heteroarylalkyl groups. In still other embodiments of the second group of compounds of formula IA and IC, $R^{1'}$ is H and $R^{2'}$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still further embodiments of second group of compounds of formula IA and IC, $R^{1'}$ and $R^{2'}$ may be the same or different and are each independently selected from the group consisting of substituted and unsubstituted alkyl, arylalkyl, and heteroarylalkyl groups. In yet other embodiments of the second group of compounds of formula IA and IC, $R^{1'}$ and $R^{2'}$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still other embodiments of the second group of compounds of formula IA and IC, $R^{1'}$ and $R^{2'}$, together with the nitrogen to which they are bound, form a substituted or unsubstituted heterocyclyl group. In other embodiments of the second group of compounds of formula IA and IC, $R^{1'}$ and $R^{2'}$, together with the nitrogen to which they are bound, form a substituted or unsubstituted saturated heterocyclyl group comprising at least one heteroatom selected from the group consisting of O, S, and N, in addition to the nitrogen atom to which $R^{1'}$ and $R^{2'}$ are bound. In another embodiment of the second group of compounds of formula IA and IC, $R^{1'}$ and $R^{2'}$, together with the nitrogen atom to which they are bound, form a substituted or unsubstituted heterocyclyl ring containing at least two nitrogen atoms. In still another embodiment of the second group of compounds of formula IA and IC, $R^{1'}$ and $R^{2'}$, together with the nitrogen atom to which they are bound, form a substituted or unsubstituted heterocyclyl ring containing at least one oxygen atom and one nitrogen atom. In yet other embodiments of the second group of compounds of formula IA and IC, $R^{1'}$ and $R^{2'}$, together with the nitrogen to which they are bound, form a substituted or unsubstituted piperazino, morpholino, pyrrolidino, piperidino, homopiperazino, or azepino group. In still further embodiments of the second group of compounds of formula IA and IC, $R^{1'}$ and $R^{2'}$, together with the nitrogen to which they are bound, form a piperazino group optionally substituted by one or two alkyl groups or in one embodiment by one or two methyl groups.

In the second group of compounds of formula IA and IC, $R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups. In one embodiment of the second group of compounds of formula IA, and IC, $R^{3'}$ is selected from the group consisting of substituted and unsubstituted cycloalkyl, polycyclic cycloalkyl, alkenyl, alkyl, and aryl groups. In still other embodiments of the second group of compounds of formula IA and IC, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of the second group of compounds of formula IA and IC, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl (polycyclic cycloalkyl), fluoromethyl(polycyclic cycloalkyl), and fluoro(polycyclic cycloalkyl) groups. By way of nonlimiting example, suitable $R^{3'}$ cycloalkyl, cyclohexyl, and polycyclic cycloalkyl groups that include fluorine, include, but are not limited to, the structures set forth above with respect to the first group of compounds of formula IA, IB, and IC.

In the second group of compounds of formula IA and IC, $R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups. In one embodiment of the second group of compounds of formula IA and IC, $R^{4'}$ is H.

In the second group of compounds of formula IA and IC, L is selected from the group consisting of a covalent bond, —CH$_2$—, —O—, —S—, and —NH—.

In the second group of compounds of formula IA and IC, $R^7$ is selected from the group consisting of substituted and unsubstituted arylaminoalkyl, aryl, and aryloxyalkyl groups or is selected from a group of formula IIC;

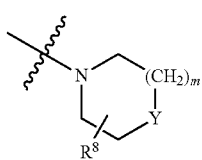

IIC

In the second group of compounds of formula IA and IC, Y is selected from the group consisting of CH$_2$, O, S, and NR$^9$ where R$^9$. In some embodiments, Y is an NR$^9$ group and in some such embodiments, m is 1. In some such embodiments, R$^9$ is an alkyl group such as a methyl group or is a H.

In the second group of compounds of formula IA and IC, $R^8$ is selected from the group consisting of H, a halogen, hydroxyl, carboxylic acid, and substituted or unsubstituted alkyl, amino, alkylamino, dialkylamino, alkylaminoalkyl, heterocyclyl, alkoxy, carbonyl, and aminocarbonyl groups.

In the second group of compounds of formula IA and IC, m is an integer selected from the group consisting of 0, 1, and 2. In some embodiments, m is 1.

The instant invention provides a third group of compounds that are potent and specific agonists of MC4-R that are low molecular weight small molecules. Thus, in accordance with one aspect of the invention, the invention provides a third group of compounds of formula ID. Compounds of the invention further include prodrugs of compounds of formula ID, pharmaceutically acceptable salts thereof, stereoisomers thereof, tautomers thereof, hydrates thereof, hydrides thereof, or solvates thereof.

Compounds of formula ID have the following structure.

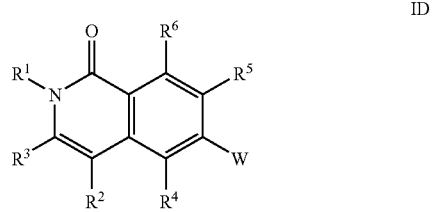

ID

In some embodiments of the third group of compounds of formula ID, at least one of $R^4$, $R^5$, or $R^6$ is a halogen such as Cl or F. In other such embodiments, at least one of $R^4$, $R^5$, or $R^6$ is a F.

In the third group of compounds of formula ID, $R^1$ is selected from the group consisting of H, substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups. In some embodiments of the third group of compounds of formula ID, $R^1$ is a 2,4-disubstituted phenylethyl group. In other embodiments of the third group of compounds of formula ID, $R^1$ is selected from 2,4-dihalophenylethyl and 2,4-dialkylphenylethyl groups. In still other embodiments of the third group of compounds of formula ID, $R^1$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some embodiments of the third group of compounds, $R^1$ is a H or is an alkyl group having from one to eight carbon atoms. In some such embodiments, $R^1$ is H whereas in other such embodiments, $R^1$ is a methyl, ethyl, or propyl group. In some such embodiments, $R^1$ is a methyl group.

In still further embodiments, the invention provides compounds of formula ID in which $R^1$ is a substituted or unsubstituted alkenyl group such as a substituted or unsubstituted allyl group or a substituted or unsubstituted vinyl group.

In the third group of compounds of formula ID, $R^2$ and $R^3$ are independently selected from the group consisting of substituted and unsubstituted arylalkyl, heteroarylalkyl, alkoxy, alkoxyalkyl, aryloxyalkyl, alkylamino, dialkylamino, aryl, heteroaryl, heterocyclyl, cycloalkyl, heterocyclylalkyl, cycloalkylalkyl, alkenyl, alkynyl, alkyl groups, and —C(=NH)-heterocyclyl groups, and groups of formula -L$R^7$. In some embodiments of the third group of compounds of formula ID, $R^2$ is —H or a substituted or unsubstituted alkyl group. In some embodiments of the third group of compounds of formula ID, $R^3$ is a 2,4-disubstituted phenylethyl group. In other embodiments of the third group of compounds of formula ID, $R^3$ is selected from 2,4-dihalophenylethyl and 2,4-dialkylphenylethyl groups. In still other embodiments of the third group of compounds of formula ID, $R^3$ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some embodiments of the third group of compounds, $R^3$ has any of the values described in this paragraph, and $R^1$ or $R^2$ is H or is a substituted or unsubstituted alkyl group. In some such embodiments, $R^1$ is H. In other such embodiments, $R^2$ is H.

In some aspects of the invention of compounds of the third group of potent and specific agonists of MC4-R, the invention further provides compounds of formula ID in which $R^3$ is a substituted or unsubstituted alkyl group such as a substituted or unsubstituted aryloxyalkyl group or a substituted or unsubstituted heteroaryloxyalkyl group. In some such embodiments, $R^3$ is a substituted or unsubstituted aryloxymethyl group. In some such embodiments, of the third group of compounds of formula ID, $R^3$ is selected from the group consisting of —CH$_2$—O-aryl groups where the aryl group is substituted with one or more halogen group such as with one or more Cl or F. In some such embodiments, the aryl group is additionally substituted with an alkoxy group such as a methoxy or ethoxy group. In some embodiments of the third group of compounds of formula ID, $R^3$ is a —CH$_2$—O-aryl group where the aryl group is selected from the group consisting of 2,4-difluorophenyl, 4-fluorophenyl, 2-fluorophenyl, 2-fluoro-4-methoxyphenyl, 2,4-dichlorophenyl, 4-chlorophenyl, 2-chlorophenyl, and 2-chloro-4-methoxyphenyl groups. In other embodiments of the third group of compounds of formula ID, $R^3$ is a heterocyclylalkyl group. In some other embodiments, of compounds of formula ID, $R^3$ is a substituted or unsubstituted arylalkoxyalkyl group or a heteroarylalkoxyalkyl group.

In some aspects of the invention of compounds of the third group of potent and specific agonists of MC4-R, the invention further provides compounds of formula ID in which $R^3$ is a substituted or unsubstituted heterocyclylalkyl group. In some such embodiments, $R^3$ is a substituted or unsubstituted heterocyclylmethyl group. In some such embodiments, the heterocyclyl group is selected from the group consisting of substituted and unsubstituted 1H-tetrazole, piperazine, piperidine, imidazole, and morpholine groups. In some such embodiments, $R^3$ is a —CH$_2$-heterocyclyl group where the heterocyclyl group is a 1H-tetrazole, an imidazole, an N-methylpiperazine, a 4-hydroxypiperidine, a 3-hydroxypiperidine, or a morpholine. In still other embodiments of the third group of compounds of formula ID, $R^3$ is a heterocyclyl group. In some embodiments of the third group of compounds of formula ID, $R^3$ is a substituted or unsubstituted piperazinyl group such as an N-methylpiperazinyl group, is a substituted or unsubstituted pyridine group, is a substituted or unsubstituted tetrazole group, is a substituted or unsubstituted cycloalkyl group such as a 4-methylcyclohexyl group, or is a substituted or unsubstituted phenyl group. In yet other embodiments of the third group of compounds of formula ID, $R^3$ is an alkoxyalkyl group such as a methoxyalkyl group or an ethoxyalkyl group. In some such embodiments, $R^3$ is a an alkoxyalkyl group such as an alkoxymethyl group such as a methoxymethyl group.

In some other embodiments of the third group of compounds of formula ID, $R^3$ is a substituted or unsubstituted alkenyl group such as a substituted or unsubstituted allyl group or a substituted or unsubstituted vinyl group. In some embodiments, the invention provides compounds in which $R^3$ is a substituted or unsubstituted heteroaryl group, heterocyclyl group, alkylamino group, or cycloalkyl amino group. In some such embodiments, $R^3$ is selected from substituted and unsubstituted 2-pyridyl, 3-pyridyl, 4-pyridyl, pyrazine, morpholinyl, piperazinyl, and cyclopropylamino groups.

In some embodiments of the third group of compounds of formula ID, $R^1$ is an arylalkyl group such as those described above for $R^3$. In some such embodiments, $R^1$ is a substituted or unsubstituted phenylethyl group and $R^3$ is an alkyl group such as a methyl group. In other embodiments of the third group of compounds, $R^1$ is an alkyl group such as a methyl group and $R^3$ is selected from substituted aryloxyalkyl groups, phenylaminoalkyl groups or groups of L$R^7$ where $R^7$ is a group formula IIC.

In the third group of compounds of formula ID, $R^4$, $R^5$, and $R^6$ are independently selected from the group consisting of H, Cl, I, F, Br, OH, NH$_2$, CN, NO$_2$, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups. In some embodiments of the third group of compounds of formula ID, $R^4$, $R^5$, and $R^6$ are selected from H or a halogen such as Cl or F. In other embodiments of the third group of compounds of formula ID, at least one of $R^4$, $R^5$, or $R^6$ is a F whereas in other embodiments of the third group of compounds of formula ID, $R^4$, $R^5$, and $R^6$ are all H.

In the third group of compounds of formula ID, W is a group of formula IIA or IIB having the following structure.

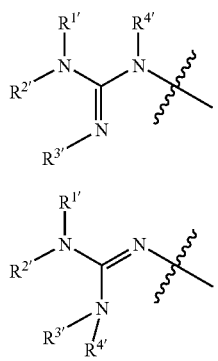

In the third group of compounds of formula ID, $R^{1'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, and $R^{2'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups. In the third group of compounds of formula ID, $R^{1'}$ and $R^{2'}$, together with the nitrogen atom to which they are both bound, may alternatively form a substituted or unsubstituted heterocyclyl or heteroaryl group. In one embodiment of the third group of compounds of formula ID, $R^{1'}$ is H and $R^{2'}$ is selected from the group consisting of substituted and unsubstituted alkyl, arylalkyl, and heteroarylalkyl groups. In still other embodiments of the third group of compounds of formula ID, $R^{1'}$ is H and $R^{2'}$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still further embodiments of third group of compounds of formula ID, $R^{1'}$ and $R^{2'}$ may be the same or different and are each independently selected from the group consisting of substituted and unsubstituted alkyl, arylalkyl, and heteroarylalkyl groups. In yet other embodiments of the third group of compounds of formula ID, $R^{1'}$ and $R^{2'}$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still other embodiments of the third group of compounds of formula ID, $R^{1'}$ and $R^{2'}$, together with the nitrogen to which they are bound, form a substituted or unsubstituted heterocyclyl group. In other embodiments of the third group of compounds of formula ID, $R^{1'}$ and $R^{2'}$, together with the nitrogen to which they are bound, form a substituted or unsubstituted saturated heterocyclyl group comprising at least one heteroatom selected from the group consisting of O, S, and N, in addition to the nitrogen atom to which $R^{1'}$ and $R^{2'}$ are bound. In another embodiment of the third group of compounds of formula ID, $R^{1'}$ and $R^{2'}$, together with the nitrogen atom to which they are bound, form a substituted or unsubstituted heterocyclyl ring containing at least two nitrogen atoms. In still another embodiment of the third group of compounds of formula ID, $R^{1'}$ and $R^{2'}$, together with the nitrogen atom to which they are bound, form a substituted or unsubstituted heterocyclyl ring containing at least one oxygen atom and one nitrogen atom. In yet other embodiments of the third group of compounds of formula ID, $R^{1'}$ and $R^{2'}$, together with the nitrogen to which they are bound, form a substituted or unsubstituted piperazino, morpholino, pyrrolidino, piperidino, homopiperazino, or azepino group. In still further embodiments of the third group of compounds of formula ID, $R^{1'}$ and $R^{2'}$, together with the nitrogen to which they are bound, form a piperazino group optionally substituted by one or two alkyl groups or in one embodiment by one or two methyl groups.

In the third group of compounds of formula ID, $R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups. In one embodiment of the third group of compounds of formula IA, and IC, $R^{3'}$ is selected from the group consisting of substituted and unsubstituted cycloalkyl, polycyclic cycloalkyl, alkenyl, alkyl, and aryl groups. In still other embodiments of the third group of compounds of formula ID, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of the third group of compounds of formula ID, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups. By way of nonlimiting example, suitable $R^{3'}$ cycloalkyl, cyclohexyl, and polycyclic cycloalkyl groups that include fluorine, include, but are not limited to, the structures set forth above with respect to the first group of compounds of formula IA, IB, and IC.

In the third group of compounds of formula ID, $R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups. In one embodiment of the third group of compounds of formula ID, $R^{4'}$ is H.

In the third group of compounds of formula ID, L is selected from the group consisting of a covalent bond, —CH₂—, —O—, —S—, and —NH—.

In the third group of compounds of formula ID, R⁷ is selected from the group consisting of substituted and unsubstituted arylaminoalkyl, aryl, and aryloxyalkyl groups or is selected from a group of formula IIC;

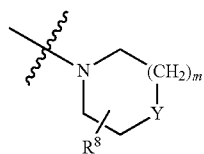

In the third group of compounds of formula ID, Y is selected from the group consisting of CH₂, O, S, and NR⁹ where R⁹. In some embodiments, Y is an NR⁹ group and in some such embodiments, m is 1. In some such embodiments, R⁹ is an alkyl group such as a methyl group or is a H.

In the third group of compounds of formula ID, R⁸ is selected from the group consisting of H, a halogen, hydroxyl, carboxylic acid, and substituted or unsubstituted alkyl, amino, alkylamino, dialkylamino, alkylaminoalkyl, heterocyclyl, alkoxy, carbonyl, and aminocarbonyl groups.

In the third group of compounds of formula ID, m is an integer selected from the group consisting of 0, 1, and 2. In some embodiments, m is 1.

The instant invention provides a fourth group of compounds that are potent and specific agonists of MC4-R that are low molecular weight small molecules. Thus, in accordance with one aspect of the invention, the invention provides a fourth group of compounds of formula IE. Compounds of the invention further include prodrugs of compounds of formula IE, pharmaceutically acceptable salts thereof, stereoisomers thereof, tautomers thereof, hydrates thereof, hydrides thereof, or solvates thereof.

Compounds of formula IE have the following structure.

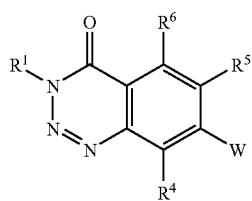

In some embodiments of the fourth group of compounds of formula IE at least one of R⁴, R⁵, or R⁶ is a halogen such as Cl or F. In other such embodiments, at least one of R⁴, R⁵, or R⁶ is a F.

In the fourth group of compounds of formula IE, R¹ is selected from the group consisting of H, substituted and unsubstituted arylalkyl, heteroarylalkyl, aryl, heteroaryl, heterocyclyl, cycloalkyl, heterocyclylalkyl, cycloalkylalkyl, alkenyl, alkynyl, and alkyl groups. In some embodiments of the fourth group of compounds of formula IE, R¹ is a 2,4-disubstituted phenylethyl group. In other embodiments of the fourth group of compounds of formula IE, R¹ is selected from 2,4-dihalophenylethyl and 2,4-dialkylphenylethyl groups. In still other embodiments of the fourth group of compounds of formula IE, R¹ is selected from the group that includes phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, cyclohexenylethyl, 2-methoxyphenylethyl, 2-chlorophenylethyl, 2-fluorophenylethyl, 3-methoxyphenylethyl, 3-fluorophenylethyl, thienylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2-trifluoromethyl-4-fluorophenylethyl, 2,4-difluorophenylethyl, 2,4-dimethylphenylethyl, 2,4-dimethoxyphenylethyl, (2-pyridyl)ethyl, (3-pyridyl)ethyl, (4-pyridyl)ethyl, (pyridyl)(hydroxymethyl)ethyl, (phenyl)(hydroxymethyl)ethyl, substituted and unsubstituted (heteroaryl)(hydroxymethyl)ethyl, substituted and unsubstituted (aryl)(hydroxymethyl)ethyl groups, substituted and unsubstituted (aryl)(alkoxymethyl)ethyl, substituted and unsubstituted (aryl)(aryloxymethyl)ethyl, substituted and unsubstituted (aryl)(arylalkoxymethyl)ethyl, substituted and unsubstituted (aryl)(heteroaryloxymethyl)ethyl, substituted and unsubstituted (aryl)(heterocyclyloxymethyl)ethyl, substituted and unsubstituted (heteroaryl)(alkoxymethyl)ethyl, substituted and unsubstituted (heteroaryl)(aryloxymethyl)ethyl, substituted and unsubstituted (heteroaryl)(arylalkoxymethyl)ethyl, substituted and unsubstituted (heteroaryl)(heteroaryloxymethyl)ethyl, and substituted and unsubstituted (heteroaryl)(heterocyclyloxymethyl)ethyl groups. In some embodiments of the fourth group of compounds, R¹ is a H or is an alkyl group having from one to eight carbon atoms. In some such embodiments, R¹ is H whereas in other such embodiments, R¹ is a methyl, ethyl, or propyl group. In some such embodiments, R¹ is a methyl group.

In still further embodiments, the invention provides compounds of formula IE in which R¹ is a substituted or unsubstituted alkenyl group such as a substituted or unsubstituted allyl group or a substituted or unsubstituted vinyl group.

In the fourth group of compounds of formula IE, R¹ is H or is a substituted or unsubstituted alkyl group. In some such embodiments, R¹ is H.

In the fourth group of compounds of formula IE, R⁴, R⁵, and R⁶ are independently selected from the group consisting of H, Cl, I, F, Br, OH, NH₂, CN, NO₂, and substituted and unsubstituted alkoxy, alkyl, alkenyl, alkynyl, alkylamino, dialkylamino, cycloalkyl, heterocyclylamino, heteroarylamino, aminocarbonyl, alkylaminocarbonyl, dialkylaminocarbonyl, cycloalkylaminocarbonyl, arylaminocarbonyl, heterocyclylaminocarbonyl, and heteroarylaminocarbonyl groups. In some embodiments of the fourth group of compounds of formula IE, R⁴, R⁵, and R⁶ are selected from H or a halogen such as Cl or F. In other embodiments of the fourth group of compounds of formula IE, at least one of R⁴, R⁵, or R⁶ is a F whereas in other embodiments of the fourth group of compounds of formula IE, R⁴, R⁵, and R⁶ are all H.

In the fourth group of compounds of formula IE, W is a group of formula IIA or IIB having the following structure.

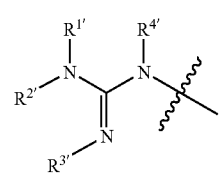

-continued

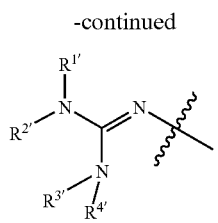

IIB

In the fourth group of compounds of formula IE, $R^{1'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups, and $R^{2'}$ is selected from the group consisting of H, and substituted and unsubstituted alkyl, alkenyl, alkynyl, cycloalkyl, aryl, heteroaryl, heterocyclyl, arylalkyl, heteroarylalkyl, and cycloalkylalkyl groups. In the fourth group of compounds of formula IE, $R^{1'}$ and $R^{2'}$, together with the nitrogen atom to which they are both bound, may alternatively form a substituted or unsubstituted heterocyclyl or heteroaryl group. In one embodiment of the fourth group of compounds of formula IE, $R^{1'}$ is H and $R^{2'}$ is selected from the group consisting of substituted and unsubstituted alkyl, arylalkyl, and heteroarylalkyl groups. In still other embodiments of the fourth group of compounds of formula IE, $R^{1'}$ is H and $R^{2'}$ is selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still further embodiments of fourth group of compounds of formula IE, $R^{1'}$ and $R^{2'}$ may be the same or different and are each independently selected from the group consisting of substituted and unsubstituted alkyl, arylalkyl, and heteroarylalkyl groups. In yet other embodiments of the fourth group of compounds of formula IE, $R^{1'}$ and $R^{2'}$ may be the same or different and are each independently selected from the group consisting of substituted and unsubstituted dialkylaminoethyl, 4-ethylbenzyl, 3-chlorobenzyl, 2,4-dichlorobenzyl, 3-methylbenzyl, benzyl, 4-fluorobenzyl, 3-methoxybenzyl, 2-chlorobenzyl, and thiophene groups. In still other embodiments of the fourth group of compounds of formula IE, $R^{1'}$ and $R^{2'}$ together with the nitrogen to which they are bound, form a substituted or unsubstituted heterocyclyl group. In other embodiments of the fourth group of compounds of formula IE, $R^{1'}$ and $R^{2'}$, together with the nitrogen to which they are bound, form a substituted or unsubstituted saturated heterocyclyl group comprising at least one heteroatom selected from the group consisting of O, S, and N, in addition to the nitrogen atom to which $R^{1'}$ and $R^{2'}$ are bound. In another embodiment of the fourth group of compounds of formula IE, $R^{1'}$ and $R^{2'}$, together with the nitrogen atom to which they are bound, form a substituted or unsubstituted heterocyclyl ring containing at least two nitrogen atoms. In still another embodiment of the fourth group of compounds of formula IE, $R^{1'}$ and $R^{2'}$, together with the nitrogen atom to which they are bound, form a substituted or unsubstituted heterocyclyl ring containing at least one oxygen atom and one nitrogen atom. In yet other embodiments of the fourth group of compounds of formula IE, $R^{1'}$ and $R^{2'}$, together with the nitrogen to which they are bound, form a substituted or unsubstituted piperazino, morpholino, pyrrolidino, piperidino, homopiperazino, or azepino group. In still further embodiments of the fourth group of compounds of formula IE, $R^{1'}$ and $R^{2'}$, together with the nitrogen to which they are bound, form a piperazino group optionally substituted by one or two alkyl groups or in one embodiment by one or two methyl groups.

In the fourth group of compounds of formula IE, $R^{3'}$ is selected from the group consisting of H, and substituted and unsubstituted aryl, alkyl, alkenyl, alkynyl, cycloalkyl, heteroaryl, heterocyclyl, heterocyclylalkyl, arylalkyl, heteroarylalkyl, and cycloalkylalkyl groups. In one embodiment of the fourth group of compounds of formula IA, and IC, $R^{3'}$ is selected from the group consisting of substituted and unsubstituted cycloalkyl, polycyclic cycloalkyl, alkenyl, alkyl, and aryl groups. In still other embodiments of the fourth group of compounds of formula IE, $R^{3'}$ is selected from the group consisting of substituted and unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, cyclohexylmethyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, fluoroalkylcycloalkyl, trifluoromethylcycloalkyl, cyclopentyl, cycloheptyl, cyclohexenyl, isopropyl, n-butyl, cyclooctyl, 2-arylcyclohexyl, 2-phenylcyclohexyl, 2-arylalkylcyclohexyl, 2-benzylcyclohexyl, 4-phenylcyclohexyl, adamantyl, isocamphenyl, carenyl, 7,7-dialkylnorbornyl, bornyl, norbornyl, and decalinyl groups. In still other embodiments of the fourth group of compounds of formula IE, $R^{3'}$ is selected from the group consisting of substituted and unsubstituted cyclohexyl, 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, cyclohexenyl, 3,3,5-trimethylcyclohexyl, 4-t-butylcyclohexyl, cyclohexylmethyl, isopinocampheyl, 7,7-dimethylnorbornyl, 4-isopropylcyclohexyl, 3-methylcycloheptyl groups, 2-fluoro-4-methylcyclohexyl, 4-fluoro-2-methylcyclohexyl, 4,4-difluoro-2-methylcyclohexyl, 4-trifluoromethylcyclohexyl, 2-methyl-4-trifluoromethylcyclohexyl, 2-fluoromethylcyclohexyl, trifluoromethyl(polycyclic cycloalkyl), fluoromethyl(polycyclic cycloalkyl), and fluoro(polycyclic cycloalkyl) groups. By way of nonlimiting example, suitable $R^{3'}$ cycloalkyl, cyclohexyl, and polycyclic cycloalkyl groups that include fluorine, include, but are not limited to, the structures set forth above with respect to the first group of compounds of formula IA, IB, and IC.

In the fourth group of compounds of formula IE, $R^{4'}$ is selected from the group consisting of H, and substituted and unsubstituted alkyl, alkenyl, alkynyl, cycloalkyl, heterocyclylalkyl, cycloalkylalkyl, aryl, heteroaryl, heterocyclyl, arylalkyl, and heteroarylalkyl groups. In one embodiment of the fourth group of compounds of formula IE, $R^{4'}$ is H.

In some embodiments of any of the compounds of the invention which includes a W group of formula IIA or IIB where $R^{1'}$ and $R^{2'}$ join together with the nitrogen to which they are bound to form a heterocyclic group, the heterocyclic group is substituted with a —CN group, an —OH group, a —CF$_3$ group, a —CH$_2$F group, a —CHF$_2$ group, a —CH$_2$CN group, a —CH2OH group, a —CH$_2$O-alkyl group, or a cycloalkyl group such as a cyclopropyl group. In some such compounds, the heterocyclic compound is a piperidine or a piperazine. In some such compounds, $R^{1'}$ and $R^{2'}$ join together with the nitrogen to which they are bound to form a piperazine in which the N atom in the piperazine ring which is not part of the guanidine group is substituted with a —C≡N group, an —OH group, a —CH$_2$CN group, or a cycloalkyl group. In some compounds in which $R^{1'}$ and $R^{2'}$ join together with the nitrogen to which they are bound to form a heterocyclic ring, the heterocycle is a bicyclic structure that includes a spiro-center such that the heterocyclic ring is part of a spirocyclic structure. In some compounds in which $R^{1'}$ and $R^{2'}$ join together with the nitrogen to which they are bound to form a heterocyclic ring, the heterocyclic ring is substituted such that a ring carbon atom of the heterocyclic ring is a carbonyl carbon or the carbon of the heterocyclic ring is replaced with a sulfur that is bonded to one or more oxygen atoms. For example, in some embodiments $R^{1'}$ and $R^{2'}$ join together with the nitrogen to which they are bound to form a piperazine ring in which one of the ring carbon atoms is a carbonyl carbon atom such that the piperazine compound is a lactam which may be further substituted, for example, with an alkyl group such as a methyl group.

There has also been provided, in accordance with another aspect of the invention, a composition such as a pharmaceutical formulation or medicament comprising a compound according to the instant invention and a pharmaceutically acceptable carrier. The invention further provides the use of the compounds of the invention in preparing a medicament such as a medicament for use in treating an MC4-R mediated disease. In some embodiments, such a disease is obesity or type II diabetes.

There has also been provided, in accordance with another aspect of the invention, a method of activating MC4-R in a subject, comprising administering to a subject in need thereof an effective amount of a compound or composition of the instant invention. In some embodiments, the compound or composition is administered to the subject intranasally. In some embodiments, the subject is human.

There has also been provided, in accordance with another aspect of the invention, a method of treating an MC4-R-mediated disease, comprising administering to a subject in need thereof, a compound or composition of the instant invention. In some embodiments, the compound or composition is administered to the subject intranasally. In some embodiments, the subject is human In one embodiment, a disease to be treated by those methods of the instant invention is obesity, or type I or type II diabetes.

In another embodiment, a condition to be treated by those methods of the instant invention is a condition associated with or a complication arising from obesity or type II diabetes.

In another embodiment, a condition to be treated by those methods of the instant invention is erectile dysfunction.

In another embodiment, a disease to be treated by those methods of the instant invention is polycystic ovary disease.

In another embodiment, a disease to be treated by those methods of the instant invention is Syndrome X.

The invention also includes tautomers of the instant compounds. The instant invention also includes prodrugs, pharmaceutically acceptable salts, stereoisomers, hydrates, hydrides, and solvates of these tautomers.

The instant compounds may exist as one or more stereoisomers. The various stereoisomers include enantiomers, diastereomers, atropisomers and geometric isomers. In some cases, one stereoisomer may be more active and/or may exhibit beneficial effects in comparison to other stereoisomer(s) or when separated from the other stereoisomer(s). However, it is well within the skill of the ordinary artisan to separate, and/or to selectively prepare said stereoisomers. Accordingly, "stereoisomers" of the instant invention necessarily includes mixtures of stereoisomers, individual stereoisomers, or optically active forms.

The instant invention also provides for compositions which may be prepared by mixing one or more compounds of the instant invention, or pharmaceutically acceptable salts or tautomers thereof, with pharmaceutically acceptable carriers, excipients, binders, diluents or the like, to treat or ameliorate a variety of disorders. Examples of such disorders include, but are not limited to obesity, erectile disorders, cardiovascular disorders, neuronal injuries or disorders, inflammation, fever, cognitive disorders, sexual behavior disorders. A therapeutically effective dose further refers to that amount of one or more compounds of the instant invention sufficient to result in amelioration of symptoms of the disorder. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by intranasal administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should hot be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, a thickeners, buffers, a sweeteners, flavoring agents or perfuming agents. Additionally, dyestuffs or pigments may be added for identification. Tablets and pills may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to, stabilizers, antimicrobial agents, antioxidants, pH modifiers, surfactants, bioavailability modifiers and combinations of these. Examples of intranasal formulations and methods of administration can be found in WO 01/41782, WO 00/33813, WO 91/97947, U.S. Pat. No. 6,180,603, and U.S. Pat. No. 5,624,898. A propellant for an aerosol formulation may include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

The formulations of the invention may be designed for to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations may be compressed into pellets or cylinders and implanted intramuscularly or subcutaneously as depot injections or as implants such as stents. Such implants may employ known inert materials such as silicones and biodegradable polymers.

A therapeutically effective dose refers to that amount of the compound that results in amelioration of symptoms. Specific dosages may be adjusted depending on conditions of disease, the age, body weight, general health conditions, sex, diet of the subject, dose intervals, administration routes, excretion rate, and combinations of drugs. Any of the above dosage forms containing effective amounts are well within the bounds of routine experimentation and therefore, well within the scope of the instant invention. A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

The present invention also provides methods of enhancing MC4-R activity in a human or non-human animal. The method comprises administering an effective amount of a compound, or composition, of the instant invention to said mammal or non-human animal. Effective amounts of the compounds of the instant invention include those amounts that activate MC4-R which are detectable, for example, by an assay described below in the illustrative Examples, or any other assay known by those skilled in the art that a detect signal transduction, in a biochemical pathway, through activation of G-protein coupled receptors, for example, by measuring an elevated cAMP level as compared to a control model. Accordingly, "activating" means the ability of a compound to initiate a detectable signal. Effective amounts may also include those amounts which alleviate symptoms of a MC4-R disorder treatable by activating MC4-R.

An MC4-R disorder, or MC4-R-mediated disease, which may be treated by those methods provided, include any biological disorder or disease in which MC4-R is implicated, or which inhibition of MC4-R potentiates a biochemical pathway that is defective in the disorder or disease state. Examples of such diseases are obesity, erectile disorders, cardiovascular disorders, neuronal injuries or disorders, inflammation, fever, cognitive disorders, type II diabetes, polycystic ovary disease, Syndrome X, complications from obesity and diabetes, and sexual behavior disorders. In a preferred embodiment, the instant invention provides compounds, compositions, and methods effective for reducing energy intake and body weight; reducing serum insulin and glucose levels; alleviating insulin resistance; and reducing serum levels of free fatty acids. Accordingly, the instant invention is particularly effective in treating those disorders or diseases associated with obesity or type II diabetes.

"Treating" within the context of the instant invention, therefore, means an alleviation of symptoms associated with a disorder or disease, or halt of further progression or worsening of those symptoms, or prevention or prophylaxis of the disease or disorder. For example, within the context of obesity, successful treatment may include an alleviation of symptoms or halting the progression of the disease, as measured by reduction in body weight, or a reduction in amount of food or energy intake. In this same vein, successful treatment of type I or type II diabetes may include an alleviation of symptoms or halting the progression of the disease, as measured by a decrease in serum glucose or insulin levels in, for example, hyperinsulinemic or hyperglycemic patients.

Compounds of formula IA may be readily synthesized as shown in Scheme 1a, the specifics of which are provided in the Examples section. As also explained in the Examples section, compounds of formula IIIC, IIID, and IIIE may be prepared using the methodology shown in Scheme 1b using an appropriately fluorine-substituted 4-nitroanthranilic acid in place of compound (b). Compounds of formula IC may be prepared using the methodology shown in Scheme 1a using an appropriately substituted 5-nitroanthranilic acid in place of 4-nitroanthranilic acid.

SCHEME 1a

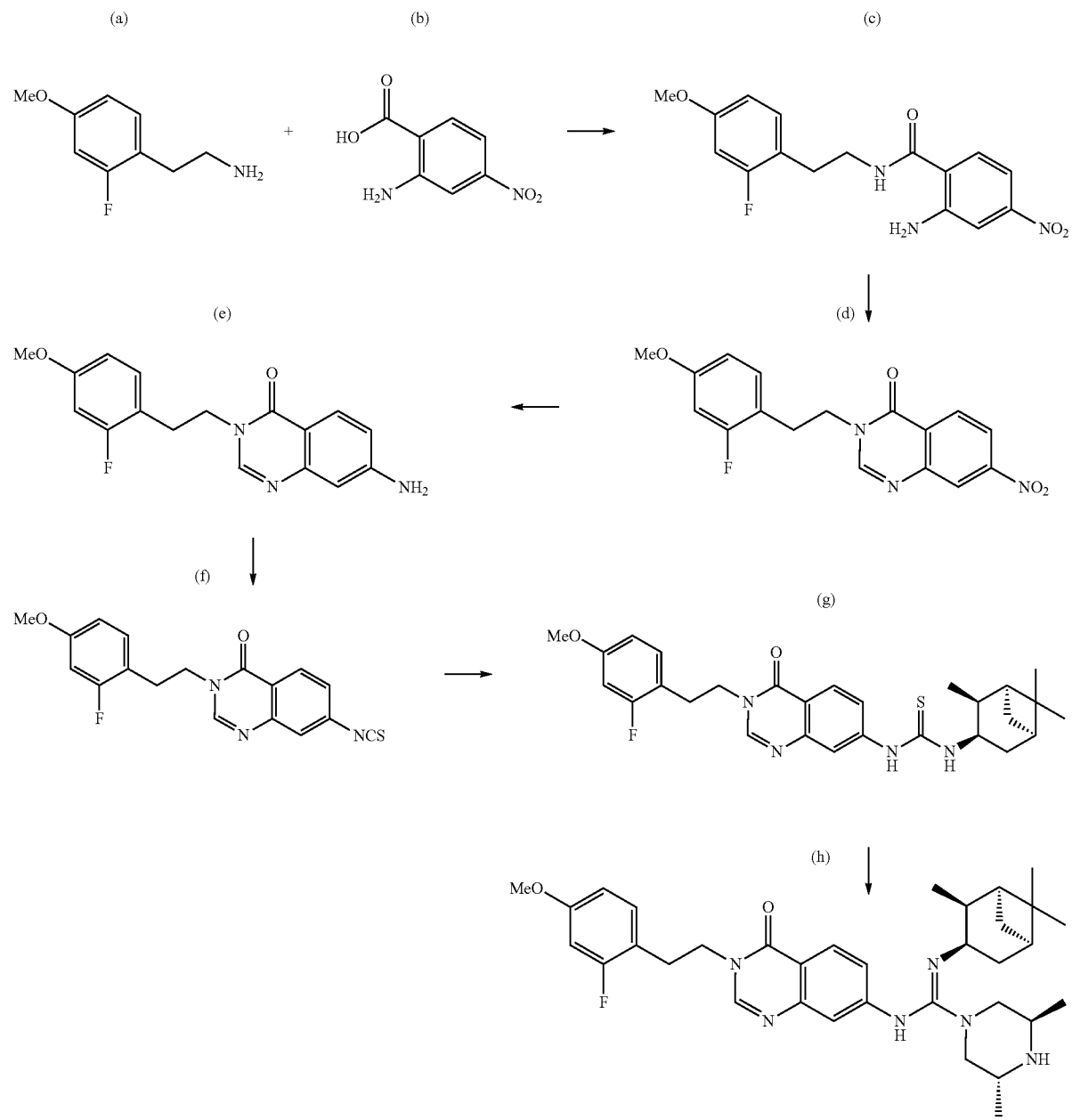

As explained in the Examples section, compounds of formula IIIA, IIIB, IIIF, and IIIG may be prepared using the methodology shown in Scheme 1b using an appropriately substituted pyridine, pyrazine, or pyrimidine carboxylic acid, for example 2-amino-6-azido-nicotinic acid, shown in (b). The conversion of compound (d) to (e), described in further detail in Procedure 1A, proceeds through the initial addition of trimethylphosphine to form a reactive iminophosphorane intermediate, followed by the addition of a substituted isocyanate (preferably by a substituted carbocycle isocyanate) to produce a carbodiimide, and finally formation of (e) occurs upon reaction with an amine (preferably a substituted piperazine).

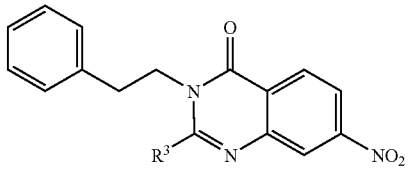

$R^3$ = H, Alkyl, Aryl, Arylalkyl, etc.

Scheme 1b

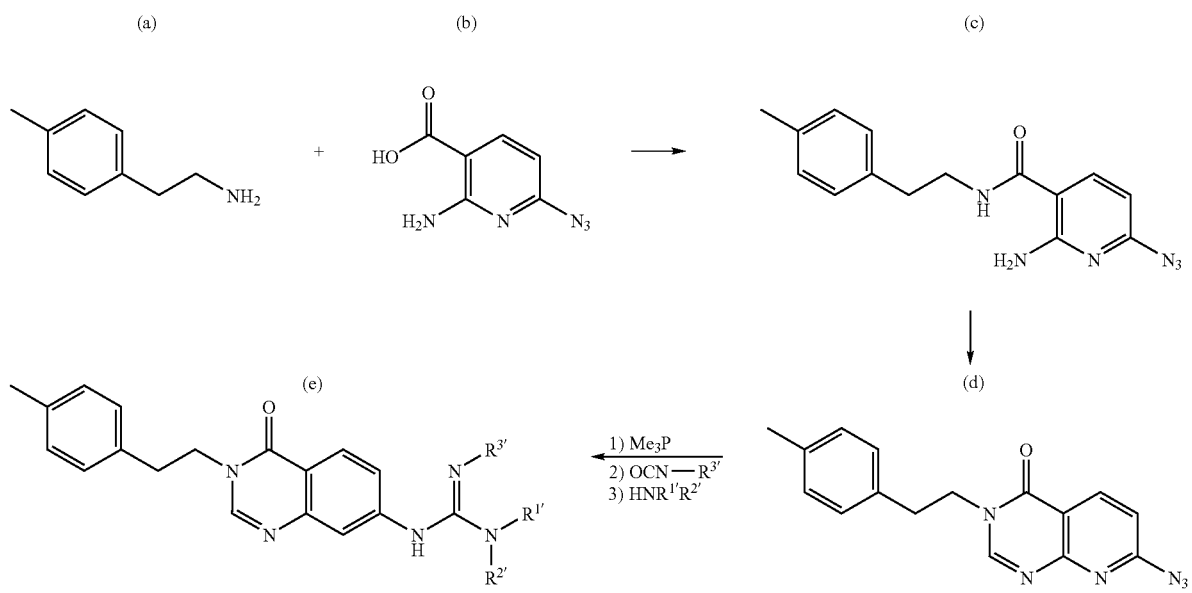

Compounds of formula IA may also be prepared using the general synthetic methodology set forth in Scheme 2a. This methodology is also suitable for preparing compounds of formula IC by using a benzoic acid with the nitro group in the correct position.

Scheme 2b shows an alternative route that may be used to prepare various compounds of formula IA.

SCHEME 2b

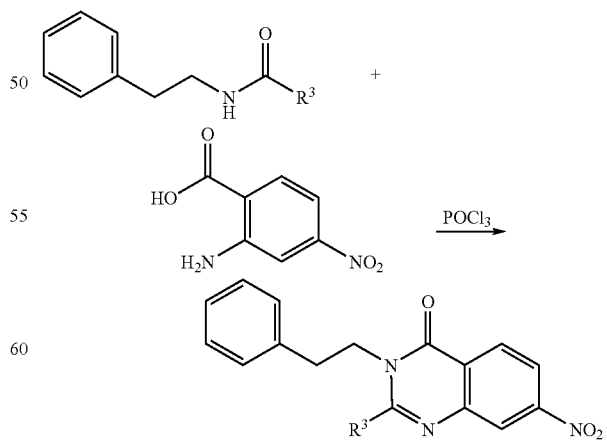

SCHEME 2a

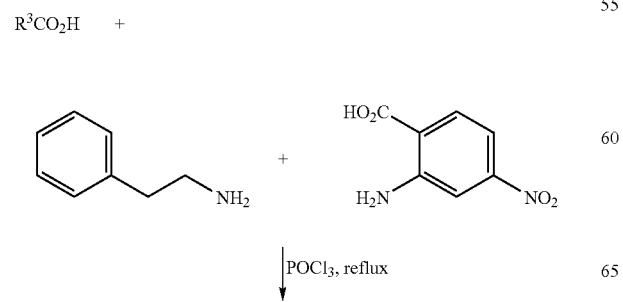

Scheme 2c shows an alternative route that may be used to prepare various compounds of formula IA. This route may also be used to prepare compound of formula IC if a starting material is used with a nitro group in the appropriate position as will be readily observed by those skilled in the art.

SCHEME 2c

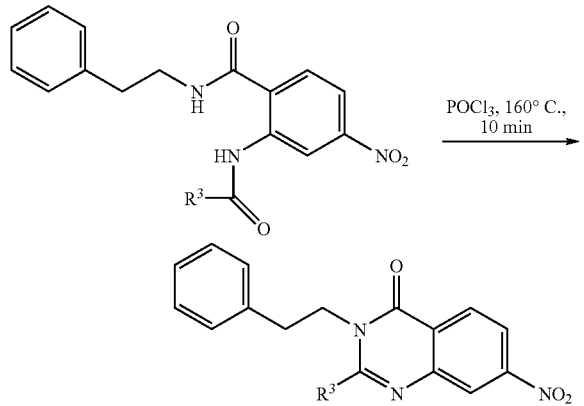

The invention provides various methods for synthesizing compounds of formula IA and IC, various intermediate compounds, and salts of the compounds and intermediate compounds. For example, a method for producing a compound having the formula VA is provided where $R^1$, $R^3$, $Z^1$, $Z^2$, $Z^3$, $R^4$, $R^5$, and $R^6$ have any of the values described above with respect to compounds of formula IA and embodiments of compounds of formula IA, and $Y^1$ is selected from the group consisting of $NO_2$, a protected amine group, a halogen such as Cl, F, Br, or I, an —NCS, and an $N_3$ group. In some embodiments of the method, $R^1$ is a substituted or unsubstituted arylalkyl group. In some embodiments of the method, $R^3$ is H. In some embodiments, $Y^1$ is selected from a F, $NO_2$, or an $N_3$ group. In some embodiments of the method, $R^1$ is a substituted or unsubstituted arylalkyl group, $R^3$ is H, and $Y^1$ is selected from a F, $NO_2$, or an $N_3$ group. In some such embodiments, $Z^1$, $Z^2$, and $Z^3$ are each carbon atoms and $R^4$, $R^5$, and $R^6$ are each H. Compounds of formula VA may be readily converted into compounds of formula IA as shown in Scheme 1a and the procedures set forth herein. Typically a compound of formula VA where $Y^1$ is a —NCS is reacted with a first amine and then is reacted with a second amine as described in Procedure 1a. Any of the amines defined by the $R^{1'}$, $R^{2'}$, and $R^{3'}$ of compounds of formula IA may be used. The versatility of this procedure allows a wide range of compounds of formula IA to be prepared where W is a guanidine group prepared from compounds of formula VA where $Y^1$ is a —NCS group. Another procedure that may be used to prepare compounds of formula IA from compounds of formula VA where $Y^1$ is an $N_3$ group is shown in Scheme 1b where nitrogen compounds with any of the $R^{1'}$, $R^{2'}$, and $R^{3'}$ groups of compounds of formula IA may be used.

VA

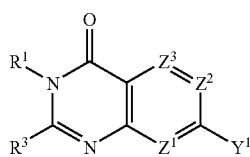

A method for preparing a compound of formula VA typically includes cyclizing a compound of formula VB by reacting it with an electrophilic carbon bearing an $R^3$ group such as a trialkyl orthoformate such as triethyl orthoformate, trimethyl orthoformate or the like where the $R^3$ is a H; Gold's Reagent; a substituted or unsubstituted alkanoyl halide such as acetyl chloride where $R^3$ is a methyl group; a substituted or unsubstituted alkanoic acid in the presence of an acid halide producing agent such as thionyl chloride, $POCl_3$, various phosphorous halides, and the like (e.g. an alkanoic acid of formula $R^3CO_2H$ in combination with $POCl_3$); a benzoyl chloride or an analogous heteroaryl acid chloride compound; or a substituted or unsubstituted benzoic acid or analogous heteroaryl carboxylic acid compound and an acid halide producing agent. The reaction provides the compound of formula VA. Compounds of formula VB have the following formula.

VB

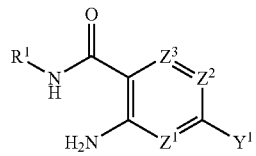

In compounds of formula VB, the variables may have any of the same values as described above with respect to compounds of formula VA. The method of forming a compound of formula VA may include reacting a compound of formula VC with an amine of formula $R^1$—$NH_2$ to produce the compound of formula VB using standard amide-forming procedures and where $R^1$ has any of the values of the compounds of formula VA and VB and the variables in the compound of VC have the values of compounds of formula VA and VB and $Y^2$ is a hydroxyl group or is an equivalent thereof. Compounds of formula VC have the following formula.

VC

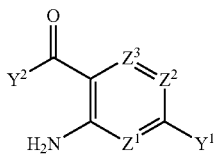

An alternative method for synthesizing compounds of formula IA is shown in Scheme 2a. Such a method generally includes reacting a compound of formula VC with an amine of formula $R^1$—$NH_2$ and an electrophilic carbon bearing an $R^3$ group such as a carboxylic acid of formula $R^3$—$CO_2H$. Compounds of formula IA may further be prepared according to the procedure in Scheme 2b by reacting a compound of formula VC with an amide of formula $R^1$—N(H)—C(=O)—$R^3$ in the presence of $POCl_3$ or an analogous compound.

Compounds of formula IE may be prepared from compounds of formula VB where $Y^1$ is a $NO_2$ group by reacting the compound with $NaNO_2$ as described in Method 6 to produce the analogs of compounds of formula VA which may then be converted to the compounds of formula IE from the compounds where $Y^1$ is an —$N_3$ group or is an —NCS group.

Compounds of formula IB may be produced from compounds of formula VB by reacting the compound of formula VB with phosgene or an equivalent thereof as described in Step 2 of Example 2 and subsequent conversion to the guanidine compounds from the $N_3$ or —NCS compounds using the standard procedures. Finally, compounds of formula ID may be prepared using the procedures described in Method 7 (Steps 1 and 2) using the fragments with the variables described above with respect to compounds of formula ID.

As noted above, the invention also provides methods for synthesizing compounds of formula IC, various intermediate compounds, and salts of the compounds and intermediate compounds. For example, a method for producing a compound having the formula VIA is provided where $R^1$, $R^3$, $Z^1$, $Z^2$, $Z^3$, $R^4$, $R^5$, and $R^6$ have any of the values described above with respect to compounds of formula IC and embodiments of compounds of formula IC, and $Y^1$ is selected from the group consisting of $NO_2$, a protected amine group, a halogen such as Cl, F, Br, or I, an —NCS, and an $N_3$ group. In some embodiments of the method, $R^1$ is a substituted or unsubstituted arylalkyl group. In some embodiments of the method, $R^3$ is H. In some embodiments, $Y^1$ is selected from a F, $NO_2$, or an $N_3$ group. In some embodiments of the method, $R^1$ is a substituted or unsubstituted arylalkyl group, $R^3$ is H, and $Y^1$ is selected from a F, $NO_2$, or an $N_3$ group. In some such embodiments, $Z^1$, $Z^2$, and $Z^3$ are each carbon atoms and $R^4$, $R^5$, and $R^6$ are each H. Compounds of formula VIA may be readily converted into compounds of formula IC as shown in Scheme 1a and the procedures set forth herein. Typically a compound of formula VIA where $Y^1$ is a —NCS is reacted with a first amine and then is reacted with a second amine as described in Procedure 1a. Any of the amines defined by the $R^{1'}$, $R^{2'}$, and $R^{3'}$ of compounds of formula IC may be used. The versatility of this procedure allows a wide range of compounds of formula IC to be prepared where W is a guanidine group prepared from compounds of formula VIA where $Y^1$ is a —NCS group. Another procedure that may be used to prepare compounds of formula IC from compounds of formula VIA where $Y^1$ is an $N_3$ group is shown in Scheme 1b where nitrogen compounds with any of the $R^{1'}$, $R^{2'}$, and $R^{3'}$ groups of compounds of formula IC may be used.

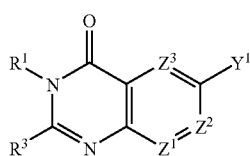

VIA

A method for preparing a compound of formula VIA typically includes cyclizing a compound of formula VIB by reacting it with an electrophilic carbon bearing an $R^3$ group such as a trialkyl orthoformate such as triethyl orthoformate, trimethyl orthoformate or the like where the $R^3$ is a H; Gold's Reagent; a substituted or unsubstituted alkanoyl halide such as acetyl chloride where $R^3$ is a methyl group; a substituted or unsubstituted alkanoic acid in the presence of an acid halide producing agent such as thionyl chloride, $POCl_3$, various phosphorous halides, and the like (e.g. an alkanoic acid of formula $R^3CO_2H$ in combination with $POCl_3$); a benzoyl chloride or an analogous heteroaryl acid chloride compound; or a substituted or unsubstituted benzoic acid or analogous heteroaryl carboxylic acid compound and an acid halide producing agent. The reaction provides the compound of formula VIA. Compounds of formula VIB have the following formula

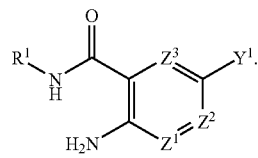

VIB

In compounds of formula VIB, the variable may have any of the same values as described above with respect to compounds of formula VIA. The method of forming a compound of formula VIA may include reacting a compound of formula VIC with an amine of formula $R^1$—$NH_2$ to produce the compound of formula VIB using standard amide-forming procedures and where $R^1$ has any of the values of the compounds of formula VIA and VIB and the variables in the compound of VIC have the values of compounds of formula VIA and VIB and $Y^2$ is a hydroxyl group or is an equivalent thereof. Compounds of formula VIC have the following formula.

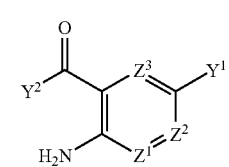

VIC

An alternative method for synthesizing compounds of formula IC is shown for analogous compounds of formula IA in Scheme 2a. Such a method generally includes reacting a compound of formula VIC with an amine of formula $R^1$—$NH_2$ and an electrophilic carbon bearing an $R^3$ group such as a carboxylic acid of formula $R^3$—$CO_2H$. Compounds of formula IC may further be prepared according to a procedure analogous to that shown in Scheme 2b by reacting a compound of formula VIC with an amide of formula $R^1$—N(H)—C(=O)—$R^3$ in the presence of $POCl_3$ or an analogous compound.

The present invention, thus generally described, will be understood more readily by reference to the following examples, which are provided by way of illustration and are not intended to be limiting of the present invention.

EXAMPLES

The following abbreviations and terms are used throughout the Examples:
Boc: t-Butyl carbamate protecting group
Celite®: Diatomaceous earth filter agent
DAST: (Dimethylamino)sulfur trifluoride
DCM: Dichloromethane
DIBAL: Diisobutylaluminum hydride
DIEA: N,N-Diisoproylethylamine
DMF: N,N-Dimethylformamide
DMSO: Dimethylsulfoxide
EDCI: 1-(3-Dimethylaminopropyl)-3-ethylcarbodiimide hydrochloride
EtOAc: Ethyl acetate
EtOH: Ethanol
Gold's Reagent: (Dimethylaminomethyleneaminomethylene)dimethyl ammonium chloride
HOBt: Hydroxybenzotriazole HPLC: High perfomance liquid chromatography
HCl: Hydrochloric acid
HBTU: O-Benzotriazol-1-yl-N,N,N',N'-tetramethyluronium hexafluorophosphate
KOH: Potassium hydroxide
LC: Liquid Chromatography
MS: Mass Spectroscopy
MeOH: Methanol
mL: Milliliter
NMP: 1-Methyl-2-pyrrolidinone
NMR: Nuclear magnetic resonance spectrocopy
TFA: Trifluoroacetic acid
THF: Tetrahydrofuran SYNTHESIS OF cis-4-FLUOROCYCLOHEXYLAMINE

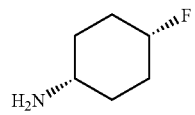

Step 1. Synthesis of trans-(t-butoxy)-N-(4-hydroxycyclohexyl)-carboxamide

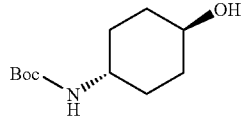

A suspension of trans-4-aminocyclohexanol (1 equivalent) in THF (0.1 M) was treated with (Boc)$_2$O (1 equivalent). The mixture was stirred at room temperature overnight, dissolved in chloroform, and washed with water to yield a solid that was used without further purification.

Step 2. Synthesis of cis-(t-butoxy)-N-(4-fluorocyclohexyl)carboxamide

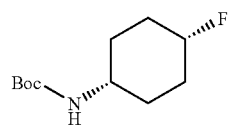

To a solution of (t-butoxy)-N-(4-hydroxycyclohexyl)carboxamide (1 equivalent) in CH$_2$Cl$_2$ (1 M) cooled to −78° C. was added dropwise a solution of DAST (1 equivalent) in CH$_2$Cl$_2$ (0.5 M). The mixture was stirred at −78° C. for 4 hours, and then allowed to rise to room temperature. The solution was poured into saturated NaHCO$_3$ and extracted with chloroform, dried, and evaporated. The resulting crude product was purified on silica gel, eluting with ethyl acetate/hexane 5:95.

Step 3. Synthesis of cis-4-fluorocyclohexylamine

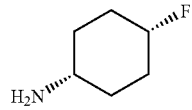

A solution of cis-(t-butoxy)-N-(4-fluorocyclohexyl)carboxamide (6.51 mmol) in CH$_2$Cl$_2$ (20 mL) was treated with TFA (10 mL) at room temperature. The reaction mixture was stirred for 2 hours, the solvent was removed in vacuo, and the crude product was dissolved in water and washed with chloroform. The acidic aqueous phase was cooled at 0° C. and made basic by the addition of solid KOH. The resulting mixture was extracted with CH$_2$Cl$_2$, dried and filtered, yielding the title compound which was used without further purification and as a 0.3 M solution in CH$_2$Cl$_2$.

SYNTHESIS OF 4,4-DIFLUOROCYCLOHEXYLAMINE

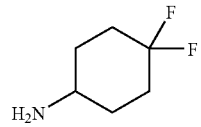

Step 1. Synthesis of N-(4,4-difluorocyclohexyl)(t-butoxy)carboxamide

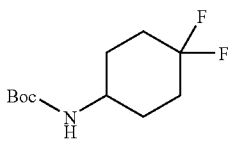

A solution of (t-butoxy)-N-(4-oxocyclohexyl)carboxamide (2.5 g, 11.7 mmol) in CH$_2$Cl$_2$ (45 mL) was treated with a solution of DAST (2.63 mL, 19.93 mmol) in CH$_2$Cl$_2$ (6 mL) at room temperature. EtOH (141 μl, 2.3 mmol) was added, and the mixture was stirred at room temperature overnight. The solution was poured into saturated NaHCO$_3$ and extracted with chloroform, dried, and evaporated to yield a 1:1 mixture of the title compound and (t-butoxy)-N-(4-fluoroclyclohex-3-enyl)carboxamide. This mixture was dissolved in CH$_2$Cl$_2$ (40 mL) and MeOH (14 mL) and cooled to −78° C. Ozone was bubbled into the solution for 50 minutes until it turned green and Me$_2$S was added (3 equivalents). The reaction mixture was allowed to warm to room temperature, chloroform was added and the organic phase was washed with water, dried, and evaporated to yield the title compound which was used without further purification.

Step 2. Synthesis of 4,4-difluorocyclohexylamine

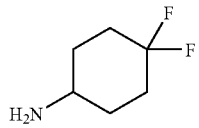

A solution of N-(4,4-difluorocyclohexyl)(t-butoxy)carboxamide (6.51 mmol) in CH$_2$Cl$_2$ (20 mL) was treated with TFA (10 mL) at room temperature. The reaction mixture was stirred for 2 hours, the solvent was removed in vacuo, and the crude product was dissolved in water and washed with chloroform. The acidic aqueous phase was cooled at 0° C. and made basic by the addition of solid KOH. The resulting mixture was extracted with CH$_2$Cl$_2$, dried, and filtered yielding the title compound which was used without further purification as a 0.3 M solution in CH$_2$Cl$_2$.

Procedure 1 Synthesis of 6-fluoro analog of 7-azidoquinazoline-4-one (1)

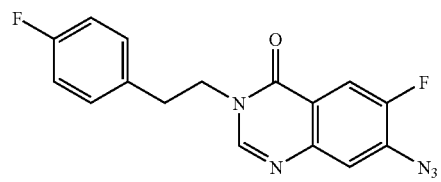

Step 1: Synthesis of (2-amino-4,5-difluorophenyl)-N-[2-(4-fluorophenyl)ethyl]carboxamide

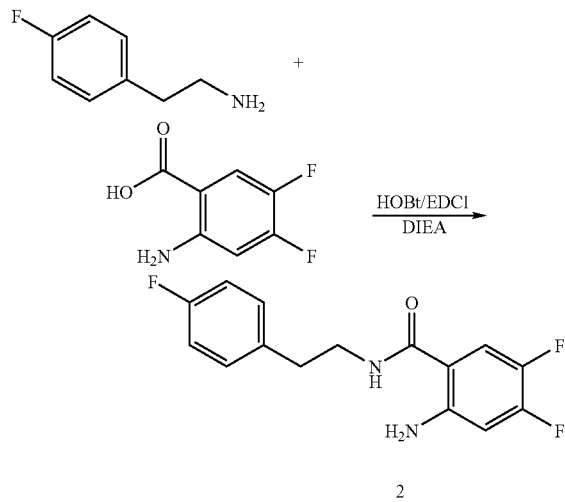

To a stirred solution of 4,5-difluoro anthranilic acid (2.0 g, 11.6 mmol) in anhydrous THF (30 mL) was added hydroxybenzotriazole hydrate (HOBt) (1.56 g, 11.6 mmol), diisopropylethyl amine (2.01 mL, 11.6 mmol), and 4-fluorophenylethyl amine (1.52 mL, 11.6 mmol). After all of the HOBt had completely dissolved, EDCI (2.21 g, 11.6 mmol) was added and the resulting orange solution was stirred at room temperature for 16 hours. The solvent was removed, and the residue was chromatographed on silica eluting with 15% EtOAc in hexanes giving the desired benzamide (2) as white crystals (3.07 g, 10.4 mmol, 90%).

Step 2: Synthesis of 6,7-difluoro-3-[2-(4-fluorophenyl)ethyl]-3-hydroquinazolin-4-one

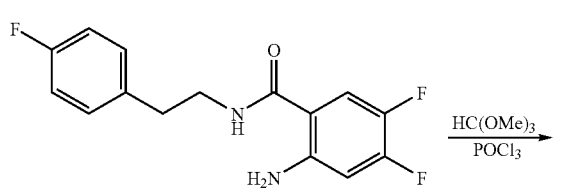

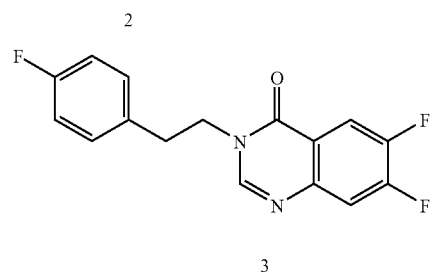

The starting benzamide (2) was dissolved in trimethyl orthoformate (20 mL) and heated at 120° C. under a stream of nitrogen for 3 hours. The solution was cooled, and the solvent was removed by rotary evaporation. The residue was triturated with hexanes, and the solids collected by filtration, washed with hexanes, and dried on the pump. The formamide intermediate was isolated as a white solid and confirmed by NMR. This intermediate was suspended in POCl$_3$ (10 mL) and heated to 140° C. for 3 minutes. The reaction was cooled, poured over crushed ice, made slightly alkaline with saturated sodium bicarbonate solution, and extracted with EtOAc. The organic layer was collected and dried over magnesium sulfate. Product (3) was isolated as a white solid (1.94 g, 6.38 mmol, 75% for 2 steps).

Step 3: Synthesis of 7-(azadiazomvinyl)-6-fluoro-3-[2-(4-fluorophenyl)ethyl]-3-hydroquinazolin-4-one

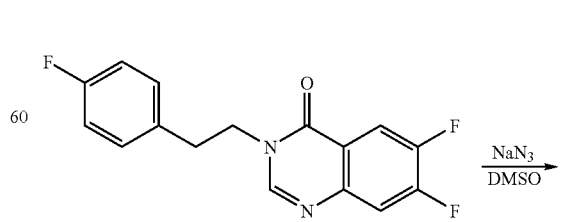

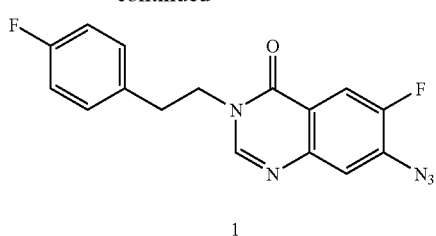

Difluoroquinazoline (3) (1.46 g, 4.6 mmol) was dissolved in DMSO (10 mL), and sodium azide (3 g, 46.0 mmol) was added. The resulting mixture was heated to 70° C. with stirring for 4 hours. The reaction was monitored by NMR. The reaction was cooled and diluted with water, and the resulting precipitate collected by filtration and washed with water. The solid was dissolved in methylene chloride and dried (MgSO$_4$) in order to remove trace water. Product (1) was isolated as an off-white solid (1.43 g, 4.37 mmol, 95%).

Following the formation of compound 1, final guanidino quinazilinones were formed following the synthetic method described below (Procedure 1A):

Procedure 1A

To a solution of (1) (1 equivalent) in THF was added trimethylphosphine (1.5 equivalents), and the mixture was stirred at room temperature for 10 minutes. To the iminophosphorane solution was added (1S,2S,3S,5R)-2,6,6-trimethyl-bicyclo[3.1.1]hept-3-yl isocyanate (1.6 equivalents). The solution was heated at 70° C. overnight. To half of the carboimide solution was added a THF solution of (6S,2R)-2,6-dimethylpiperazine (2 equivalents). After being heated at 70° C. for 2 hours, the residue was subjected to HPLC purification to give the guanidine product as its TFA salt.

The 2-fluoro-4-methoxy, 2,4-difluoro and 2,4-dichloro analogs were synthesized via the same pathway described above. Compounds of the group synthesized via the pathway described above include Examples 42, 44, and 45.

Example 1

Synthesis of (3R,5S)-N-(3-{2-[2-fluoro-4-(methyloxy)-phenyl]ethyl}-4-oxo-3,4-dihydroquinazolin-7-yl)-3,5-dimethyl-N'-[(1S,2S,5R)-2,6,6-trimethylbicyclo[3.1.1]hept-3-yl]piperazine-1-carboximidamide

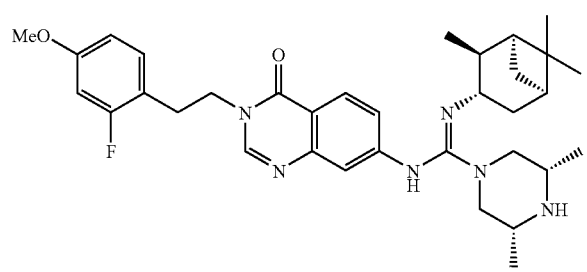

Step 1. Synthesis of (c): 2-amino-N-[2-(2-fluoro-4-methoxy-phenyl)-ethyl]-4-nitro-benzamide

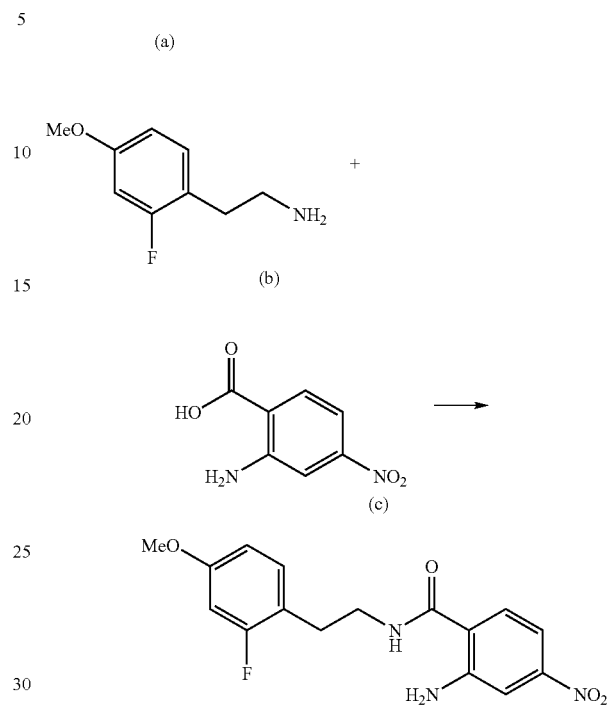

2-Fluoro-4-methoxyphenylethylamine ((a): 1 equivalent), 4-nitroanthranilic acid ((b): 1 equivalent), HBTU (1.5 equivalents), and dry THF (0.5 M in (a)) were added to a dry round bottom flask. The mixture was allowed to stir for 10 hours at room temperature. The reaction was then dry loaded onto silica gel and purified via flash chromatography using hexanes/ethyl acetate. The pure fractions were combined and concentrated in vacuo to yield the product ((c): 2-amino-N-[2-(2-fluoro-4-methoxy-phenyl)-ethyl]-4-nitro-benzamide) as a pure solid.

Step 2. Synthesis of (d): 3-[2-(2-fluoro-4-methoxy-phenyl)-ethyl]-7-nitro-3H-quinazolin-4-one

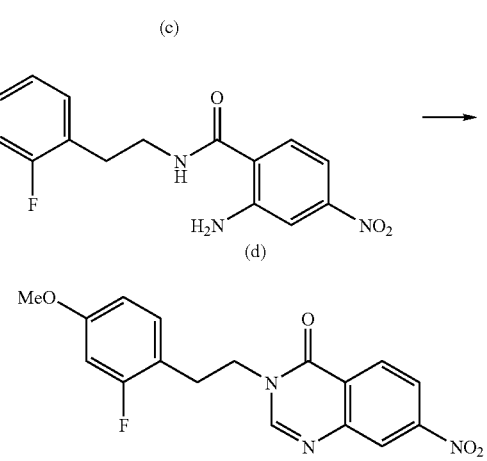

The pure product ((c): 1 equivalent) of Step 1, Gold's reagent, and dioxane (0.5 M in (c)) were added to a dry round bottom flask, fitted with a condenser, and heated to reflux for 16 hours. Once complete product conversion was verified by LC/MS, acetic acid (1 equivalent) and sodium acetate (1 equivalent) were added to the reaction. The subsequent mixture was heated to reflux for 3 hours. Then, the reaction was concentrated in vacuo, taken up in ethyl acetate, and washed with water. After the organic layer was isolated, the aqueous layer was extracted with two more portions of ethyl acetate. The organic layers were then combined, dried over sodium sulfate, filtered through a cotton plug, and concentrated. The crude product mixture was purified via flash chromatography using a mixture of $CH_2Cl_2$/MeOH. The pure fractions were combined and concentrated in vacuo to yield the pure product ((d): 3-[2-(2-fluoro-4-methoxy-phenyl)-ethyl]-7-nitro-3H-quinazolin-4-one) as a pure solid.

Step 3. Synthesis of (e): 7-amino-3-[2-(2-fluoro-4-methoxy-phenyl)-ethyl]-3H-quinazolin-4-one

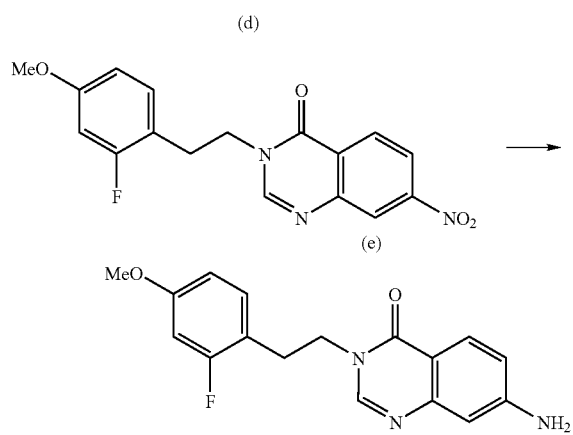

To a solution of (d), prepared as described in Step 2, in MeOH (0.25 M in (d)) was added 10% Pd/C (0.1 equivalents). The mixture was sealed with a septum and degassed with nitrogen for 10 minutes. Hydrogen was then bubbled through the solution for 20 minutes. Once reaction completion was verified by LC/MS, the reaction was degassed with nitrogen for 10 minutes. The mixture was filtered through Celite® and concentrated in vacuo to yield the product ((e): 7-amino-3-[2-(2-fluoro-4-methoxy-phenyl)-ethyl]-3H-quinazolin-4-one). The product was used in the next reaction without further purification.

Step 4. Synthesis of (f): 3-[2-(2-fluoro-4-methoxy-phenyl)ethyl]-7-isothiocyanato-3H-quinazolin-4-one

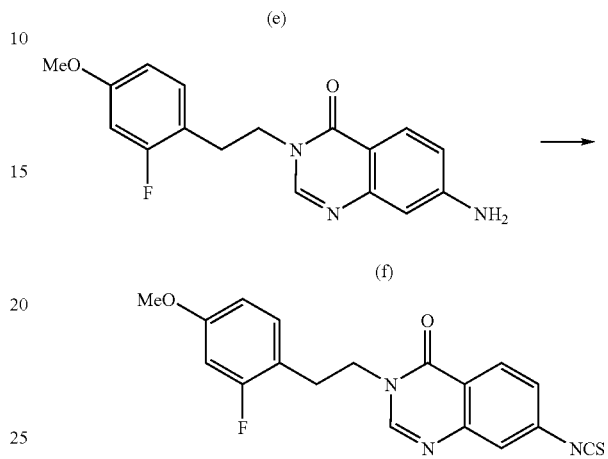

To a mixture of (e), prepared as described in Step 3, (1 equivalent) and $NaHCO_3$ (3 equivalents) in acetone (0.1 M in (e)) was added thiophosgene (3 equivalents) dropwise. The resulting slurry was stirred at room temperature for three hours. Once reaction completion was verified by LC/MS, the reaction was concentrated in vacuo to remove solvent and excess thiophosgene. The mixture was then taken up in ethyl acetate and washed with water. After the organic layer was isolated, the aqueous layer was extracted with two more portions of ethyl acetate. The organic layers were then combined, dried over sodium sulfate, filtered through a cotton plug, and concentrated in vacuo to yield the product ((f): 3-[2-(2-fluoro-4-methoxy-phenyl)-ethyl]-7-isothiocyanato-3H-quinazolin-4-one). The crude product was used in the next reaction without further purification.

Step 5. Synthesis of (g): 1-{3-[2-(2-fluoro-4-methoxy-phenyl)-ethyl]-4-oxo-3,4-dihydro-quinazolin-7-yl}-3-(2,6,6-trimethyl-bicyclo[3.1.1]hept-3-yl)-thiourea

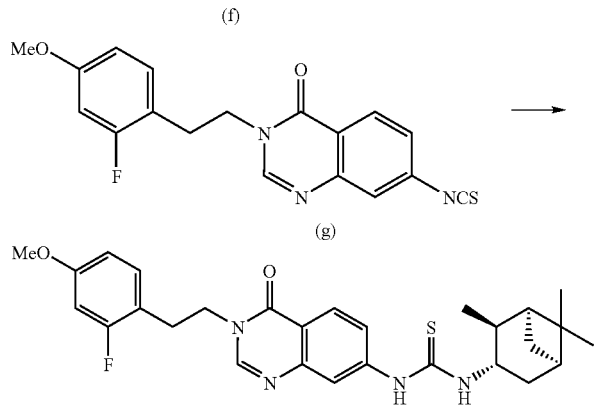

To a solution of (f), prepared as described in Step 4, (1 equivalent) in THF (0.5 M in (f)) was added (1S,2S,3S,5R)-(+)-isopinocampheylamine (1.5 equivalents). The reaction was stirred at room temperature for 10 hours. The crude product mixture was then concentrated in vacuo, dissolved in methylene chloride, and purified via flash chromatography using hexanes/ethyl acetate. The pure fractions were combined and concentrated in vacuo to yield the pure product ((g): 1-{3-[2-(2-fluoro-4-methoxy-phenyl)-ethyl]4-oxo-3,4-dihydro-quinazolin-7-yl}-3-(2,6,6-trimethyl-bicyclo[3.1.1]hept-3-yl)-thiourea).

Step 6. Synthesis of (h): (3R,5S)-N-3-{2-[2-fluoro-4-(methyloxy)phenyl]ethyl}-4-oxo-3,4-dihydro-quinazolin-7-yl)-3,5-dimethyl-N'-[(1S,2S,5R)-2,6,6-trimethylbicyclo[3.1.1]hept-3-yl]piperazine-1-carboximidamide

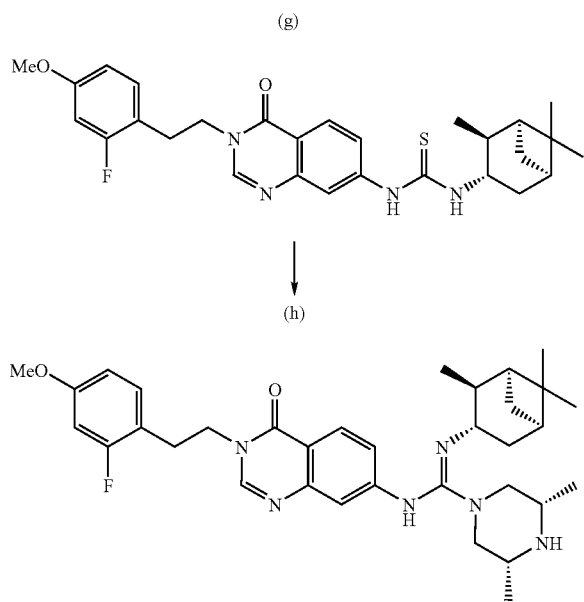

To a solution of (g), prepared as described in Step 5, (1 equivalent) in dry THF (0.1 M in (g)) in a dry round bottom flask was added 1-[3-(dimethylamino)-propyl]-3-ethylcarbodiimide hydrochloride (2 equivalents). The reaction was fitted with a condenser and heated to 80° C. for 1 hour. The resulting solution was allowed to cool to room temperature for 20 minutes. A solution of cis-2,6-dimethylpiperazine (2 equivalents; 0.5 M in $CH_2Cl_2$) was then added to the reaction, and the resulting mixture was stirred at room temperature for 10 minutes. The mixture was then diluted with ethyl acetate and washed with water. After the organic layer was isolated, the aqueous layer was extracted with two more portions of ethyl acetate. The organic layers were then combined and concentrated in vacuo. The crude mixture was dissolved in DMSO and purified via preparative HPLC using water (0.1% TFA)/acetonitrile (0.1% TFA). The pure fractions were combined and concentrated in vacuo to remove the majority of acetonitrile. Sodium carbonate (15 equivalents) was then added to the resulting aqueous solution and the slurry was allowed to sit at room temperature for 1 hour with occasional swirling. The basic aqueous solution was then extracted with 3 separate portions of ethyl acetate. The organic layers were combined, dried over sodium sulfate, filtered through a cotton plug, and concentrated in vacuo to yield product (h) as a free base. The resulting solid was then dissolved in an aqueous HCl solution (1 M; 15 equivalents) and concentrated in vacuo. The resulting mixture was dissolved in a 1:1 water/acetonitrile mixture and lyophilized to yield the pure Bis-HCl salt product ((h): (3R,5S)N-(3-{2-[2-fluoro-4-(methyloxy)phenyl]ethyl}-4-oxo-3,4-dihydroquinazolin-7-yl)-3,5-dimethyl-N'-[(1S,2S,5R)-2,6,6-trimethylbicyclo[3.1.1]hept-3-yl]piperazine-1-carboximidamide.

Synthesis of Compounds of Structure IIIA, IIIB, IIIF, and IIIG

Compounds of formula IIIA, IIIB, IIIF, and IIIG prepared, using the methodology described above using an appropriately substituted pyridine, pyrazine, or pyrimidine benzoic acid, respectively, in place of the 4-nitroanthranilic acid (b) in Step 1. Steps 2-6 may then be carried out to give the final product. One skilled in the art will also recognize that the pyridine may be further substituted to produce variously substituted compounds where $R^4$, $R^5$, and/or $R^6$ are any of the groups herein described such as, but not limited to, fluoro, chloro, alkyl, and alkaryl.

Synthesis of Compounds of Structure IIIC, IIID, and IIIE

Compounds of formula IIIC, IIID, and IIIE are prepared using the methodology described above using an appropriately fluorine-substituted 4-nitroanthranilic acid in place of 4-nitroanthranilic acid (b) in Step 1. Steps 2-6 may then be carried out to give the final product. One skilled in the art will recognize that a fluorine-substituted 4-nitroanthranilic acid may be used which includes further substituents to produce variously substituted compounds where $R^4$, $R^5$, and/or $R^6$ are any of the groups herein described such as, but not limited to, fluoro, chloro, alkyl, and alkaryl.

Synthesis of Compounds of Structure IC

Compounds of formula IC are prepared using the methodology described above using an appropriately substituted 5-nitroanthranilic acid in place of 4-nitroanthranilic acid (b) in Step 1. Steps 2-6 may then be carried out to give the final product. One skilled in the art will recognize that a fluorine-substituted 5-nitroanthranilic acid may be used which includes further substituents to produce variously substituted compounds where $R^4$, $R^5$, and/or $R^6$ are any of the groups herein described such as, but not limited to, fluoro, chloro, alkyl, and alkaryl.

Example 2

Synthesis of 7-{[1-((5S,3R)-3,5-dimethylpiperazinyl)-2-((2S,3S,1R,5R)-2,6,6-trimethylbicyclo[3.1.1]hept-3-yl)(1Z)-2-azavinyl]amino}-3-[2-(2,4-dichlorophenyl)ethyl]-1,3-dihydroquinazoline-2,4-dione

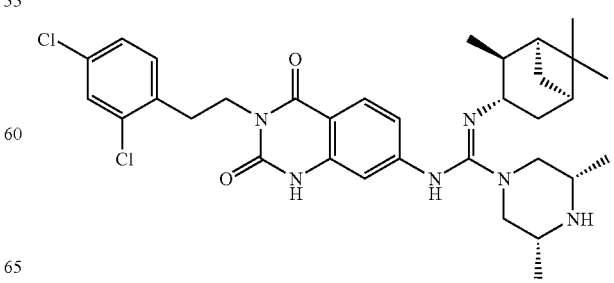

Step 1. Synthesis of (c): 2-amino-N-[2-(2,4-dichlorophenyl)-ethyl]-4-nitro-benzamide

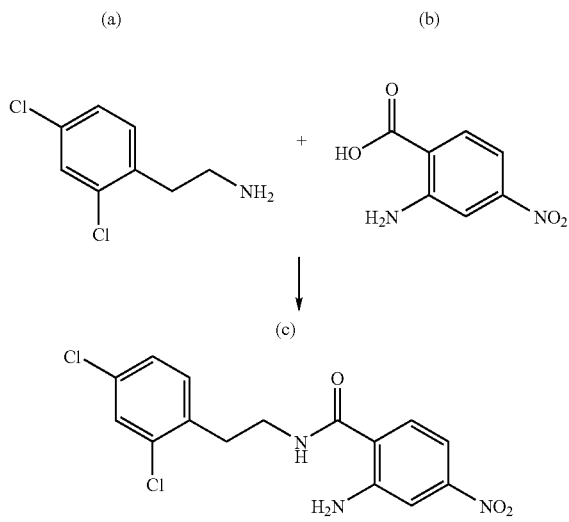

2,4-Dichlorophenylethylamine ((a): 1 equivalent), 4-nitroanthranilic acid ((b): 1 equivalent), HBTU (1.5 equivalent), and dry THF (0.5 M in (a)) were added to a dry round bottom flask. The mixture was allowed to stir for 10 hours at room temperature. The reaction was then dry loaded onto silica gel and purified via flash chromatography using hexanes/ethyl acetate. The pure fractions were combined and concentrated in vacuo to yield the product ((c): 2-amino-N-[2-(2,4-dichloro-phenyl)ethyl]4-nitrobenzamide) as a pure solid.

Step 2. Synthesis of (d): 3-[2-(2,4-dichlorophenyl)ethyl]-7-nitro-1,3-dihydroquinazoline-2,4-dione

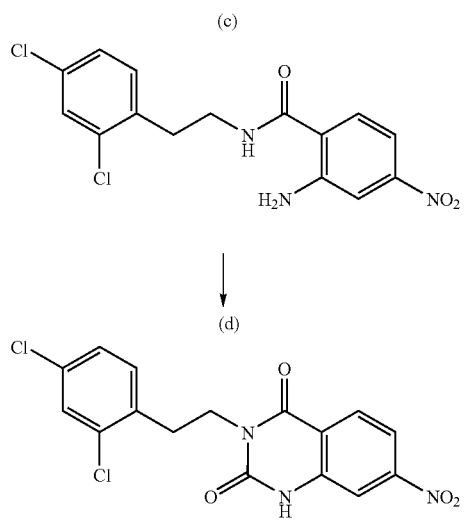

To a 0.3M solution of (c), prepared as described in Step 1, (2.5 g, 7.5 mmol (c)) in dioxane was added 40 mL of a 20% phosgene solution in toluene, followed by 15 mL triethylamine. After stirring for 1 hour at room temperature, solvent was removed by rotary evaporation followed by high vacuum. The residue was dissolved in ethyl acetate and washed three times with water. After drying with sodium sulfate and rotary evaporation, an orange-brown solid ((d): 3-[2-(2,4-dichlorophenyl)ethyl]-7-nitro-1,3-dihydroquinazoline-2,4-dione) was obtained in over 90% yield.

Step 3. Synthesis of (e): 7-amino-3-[2-(2,4-dichlorophenyl)ethyl]-1,3-dihydroquinazoline-2,4-dione

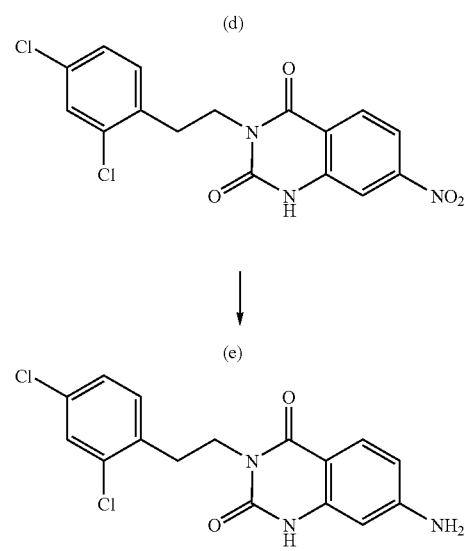

To a solution of (d), prepared as described in Step 2, in MeOH (0.25 M in (d)) was added 10% Pd/C (0.1 equivalents). The mixture was sealed with a septum and degassed with nitrogen for 10 minutes. Hydrogen was then bubbled through the solution for 20 minutes. Once reaction completion was verified by LC/MS, the reaction was degassed with nitrogen for 10 minutes. The mixture was filtered through Celite® and concentrated in vacuo to yield the product ((e)) 7-amino-3-[2-(2,4-dichlorophenyl)ethyl]-1,3-dihydroquinazoline-2,4-dione). The product was used in the next reaction without further purification.

Step 4. Synthesis of (f): 3-[2-(2,4-dichlorophenyl)ethyl]-2,4-dioxo-1,3-dihydroquinazolin-7-isothiocyanate

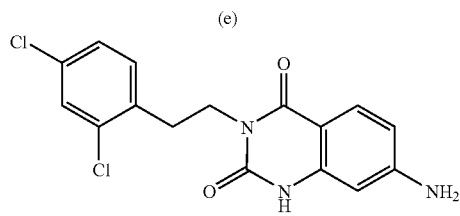

-continued (f)

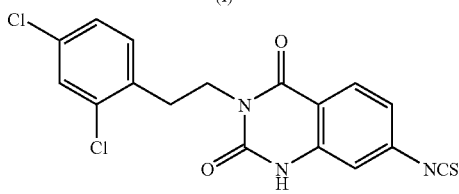

To a mixture of (e), prepared as described in Step 3, (1 equivalent) and NaHCO₃ (3 equivalents) in acetone (0.1 M in (e)) was added thiophosgene (3 equivalents) dropwise. The resulting slurry was stirred at room temperature for three hours. Once reaction completion was verified by LC/MS, the reaction was concentrated in vacuo to remove solvent and excess thiophosgene. The mixture was then taken up in ethyl acetate and washed with water. After the organic layer was isolated, the aqueous layer was extracted with two more portions of ethyl acetate. The organic layers were then combined, dried over sodium sulfate, filtered through a cotton plug, and concentrated in vacuo to yield the product ((f): 3-[2-(2,4-dichlorophenyl)ethyl]-2,4-dioxo-1,3-dihydroquinazolin-7-isothiocyanate). The crude product was used in the next reaction without further purification.

Step 5. Synthesis of (g): 7-({[((2S,3S,1R,5R)-2,6,6-trimethylbicyclo[3.1.1]hept-3-yl)amino]thioxomethyl}amino)-3-[2-(2,4-dichlorophenyl)ethyl]-1,3-dihydroquinazoline-2,4-dione

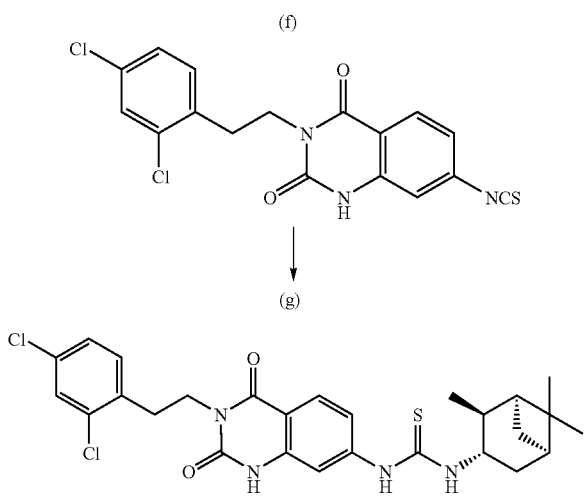

To a solution of (f), prepared as described in Step 4, (1 equivalent) in THF (0.5 M in (f)) was added (1S,2S,3S,5R) (+)-isopinocampheylamine (1.5 equivalents). The reaction was stirred at room temperature for 10 hours. The crude product mixture was then concentrated in vacuo, dissolved in methylene chloride, and purified via flash chromatography using hexanes/ethyl acetate. The pure fractions were combined and concentrated in vacuo to yield the pure product ((g 7-({[((2S,3S,1R,5R)-2,6,6-trimethylbicyclo[3.1.1]hept-3-yl)amino]thioxomethyl}amino)-3-[2-(2,4-dichlorophenyl)ethyl]-1,3-dihydroquinazoline-2,4-dione).

Step 6. Synthesis of (h): 7-{[1-((5S,3R)-3,5-dimethylpiperazinyl)-2-((2S,3S,1R,5R)-2,6,6-trimethylbicyclo[3.1.1]hept-3-yl)(1Z)-2-azavinyl]amino}-3-[2-(2,4-dichlorophenyl)ethyl]-1,3-dihydroquinazoline-2,4-dione

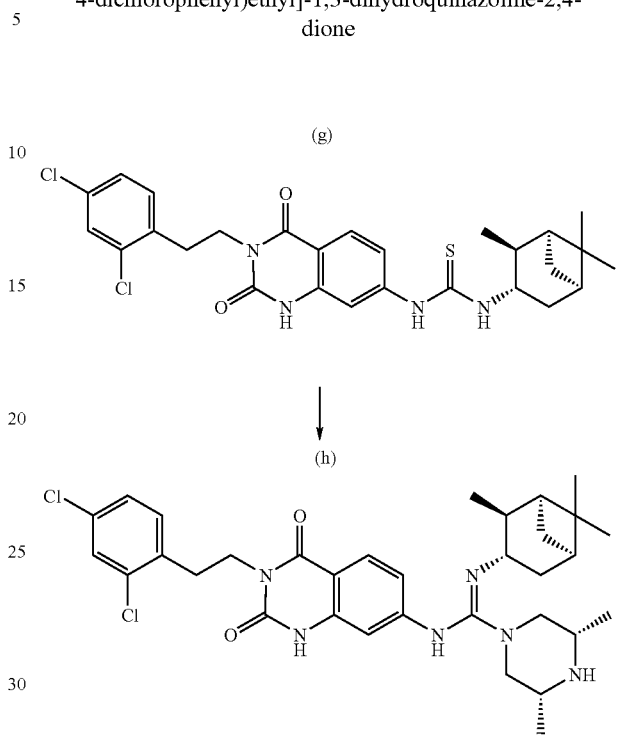

To a solution of (g), prepared as described in Step 5, (1 equivalent) in dry THF (0.1 M in (g)) in a dry round bottom flask was added 1-[3-(dimethylamino)-propyl]-3-ethylcarbodiimide hydrochloride (2 equivalents). The reaction flask was fitted with a water-cooled condenser and heated to 80° C. for 1 hour under a nitrogen atmosphere. The resulting solution was cooled to 0° C. for 20 minutes. A solution of cis-2,6-dimethylpiperazine (2 equivalents; 0.5 M in CH₂Cl₂) was then added to the reaction, and the resulting mixture was stirred at 0° C. for 10 minutes. The mixture was then diluted with ethyl acetate and washed with water. After the organic layer was isolated, the aqueous layer was extracted with two more portions of ethyl acetate. The organic layers were then combined and concentrated in vacuo. The crude mixture was dissolved in DMSO/acetonitrile and purified via preparative HPLC using water (0.1% TFA)/acetonitrile (0.1% TFA). The pure fractions were combined and concentrated in vacuo to remove the majority of acetonitrile. Sodium hydroxide (10 equivalents) was then added to the resulting aqueous solution and the slurry was allowed to sit at room temperature for 1 hour with occasional swirling. The basic aqueous solution was then extracted with 3 separate portions of ethyl acetate. The organic layers were combined, dried over sodium sulfate, filtered through a cotton plug, and concentrated in vacuo to yield product (h) as a free base. The resulting solid was then dissolved in an aqueous HCl solution (1 M; 15 equivalents) and concentrated in vacuo. The resulting mixture was dissolved in a 1:1 water/acetonitrile mixture and lyophilized to yield the pure Bis-HCl salt product ((h): 7-{[1-((5S,3R3,5-dimethylpiperazinyl)-2-((2S,3S,1R,5R)-2,6,6-trimethylbicyclo[3.1.1]hept-3-yl)(1Z)-2-azavinyl]amino}-3-[2-(2,4-dichlorophenyl)ethyl]-1,3-dihydroquinazoline-2,4-dione).

Synthesis of Compounds of Structure IVA and IVB

Compounds of formula IVA and IVB are prepared using the methodology described above using an appropriately substituted pyridine in place of the 4-nitroanthranilic acid (b) in Step 1 b. Procedure 1A may then be carried out to give the final product. One skilled in the art will also recognize that the pyridine may be further substituted to produce variously substituted compounds where $R^4$, $R^5$, and/or $R^6$ are any of the groups herein described such as, but not limited to, fluoro, chloro, alkyl, and alkaryl.

Compounds are prepared using the methodology described above in Procedure A. Procedure 1A may then be carried out to give the final product. One skilled in the art will recognize that a fluorine-substituted 4-nitroanthranilic acid may be used which includes further substituents to produce variously substituted compounds where $R^4$, $R^5$, and/or $R^6$ are any of the groups herein described such as, but not limited to, fluoro, chloro, alkyl, and alkaryl.

Example 3

Synthesis of 7-{[1-((3S)-3-methylpiperazinyl)(1Z)-2-aza-2-(4,4-difluorocyclohexyl)vinyl]amino}-3-[2-(2-fluoro-4-methoxyphenyl)ethyl]-3-hydroquinazolin-4-one

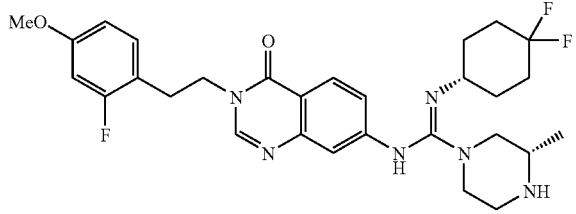

Step 1. Synthesis of (b): 7-({[(4,4 difluorocyclohexyl)amino]-thioxomethyl}amino)-3-[2-(2-fluoro 4-methoxyphenyl)ethyl]-3-hydroquinazolin-4-one

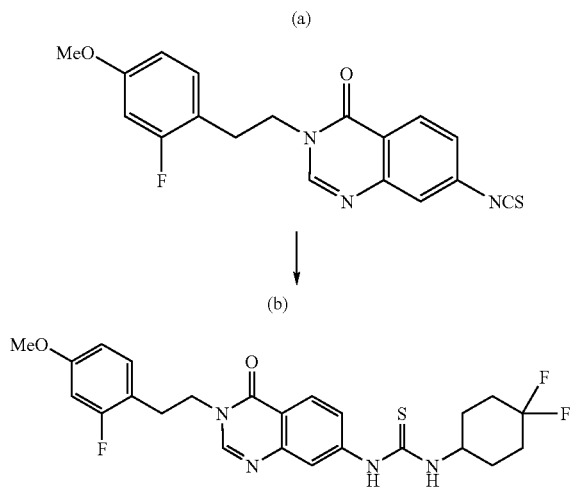

To a solution of (a), prepared as (f) described in Step 4 of Example 1, (1 equivalent) in THF (0.5 M in (a)) was added 4,4-difluorocyclohexylamine prepared as described above (1.5 equivalents). The reaction was stirred at room temperature for 10 hours. The crude product mixture was then concentrated in vacuo, dissolved in methylene chloride, and purified via flash chromatography using hexanes/ethyl acetate. The pure fractions were combined and concentrated in vacuo to yield the pure product ((b): 7-({[(4,4-difluorocyclohexyl)amino]-thioxomethyl}amino)-3-[2-(2-fluoro-4-methoxyphenyl)ethyl]-3-hydroquinazolin-4-one).

Step 2. Synthesis of (c): 7-{[1-((3S)-3-methylpiperazinyl)(1Z)-2-aza-2-(4,4-difluorocyclohexyl)vinyl]amino}-3-[2-(2-fluoro-4-methoxyphenyl)-ethyl]-3-hydroquinazolin-4-one

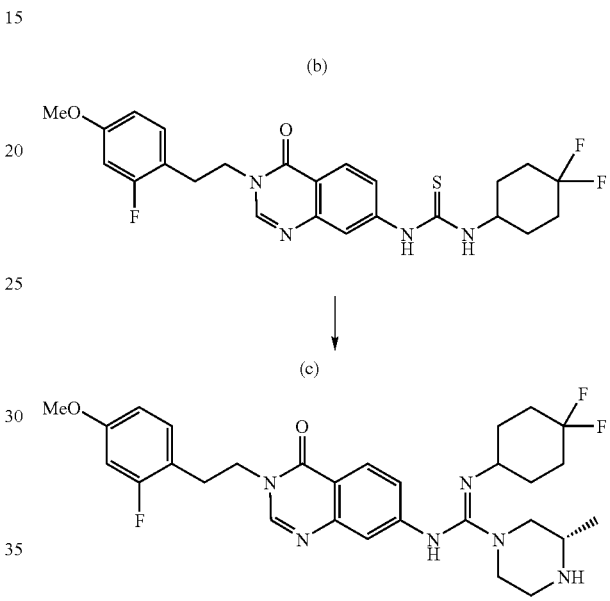

To a solution of (b), prepared as described in Step 1, (1 equivalent) in dry THF (0.1 M in (b)) in a dry round bottom flask was added 1-[3-(dimethylamino)-propyl]-3-ethylcarbodiimide hydrochloride (2 equivalents). The reaction was fitted with a condenser and heated to 80° C. for 1 hour. The resulting solution was allowed to cool to room temperature for 20 minutes. A solution of (S)-2-methylpiperazine (2 equivalents; 0.5 M in $CH_2Cl_2$) was then added to the reaction, and the resulting mixture was stirred at room temperature for 10 minutes. The mixture was then diluted with ethyl acetate and washed with water. After the organic layer was isolated, the aqueous layer was extracted with two more portions of ethyl acetate. The organic layers were then combined and concentrated in vacuo. The crude mixture was dissolved in DMSO and purified via preparative HPLC using water (0.1% TFA)/acetonitrile (0.1% TFA). The pure fractions were combined and concentrated in vacuo to remove the majority of acetonitrile. Sodium carbonate (15 equivalents) was then added to the resulting aqueous solution and the slurry was allowed to sit at room temperature for 1 hour with occasional swirling. The basic aqueous solution was then extracted with 3 separate portions of ethyl acetate. The organic layers were combined, dried over sodium sulfate, filtered through a cotton plug, and concentrated in vacuo to yield product (c) as a free base. The resulting solid was then dissolved in an aqueous HCl solution (1 M; 15 equivalents) and concentrated in vacuo. The resulting mixture was dissolved in a 1:1 water/acetonitrile mixture and lyophilized to yield the pure Bis-HCl salt product ((c): 7-{[1-((3S)-3-methylpiperazinyl)(1Z)-2-aza-2-(4,4-difluorocyclohexyl)vinyl]amino}3-[2-(2-fluoro-4-methoxyphenyl)-ethyl]-3-hydroquinazolin-4-one).

Method 1 Synthesis of 3-[2-(4-fluorophenyl)ethyl]-7-nitro-2-(4-pyridyl)-3-hydroquinazolin-4-one

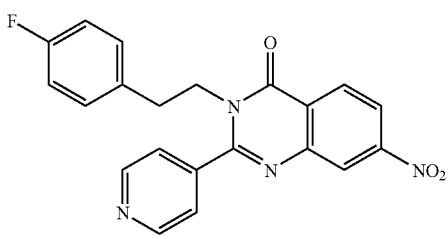

Pyridine 4-carboxylic acid was stirred in POCl₃ at room temperature for about 5 minutes. To the stirred solution was then added 0.9 equivalents of (2-amino-4-nitrophenyl)-N-[2-(4-fluorophenyl)ethyl]carboxamide. The resulting mixture was then stirred for about 15 minutes at room temperature in a microwave tube, which was then heated to 165° C. in a microwave for 10 minutes. LC/MS indicated completion of the reaction. The POCl₃ was evaporated, and the residue was dissolved in CH₂Cl₂ and washed with saturated sodium bicarbonate solution. The combined organic layers were dried over MgSO₄ and concentrated in vacuo and chromatographed on silica gel, eluting with a gradient of EtOAc in Hexanes. The resulting product, 3-[2-(4-fluorophenyl)ethyl]-7-nitro-2-(4-pyridyl)-3-hydroquinazolin-4-one, was then converted to Example 77 using the procedures described in Scheme 1a.

Method 2 Synthesis of 2-[2-(2-fluoro-4-methoxyphenyl)ethyl]-3-methyl-7-nitro-3-hydroquinazolin-4-one

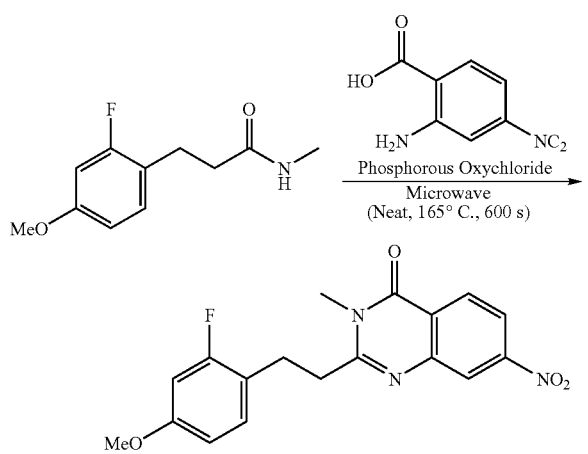

3-(2-Fluoro-4-methoxy-phenyl)-N-methyl-propionamide was synthesized using an EDCI mediated coupling of 3-(2-fluoro-4-methoxy-phenyl)-N-methyl-propionic acid and methylamine (2M solution in THF). The amide was then taken up in POCl₃ in a microwave vessel and the mixture was stirred about 3 minutes. To the stirred solution was added about 1 equivalent of 4-nitroanthranilic acid. The unsealed vial was stirred for 10 minutes until there was a color change from red to yellow. The vial was then sealed and reacted in a microwave unit at 165° C. for 600 seconds. Reaction completion was checked with LC/MS. 2-[2-(2-Fluoro-4-methoxyphenyl)ethyl]-3-methyl-7-nitro-3-hydroquinazolin-4-one was then purified by column chromatography, eluting with EtOAc in hexanes. 2-[2-(2-Fluoro-4-methoxyphenyl)ethyl]-3-methyl-7-nitro-3-hydroquinazolin-4-one was then converted to Example 90 using the procedures described above through the corresponding thiourea (Scheme 1a).

Method 3 Synthesis of 3-[2-(2-fluoro-4-methoxyphenyl)ethyl]-2-(4-methylpiperazinyl)-7-nitro-3-hydroquinazolin-4-one (B) and 3-[2-(2-fluoro-4-methoxyphenyl)ethyl]-2-[imino(4-methylpiperazinyl)-methyl]-7-nitro-3-hydroquinazolin-4-one (C)

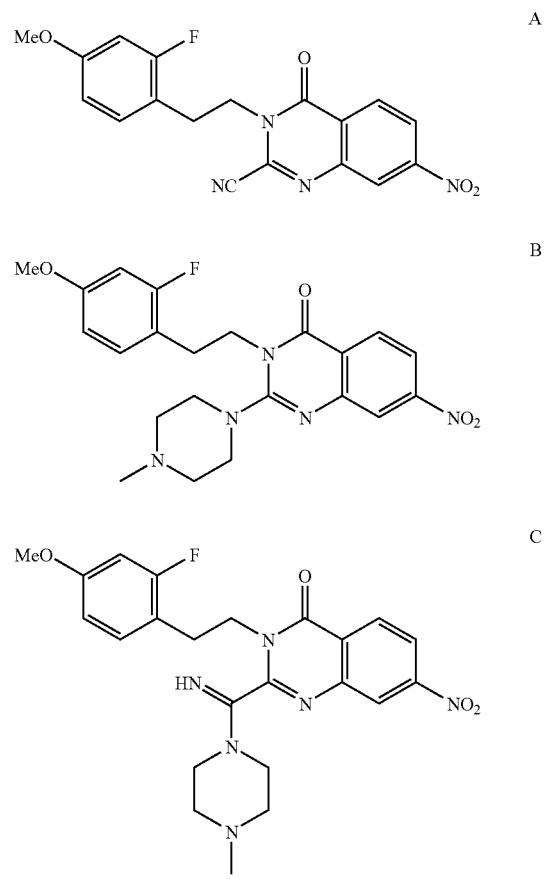

The synthesis of nitrile A was first conducted as described in J. Heterocyclic Chem., 35, 659 (1998)). Nitrile A was heated in an excess of N-methylpiperazine to 110° C. in a microwave for 600 seconds and analyzed by LC/MS to provide B and C. Products B and C were separated by column chromatography on silica gel eluting with 10% MeOH in CH₂Cl₂. Compound B was the first to come off the column. Compounds B and C were then respectively converted to Examples 99 and 71 using the procedures described herein.

Method 4 Synthesis of 3-[2-(2-fluoro-4-methoxyphenyl)ethyl]-7-nitro-2-(1,2,3,4-tetraazol-5-yl)-3-hydroquinazolin-4-one

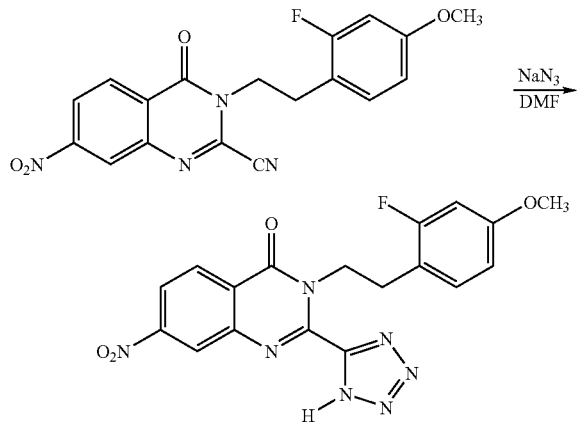

Nitrile 1 shown above (0.9 g, 2.4 mmoles) was dissolved in dry DMF (5 mL). Sodium azide (0.8 g, 12.2 mmoles) was added and the mixture was heated at 125° C. for 1 hour. The reaction was cooled, diluted with water (25 mL), and filtered. The collected solid was redissolved in THF/EtOAc 1:1 (25 mL), washed with water (25 mL), and dried over MgSO$_4$. Filtration and solvent removal afforded 650 mg of a brown solid. The $^1$H NMR (DMSO-d$_6$, 300 MHz) was consistent with desired product formation. The product was converted to Example 78 using the procedures described herein.

Method 5 Synthesis of 3-[2-(4-fluorophenyl)ethyl]-2-[(4-methylpiperazinyl)-methyl]-7-nitro-3-hydroquinazolin-4-one (3)

Step 1 Synthesis of 2-chloro-N-[2-(4-fluoro-phenyl)-ethyl]-acetamide (1)

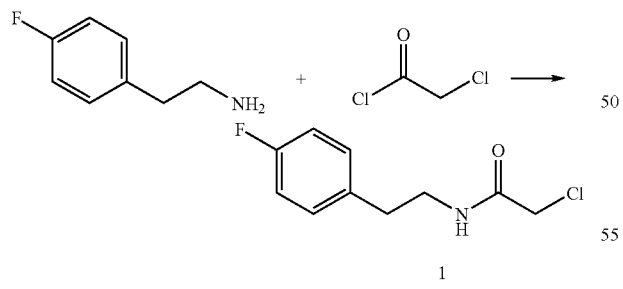

To a solution of 4-fluorophenylethylamine (1.0 equivalent) in dried THF was added Hunig's base (DIEA)(1 equivalent). The mixture was then stirred for 3 minutes at 0° C. Thereafter, a solution of chloroacetylchloride (1.0 equivalent) in THF was added via a syringe over a period of 7 minutes. The reaction mixture was then stirred at room temperature for 1 hour after which time the reaction mixture was condensed in vacuo, quenched with water, extracted with ethyl acetate (3×) and dried over Na$_2$SO$_4$. After concentration in vacuo, compound 1 shown above was obtained, which was carried on further without further purification. LC/MS=M+H 216.1 at 2.18 minutes.

Step 2 Synthesis of 2-chloromethyl-3-[2-(4-fluorophenyl)-ethyl]-7-nitro-3H-quinazolin-4-one (2)

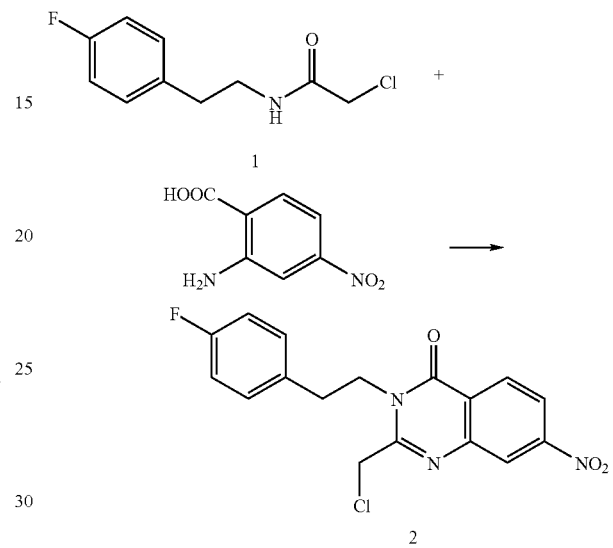

Compound 1 (1.2 equivalents) was dissolved in neat POCl$_3$ and allowed to stir under N$_2$ for 5 minutes. Solid 4-nitroanthranilic acid (1.0 equivalent) was then added, and the mixture was allowed to stir at room temperature for 10 minutes until the color changed to yellow from red. Thereafter, the reaction mixture was refluxed at 100° C. for 2 hours, followed by removal of POCl$_3$ in vacuo (addition of triethylamine to the rotovap condenser). The crude product so obtained was neutralized with a saturated solution of NaHCO$_3$ extracted with ethyl acetate (3 times), dried over Na$_2$SO$_4$, and condensed in vacuo. Purification of the crude product was carried out with column chromatography in several batches using a gradient of EtOAc in hexanes. LC/MS=M+H 3.62 at 3.5 minutes.

Step 3 Synthesis of 3-[2-(4-fluorophenyl)ethyl]-2-[(4-methylpiperazinyl)-methyl]-7-nitro-3-hydroquinazolin-4-one (3)

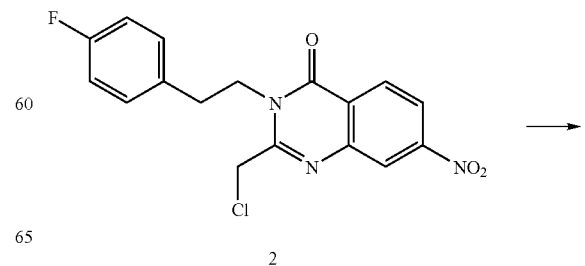

-continued

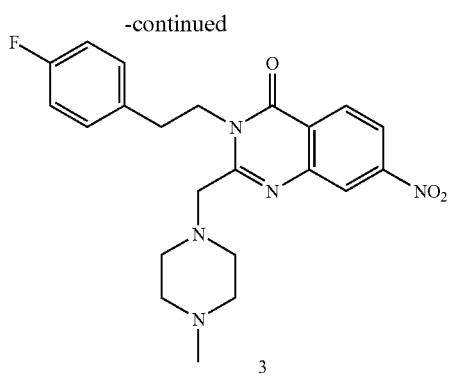

A solution of 2 (1 equivalent) and 4-methylpiperazine (3 equivalents) in 2 mL NMP were heated at 80° C. After stirring for 18 hours, the dark brown solution was diluted with ethyl acetate and washed twice with water. The organic phase was then dried with sodium sulfate, filtered and concentrated in vacuo, and taken on to the next step without further purification. Compound 3 was then converted to Example 69 using the procedures described herein. This procedure yielded a dark oil, and small amounts of NMP may remain in the product. Formation of some analogous compounds required the addition of three equivalents of diisopropyl ethyl amine. Similar chemistry was used to prepare Examples 67, 70, 72, 74, 75, 79, and 81 as identified in the following tables.

Step 3a Synthesis of 2-[(2,4-difluorophenoxy)methyl]-3-methyl-7-nitro-3-hydroquinazolin-4-one

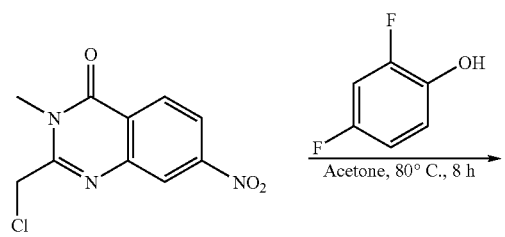

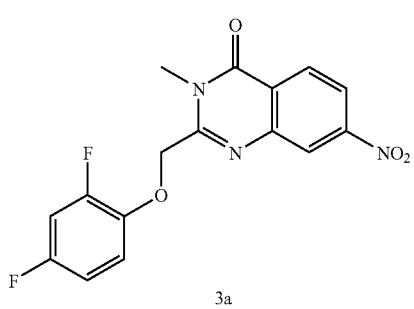

2,4-Difluorophenol (2.5 equivalents) was added to 2-(chloromethyl)-3-methyl-7-nitro-3-hydroquinazolin-4-one (2a) in acetone and refluxed for 8 hours. The solution was then cooled to room temperature, washed with saturated sodium bicarbonate, dried and filtered over sodium sulfate and concentrated in vacuo to afford 2-[(2,4-difluorophenoxy)methyl]-3-methyl-7-nitro-3-hydroquinazolin-4-one in quantitative yields. Compound 3a was then converted to Example 88 using the procedures described herein. Similar chemistry was used to prepare Examples 68, 89, 92, 93, 94, 95, 96, 97, 98, and 100 as identified in the following tables.

Method 6 Synthesis of 3-[2-(2-fluoro-4-methoxyphenyl)ethyl]-7-nitrobenzo[d]1,2,3-trazin-4-one

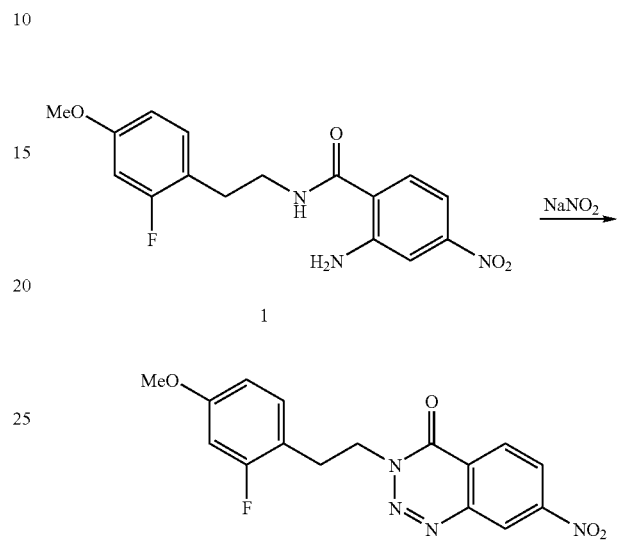

A mixture of benzamide (1) (3.42 mmol), water (40 mL), and concentrated HCl (12 mL) was cooled in an ice bath, and a solution of NaNO$_2$ (3.6 mmol) in water (5 mL) was added drop wise. The mixture was stirred for 1 hour, and 20 mL 10 N NaOH was added. The stirring was continued for another hour, and the reaction was neutralized with AcOH, extracted with methylene chloride, and dried over MgSO4. The crude product was chromatographed on silica (30%) EtOAc/hexanes) yielding the desired product as a yellow solid. The purified compound was then converted to Example 102 using the procedures described herein.

Method 7 Synthesis of 6-amino-2-[2-(2-fluoro-4-methoxyphenyl)ethyl]-2-hydroisoquinolin-1-one Step 1

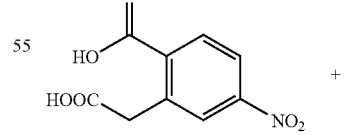

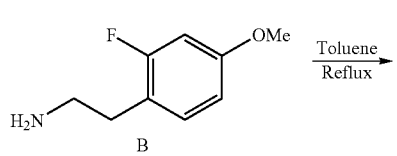

-continued

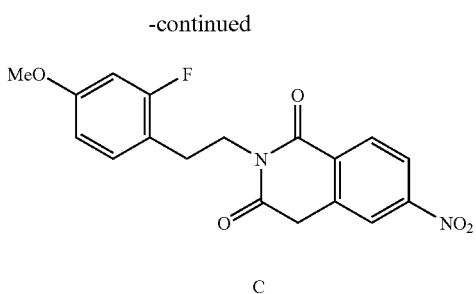
C

The diacid A (1 equivalent) was added to a flask equipped with a reflux condenser and dean stark trap and charged with dry toluene. The mixture was heated to reflux and then 2-(2-fluoro-4-methoxy-phenyl)-ethylamine B (1 equivalent) was added. The reaction was kept at reflux overnight, and then the toluene was removed by rotary evaporation. Purification by flash chromatography using ethyl acetate/hexanes provided the product C in 30% yield.

Step 2

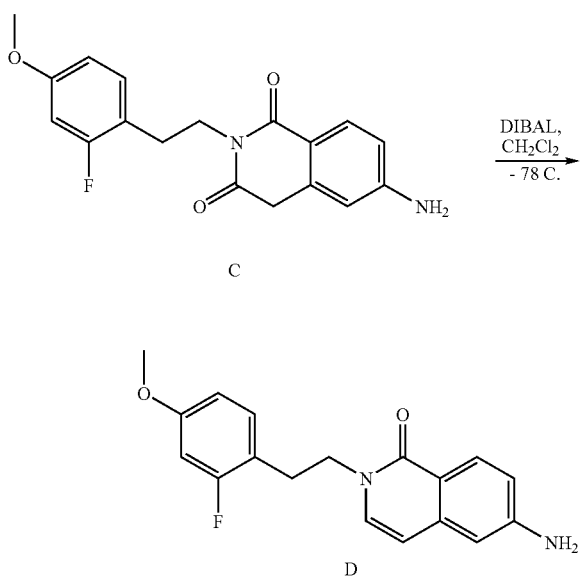

The imide (C) was dissolved in $CH_2Cl_2$ and cooled to −78° C. 3 equivalents of DIBAL (1M in $CH_2Cl_2$) were added, and the reaction was stirred at −78° C. for 1 hour when LC/MS indicated completion of the reaction. The solution was then diluted with ether and 10 equivalents of NaF and 4 equivalents water were added. The reaction was then stirred for an hour. The reaction was then filtered through Celite® to yield the crude pyridone amine (D). Compound D was then converted to Example 103 using the procedures described herein. Similar chemistry was used to prepare Example 104 as identified in the final table.

As noted below, the compounds in the following tables were prepared using the methodology described herein from commercially available starting materials which are readily recognizable by those skilled in the art or by using known synthetic methods. For example, Example 11 was prepared using the methodology described in Scheme I a and the appropriate amino indanol. Examples 14 and 18 which include hydroxymethyl-substituted arylalkyl groups were also prepared using the general methodology of Scheme 1a with the appropriate amino alcohol. N-cyano substituted piperazine compound Example 36 was prepared by: first, mono-Boc protecting 2,6-trans dimethylpiperazine; second, treating the mono-Boc protected compound with cyanogen bromide (2.5 equivalents) and Hunig's base (1.1 equivalent); third, purifying the resulting nitrile piperazine compound on silica gel; fourth, deprotecting the purified compound; and fifth, reacting the resulting purified nitrile trans dimethyl piperazine compound using the methods described herein to produce Example 36. Compounds such as Examples 73 and 76 were prepared using the procedure of Method 2 with the appropriated amides of methacrylic acid and acetic acid.

Compounds of formula IB where $R^2$ is an alkyl group such as Example 59 where $R^2$ is a methyl group may be prepared by alkylating a dione where $R^2$ is H prepared as described herein. For example, Example 59 was prepared using the methylation procedure shown below (reaction of dione with methyl iodide and potassium carbonate (1:2:2) in DMF at 60° C. to produce the nitro compound which was then converted to Example 59 using the standard procedures described herein.

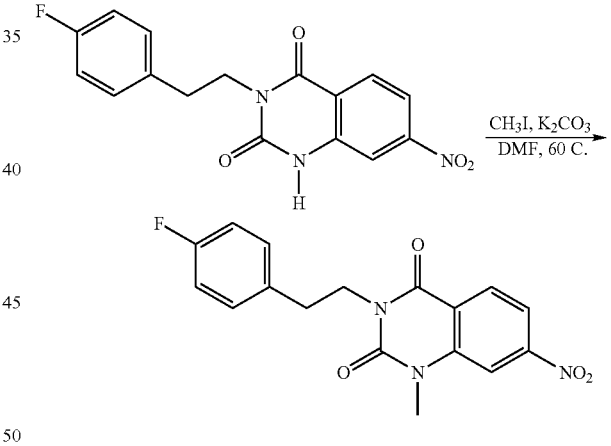

The compounds in the following tables were prepared using the methodology described in Examples 1-3 and the above Methods and Procedures. The starting materials used in the syntheses are recognizable to one of skill in the art and are commercially available or may be prepared using known methods. The synthesis of various guanidine compounds is known in the art. Such synthesis information may be found in the following references each of which is incorporated herein in its entirety: PCT publication WO 02/18327; U.S. patent application Ser. No. 09/945,384; U.S. Provisional Patent Application Ser. No. 60/230,565; U.S. Provisional Patent Application Ser. No. 60/245,579; U.S. Provisional Application Ser. No. 60/282,847; U.S. Provisional Application Ser. No. 60/353,183; and U.S. Provisional Application Ser. No. 60/353,188.

TABLE of Examples 4-66

| No. | Structure | Name | MH+ |
| --- | --- | --- | --- |
| 4 | 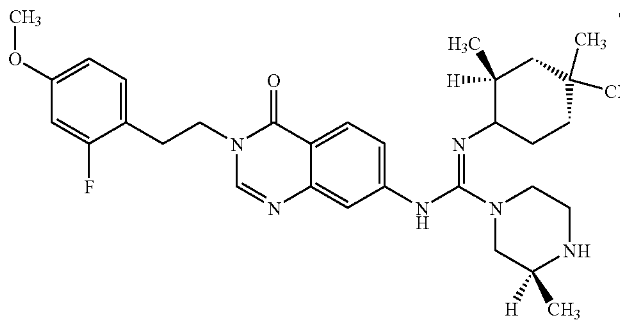 | (3S)-N-(3-{2-[2-fluoro-4-(methyloxy)phenyl]ethyl}-4-oxo-3,4-dihydroquinazolin-7-yl)-3-methyl-N'-[(1S,2S,5R)-2,6,6-trimethylbicyclo[3.1.1]hept-3-yl]piperazine-1-carboximidamide | 575.7 |
| 5 | 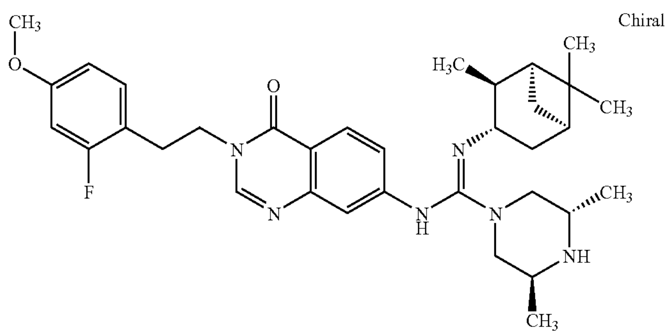 | (3S,5S)-N-(3-{2-[2-fluoro-4-(methyloxy)phenyl]ethyl}-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 589.8 |
| 6 | 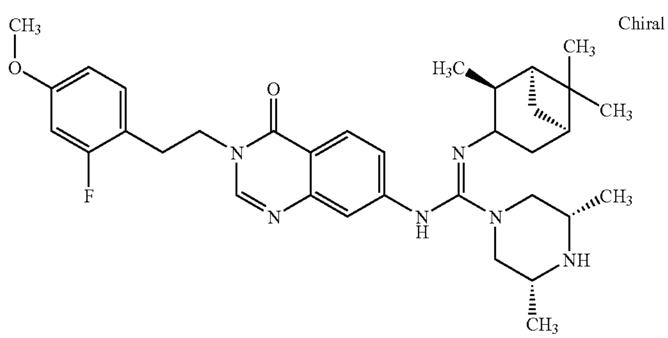 | (3R,5S)-N-(3-{2-[2-fluoro-(methyloxy)phenyl]ethyl}-4-oxo-3,4-dihydroquinazolin-7-yl)-3,5-dimethyt-N'-[(1S,2S,5R)-2,6,6-trimethylbicyclo[3.1.1]hept-3-yl]piperazine-1-carboximidamide | 589.8 |
| 7 | 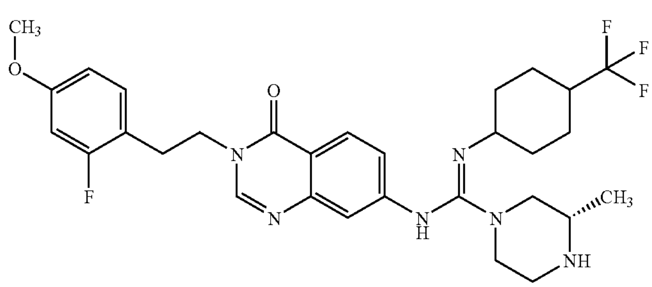 | (3S)-N-(3-{2-[2-fluoro-4-(methyloxy)phenyl]ethyl}-4-oxo-3,4-dihydroquinazolin-7-yl)-3-methyl-N'-[4-(trifluoromethyl)cyclohexyl]piperazine-1-carboximidamide | 589.6 |

TABLE-continued of Examples 4-66

| No. | Structure | Name | MH+ |
|---|---|---|---|
| 8 | 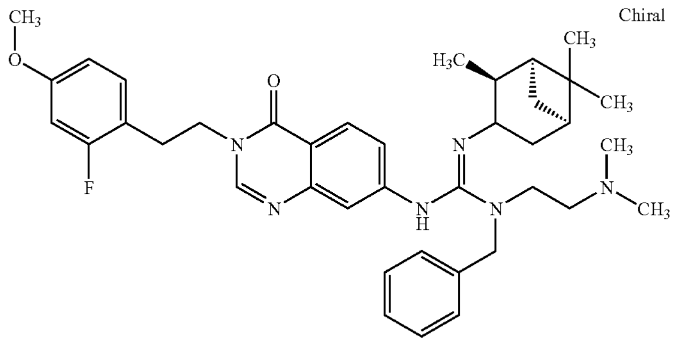 | N-[2-(dimethylamino)ethyl]-N'-(3-{2-(2-fluoro-4-(methyloxy)phenyl]ethyl}-4-oxo-3,4-dihydroquinazolin-7-yl)-N-(phenylmethyl)-N''-[(1S,2S,5R)-2,6,6-trimethylbicyclo[3.1.1]hept-3-yl]guanidine | 653.9 |
| 9 | 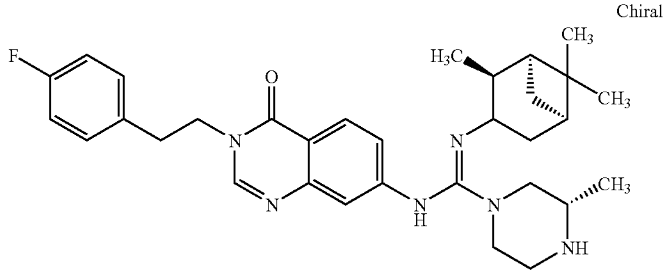 | (3S)-N-{3-[2-(4-fluorophenyl)ethyl]-4-oxo-3,4-dihydroquinazolin-7-yl}-3-methyl-N'-[(1S,2S,5R)-2,6,6-trimethylbicyclo[3.1.1]hept-3-yl]piperazine-1-carboximidamide | 545.7 |
| 10 | 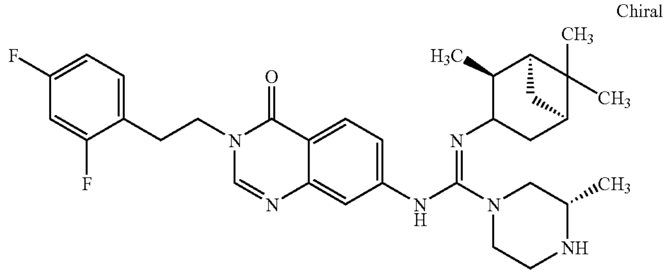 | (3S)-N-{3-[2-(2,4-difluorophenyl)ethyl]-4-oxo-3,4-dihydroquinazolin-7-yl}-3-methyl-N'-[(1S,2S,5R)-2,6,6-trimethylbicyclo[3.1.1]hept-3-yl]piperazine-1-carboximidamide | 563.7 |
| 11 | 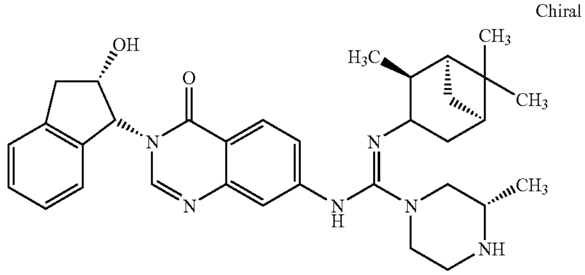 | (3S)-N-{3-[(1R,2S)-2-hydroxy-2,3-dihydro-1H-inden-1-yl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 555.7 |
| 12 | 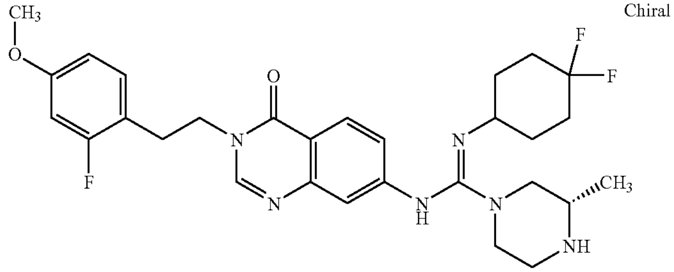 | (3S)-N'-(4,4-difluorocyclohexyl)-N-(3-{2-[2-fluoro-4-(methyloxy)phenyl]ethyl}-4-oxo-3,4-dihydroquinazolin-7-yl)-3-methylpiperazine-1-carboximidamide | 557.6 |

TABLE-continued of Examples 4-66

| No. | Structure | Name | MH+ |
|---|---|---|---|
| 13 | Chiral | (3S)-N'-(4-fluorocyclohexyl)-N-(3-{2-(2-fluoro-4-(methyloxy)phenyl]ethyl}-4-oxo-3,4-dihydroquinazolin-7-yl)-3-methylpiperazine-1-carboximidamide | 539.6 |
| 14 | Chiral | (3S)-N-{3-[(1S)-1-(hydroxymethyl)-3-methylbutyl]-4-oxo-3,4-dihydroquinazolin-7-yl}-3-methyl-N'-[(1S,2S,5R)-2,6,6-trimethylbicyclo[3.1.1]hept-3-yl]piperazine-1-carboximidamide | 523.7 |
| 15 | Chiral | (3R,5S)-N-(3-{2-[2-fluoro-4-(methyloxy)phenyl]ethyl}-4-oxo-3,4-dihydroquinazolin-7-yl)-3,5-dimethyl-N'-(2-methylcyclohexyl)piperazine-1-carboximidamide | 549.7 |
| 16 | Chiral | (3R,5S)-N-(3-{2-[2-fluoro-4-(methyloxy)phenyl]ethyl}-4-oxo-3,4-dihydroquinazolin-7-yl)-3,5-dimethyl-N'-(4-methylcyclohexyl)piperazine-1-carboximidamide | 549.7 |

TABLE-continued of Examples 4-66

| No. | Structure | Name | MH+ |
|---|---|---|---|
| 17 | 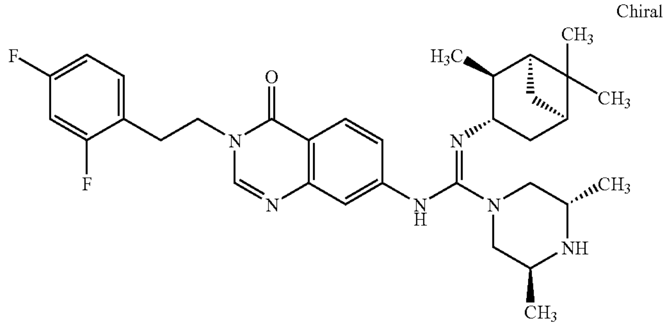 | (3S,5S)-N-{3-[2-(2,4-difluorophenyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 577.7 |
| 18 | 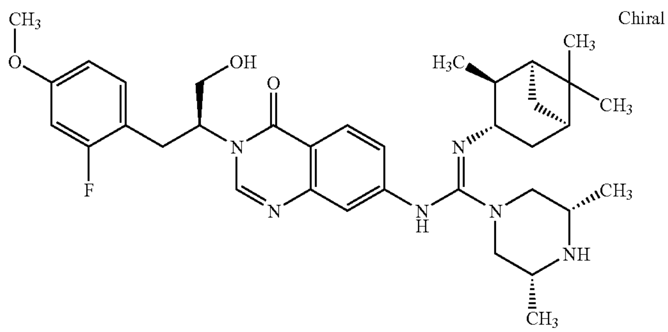 | (3R,5S)-N-{3-[(1S)-2-[2-fluoro-4-(methyloxy)phenyl]-1-(hydroxymethyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 619.8 |
| 19 | 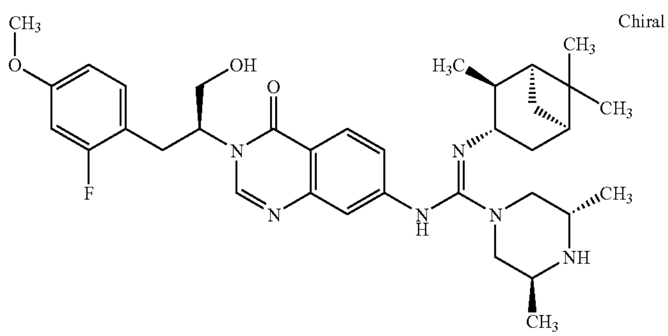 | (3S,5S)-N-{3-[(1S)-2-[2-fluoro-4-(methyloxy)phenyl]-1-(hydroxymethyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 619.8 |
| 20 | 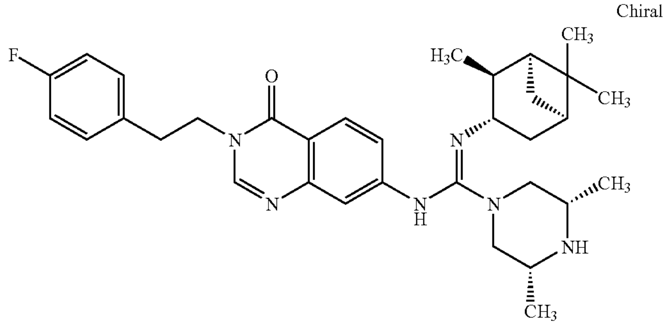 | (3R,5S)-N-{3-[2-(4-fluorophenyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 559.7 |

TABLE-continued of Examples 4-66

| No. | Structure | Name | MH+ |
|---|---|---|---|
| 21 | 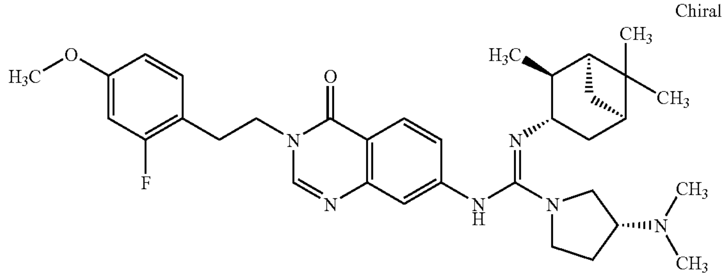 | (3R)-3-(dimethylamino)-N-(3-{2-[2-fluoro-4-(methyloxy)phenyl]ethyl}-4-oxo-3,4-dihydroquinazolin-7-yl)-N'-[(1S,2S,3S,5R)-2,6,6-trimethylbicyclo[3.1.1]hept-3-yl]pyrrolidine-1-carboximidamide | 589.8 |
| 22 | 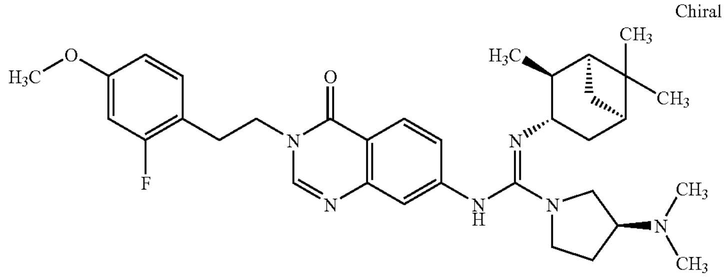 | (3S)-3-(dimethylamino)-N-(3-{2-[2-fluoro-4-(methyloxy)phenyl]ethyl}-4-oxo-3,4-dihydroquinazolin-7-yl)-N'-[(1S,2S,3S,5R)-2,6,6-trimethylbicyclo[3.1.1]hept-3-yl]pyrrolidine-1-carboximidamide | 589.8 |
| 23 | 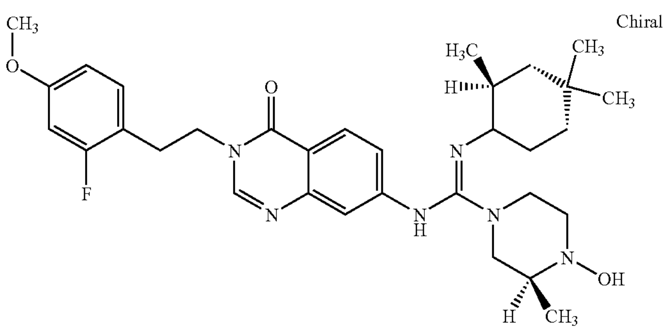 | (3S)-N-(3-{2-[2-fluoro-4-(methyloxy)phenyl]ethyl}-4-oxo-3,4-dihydroquinazolin-7-yl)-4-hydroxy-3-methyl-N'-[(1S,2S,5R)-2,6,6-trimethylbicyclo[3.1.1]hept-3-yl]piperazine-1-carboximidamide | 591.7 |
| 24 | 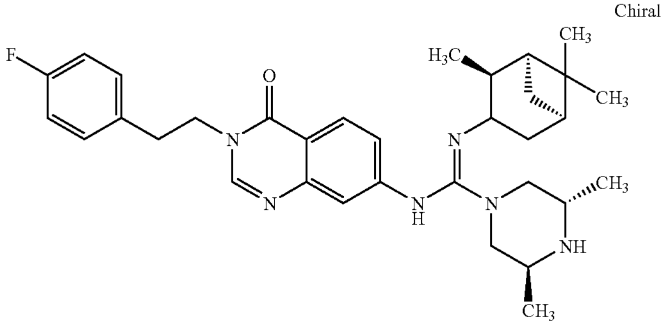 | (3S,5S)-N-{3-[2-(4-fluorophenyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 559.7 |

TABLE-continued of Examples 4-66

| No. | Structure | Name | MH+ |
|---|---|---|---|
| 25 | 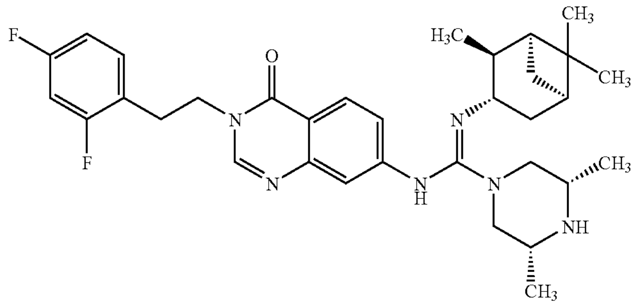 | (3R,5S)-N-{3-[2-(2,4-difluorophenyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 577.7 |
| 26 | 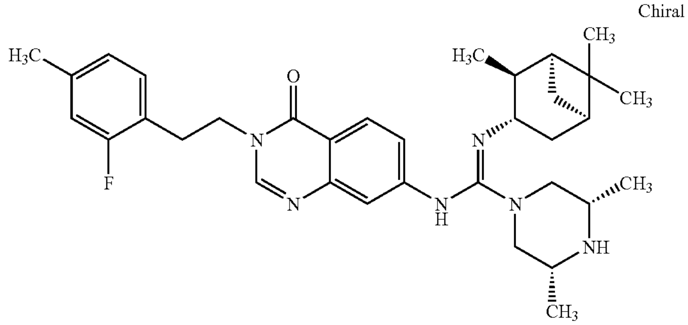 | (3R,5S)-N-{3-[2-(2-fluoro-4-methylphenyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 573.8 |
| 27 | 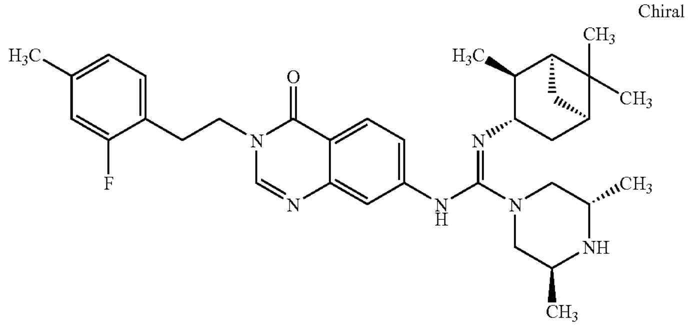 | (3S,5S)-N-{3-[2-(2-fluoro-4-methylphenyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 573.8 |
| 28 | 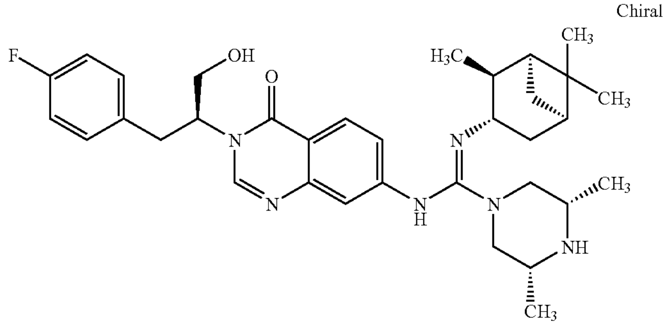 | (3R,5S)-N-{3-[(1S)-2-(4-fluorophenyl)-1-(hydroxymethyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 589.8 |

TABLE-continued of Examples 4-66

| No. | Structure | Name | MH+ |
|---|---|---|---|
| 29 | 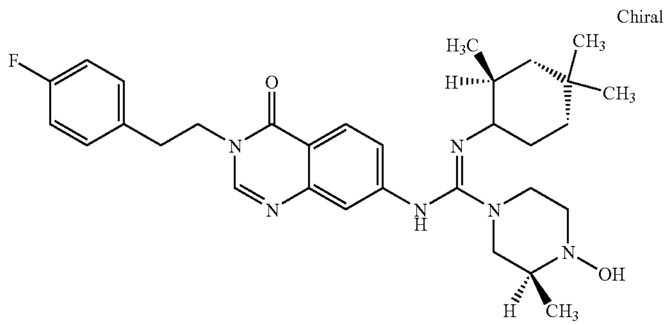 | (3S)-N-{3-[2-(4-fluorophenyl)ethyl]-4-oxo-3,4-dihydroquinazolin-7-yl}-4-hydroxy-3-methyl-N'-[(1S,2S,5R)-2,6,6-trimethylbicyclo[3.1.1]hept-3-yl] piperazine-1-carboximidamide | 561.7 |
| 30 | 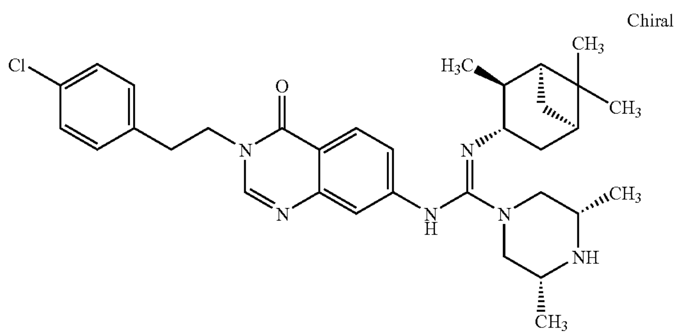 | (3R,5S)-N-{3-[2-(4-chlorophenyl)ethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 576.2 |
| 31 | 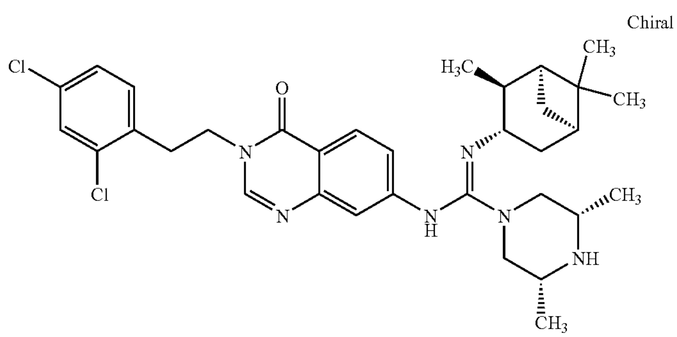 | (3R,5S)-N-{3-[2-(2,4-dichlorophenyl)ethyl]-4-oxo-3,4-dihydroquinazolin-7-yl}-3,5-dimethyl-N'-[(1S,2S,5R)-2,6,6-trimethylbicyclo[3.1.1]hept-3-yl] piperazine-1-carboximidamide | 610.6 |
| 32 | 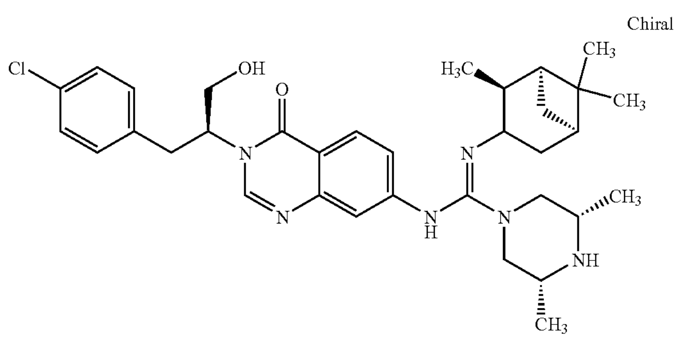 | (3R,5S)-N-{3-[(1S)-2-(4-chlorophenyl)-1-(hydroxymethyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 606.2 |

TABLE-continued of Examples 4-66

| No. | Structure | Name | MH+ |
|---|---|---|---|
| 33 | 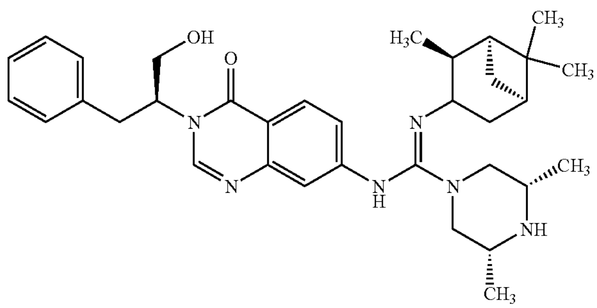 | (3R,5S)-N-{3-[(1S)-2-hydroxy-1-(phenylmethyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 517.8 |
| 34 | 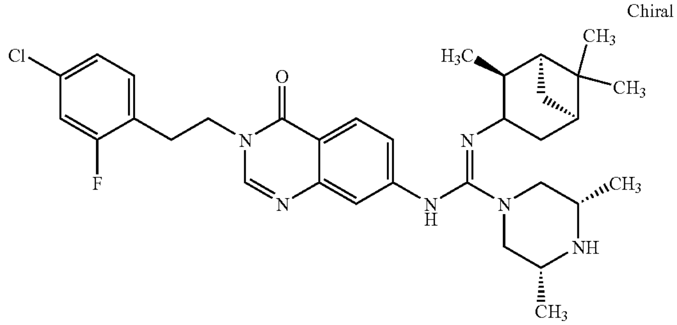 | (3R,5S)-N-{3-[2-(4-chloro-2-fluorophenyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 594.2 |
| 35 | 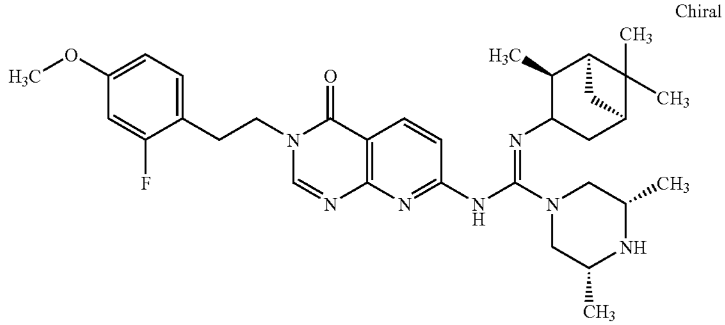 | (3R,5S)-N-(3-{2-[2-fluoro-4-(methyloxy)phenyl]ethyl}-4-oxo-3,4-dihydropyrido[2,3-d]pyrimidin-7-yl)-3,5-dimethyl-N'-[(1S,2S,3S,5R)-2,6,6-trimethylbicyclo[3.1.1]hept-3-yl]piperazine-1-carboximidamide | 590.8 |
| 36 | 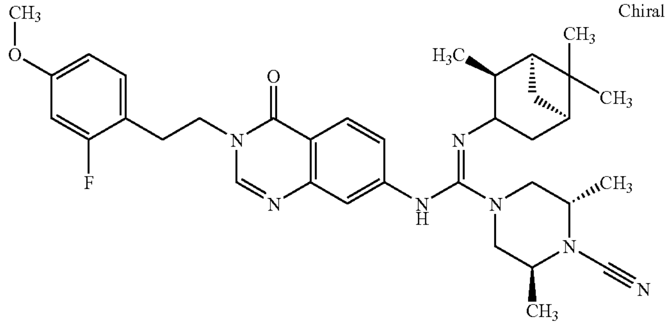 | (3S,5S)-4-cyano-N-(3-{2-[2-fluoro-4-(methyloxy)phenyl]ethyl}-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 614.8 |

TABLE-continued of Examples 4-66

| No. | Structure | Name | MH+ |
|---|---|---|---|
| 37 | 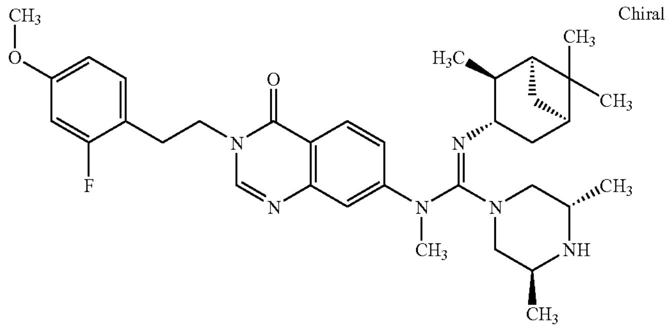 | (3S,5S)-N-(3-{2-[2-fluoro-4-(methyloxy)phenyl]ethyl}-4-oxo-3,4-dihydroquinazolin-7-yl)-3,5-trimethyl-N'-[(1S,2S,3S,5R)-2,6,6-trimethylbicyclo[3.1.1]hept-3-yl]piperazine-1-carboximidamide | 603.8 |
| 38 | 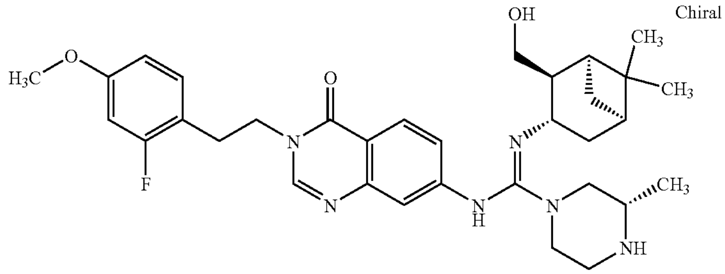 | (3S)-N-(3-{2-[2-fluoro-4-(methyloxy)phenyl]ethyl}-4-oxo-3,4-dihydroquinazolin-7-yl)-N'-[(1S,2S,3S,5R)-2-(hydroxymethyl)-6,6-dimethylbicyclo[3.1.1]hept-3-yl]-3-methylpiperazine-1-carboximidamide | 591.7 |
| 39 | 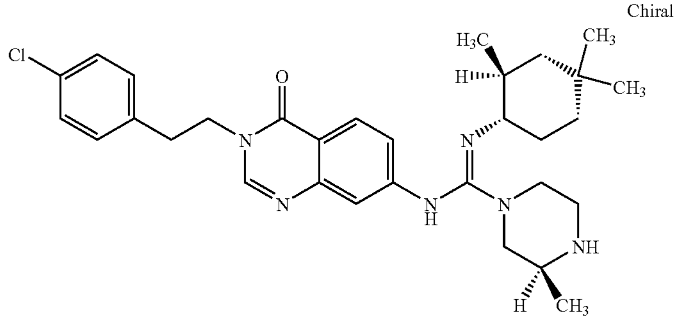 | (3S)-N-{3-[2-(4-chlorophenyl)ethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 562.2 |
| 40 | 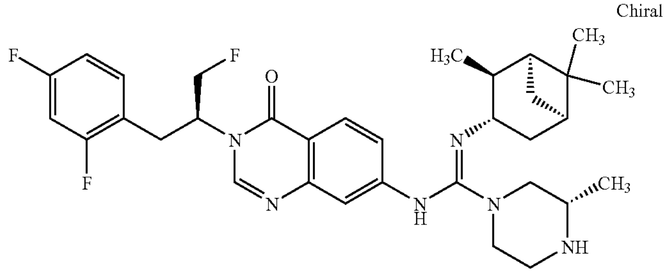 | (3S)-N-{3-[(1S)-2-(2,4-difluorophenyl)-1-(fluoromethyl)ethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 595.7 |
| 41 | 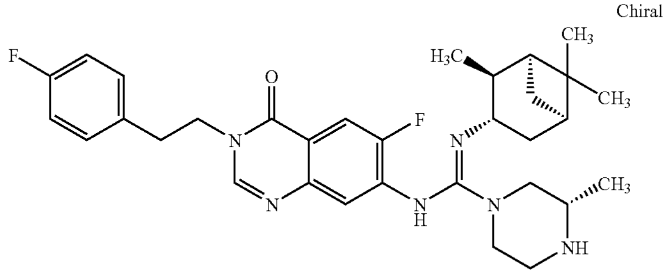 | (3S)-N-{6-fluoro-3-[2-(4-fluorophenyl)ethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 563.7 |

TABLE-continued of Examples 4-66

| No. | Structure | Name | MH+ |
|---|---|---|---|
| 42 | Chiral | (3R,5S)-N-{6-fluoro-3-[2-(4-fluorophenyl)ethyl]-4-oxo-3,4-dihydroquinazolin-7-yl}-3,5-dimethyl-N'-[(1S,2S,5R)-2,6,6-trimethylbicyclo[3.1.1]hept-3-yl]piperazine-1-carboximidamide | 577.7 |
| 43 | Chiral | (3S)-N-(3-{(1R)-2-[2-fluoro-4-(methyloxy)phenyl]-1-methylethyl}-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 589.8 |
| 44 | Chiral | (3S)-N-(6-fluoro-3-{2-[2-fluoro-4-(methyloxy)phenyl]ethyl}-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 593.7 |
| 45 | Chiral | (3R,5S)-N-(6-fluoro-3-{2-[2-fluoro-4-(methyloxy)phenyl]ethyl}-4-oxo-3,4-dihydroquinazolin-7-yl)-3-dimethyl-N'-[(1S,2S,3S,5R)-2,6,6-trimethylbicyclo[3.1.1]hept-3-yl]piperazine-1-carboximidamide | 607.8 |
| 46 | Chiral | (3S)-N-{3-[2-(2-fluoro-4-methylphenyl)ethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 559.7 |

TABLE-continued of Examples 4-66

| No. | Structure | Name | MH+ |
|---|---|---|---|
| 47 | 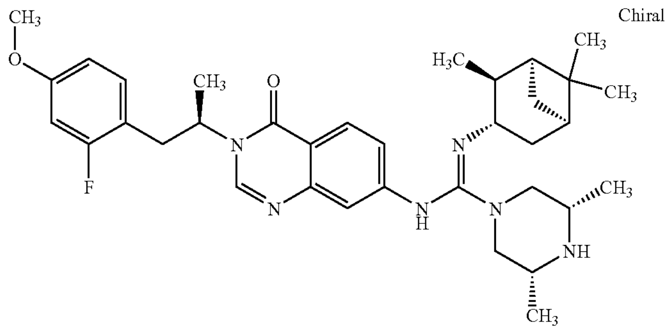 | (3R,5S)-N-(3-{(1R)-2-[2-fluoro-4-(methyloxy)phenyl]-1-methylethyl}-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 603.8 |
| 48 | 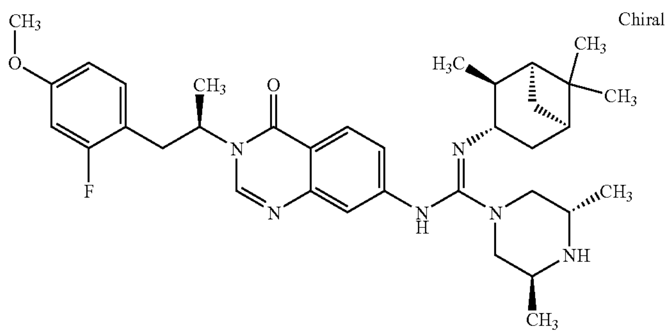 | (3S,5S)-N-(3-{(1R)-2-[2-fluoro-4-(methyloxy)phenyl]-1-methylethyl}-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 603.8 |
| 49 | 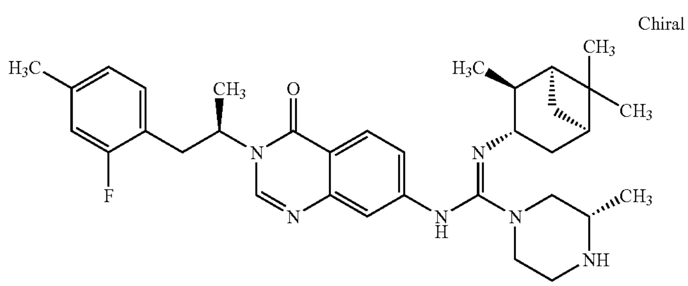 | (3S)-N-{3-[(1R)-2-(2-fluoro-4-methylphenyl)-1-methylethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 573.8 |
| 50 | 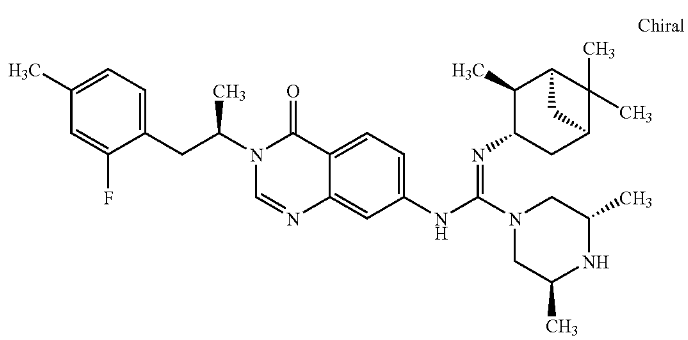 | (3S,5S)-N-{3-[(1R)-2-(2-fluoro-4-methylphenyl)-1-methylethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 587.8 |

TABLE-continued of Examples 4-66

| No. | Structure | Name | MH+ |
|---|---|---|---|
| 51 | 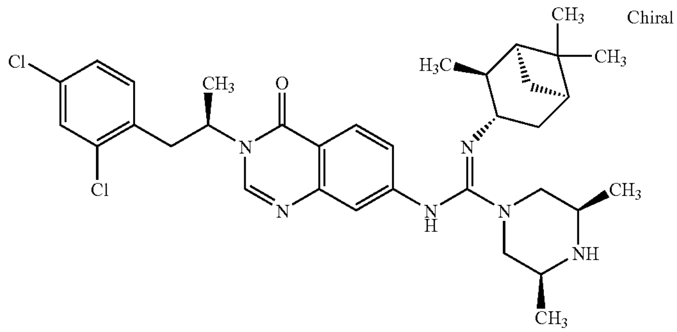 | (3R,5S)-N-{3-[(1R)-2-(2,4-dichlorophenyl)-1-methylethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 624.7 |
| 52 | 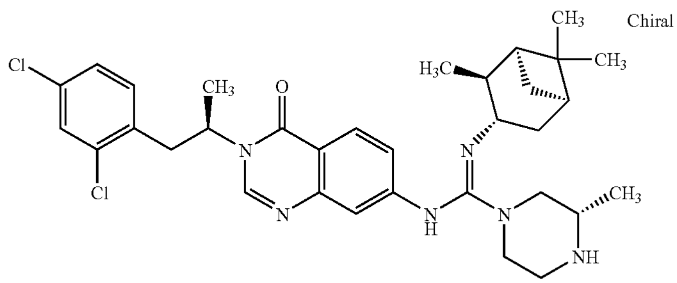 | (3S)-N-{3-[(1R)-2-(2,4-dichlorophenyl)-1-methylethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 610.6 |
| 53 | 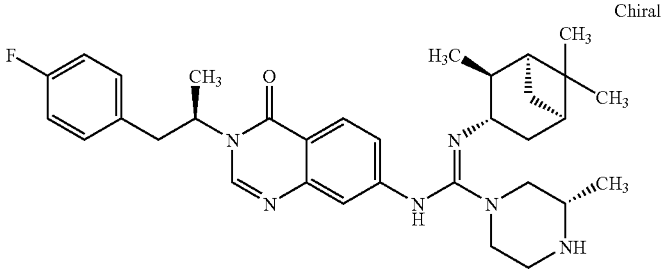 | (3S)-N-{3-[(1R)-2-(4-fluorophenyl)-1-methylethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 559.7 |
| 54 | 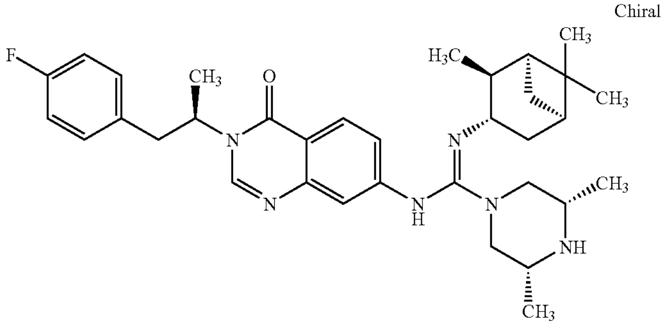 | (3R,5S)-N-{3-[(1R)-2-(4-fluorophenyl)-1-methylethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 573.8 |
| 55 | 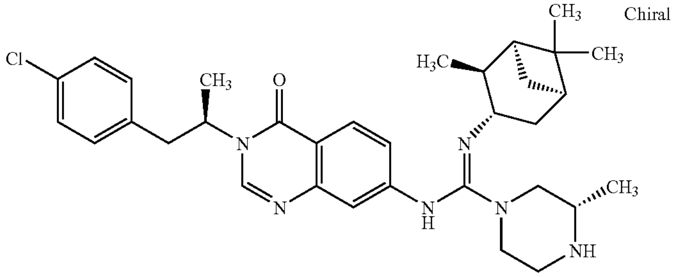 | (3S)-N-{3-[(1R)-2-(4-chlorophenyl)-1-methylethyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 576.2 |

TABLE-continued of Examples 4-66

| No. | Structure | Name | MH+ |
|---|---|---|---|
| 56 | 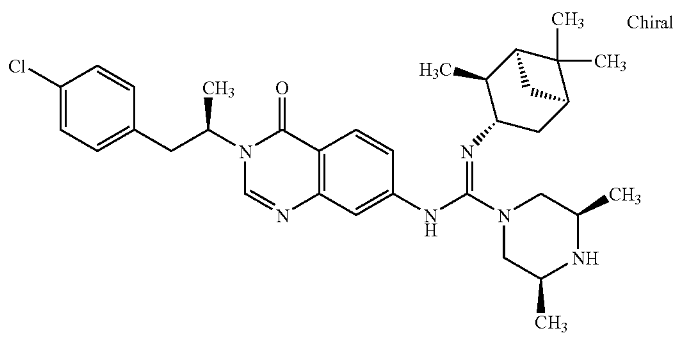 | (3R,5S)-N-{3-[(1R)-2-(4-chlorophenyl)-1-methylethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 590.2 |
| 57 | 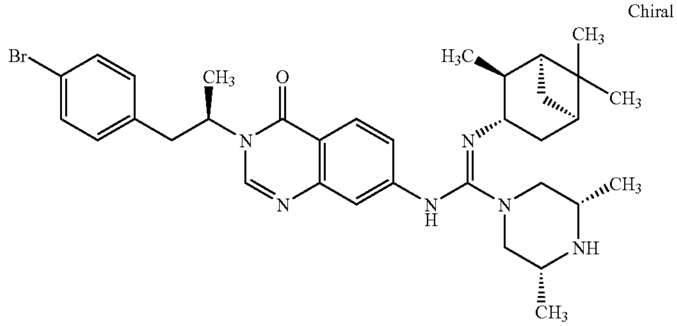 | (3R,5S)-N-{3-[(1R)-2-(4-bromophenyl)-1-methylethyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 634.7 |
| 58 | 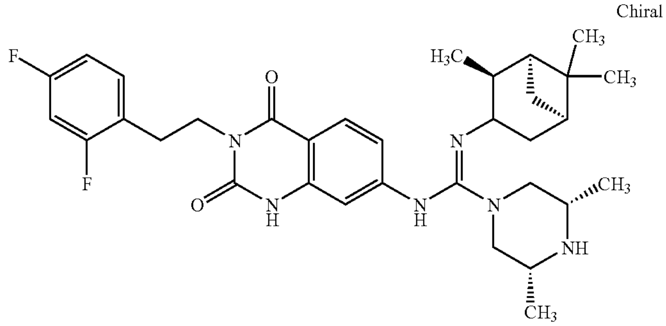 | (3R,5S)-N-{3-[2-(2,4-difluorophenyl)ethyl]-2,4-dioxo-1,2,3,4-tetrahydroquinazolin-7-yl}-3,5-dimethyl-N'-[(1S,2S,5R)-2,6,6-trimethylbicyclo[3.1.1]hept-3-yl]piperazine-1-carboximidamide | 593.7 |
| 59 | 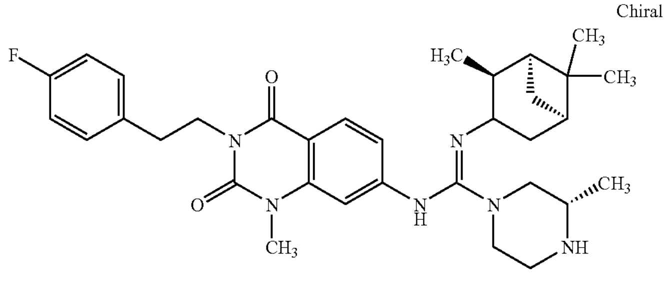 | (3S)-N-{3-[2-(4-fluorophenyl)ethyl]-1-methyl-2,4-dioxo-1,2,3,4-tetrahydroquinazolin-7-yl}-3-methyl-N'-[(1S,2S,5R)-2,6,6-trimethylbicyclo[3.1.1]hept-3-yl]piperazine-1-carboximidamide | 575.7 |

TABLE-continued of Examples 4-66

| No. | Structure | Name | MH+ |
|---|---|---|---|
| 60 | 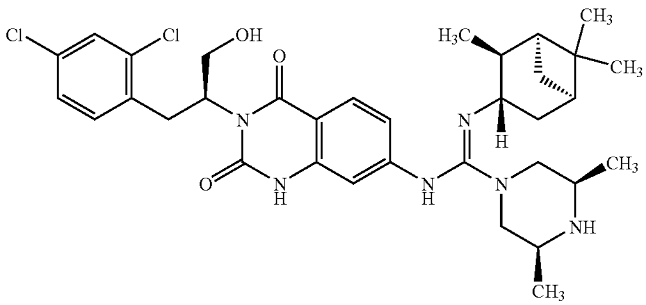 | (3R,5S)-N-{3-[(1S)-2-(2,4-dichlorophenyl)-1-(hydroxymethyl)ethyl]-2,4-dioxo-1,2,3,4-tetrahydroquinazolin-7-yl}-3,5-dimethyl-N'-[(1S,2S,3S,5R)-2,6,6-trimethylbicyclo[3.1.1]hept-3-yl]piperazine-1-carboximidamide | 656.7 |
| 61 | Chiral | (3S)-N-(2-hydroxy-3-methyl-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 453.6 |
| 62 | Chiral | (3S)-N-[3-(2-{4-[(4-fluorophenyl)carbonyl]piperidin-1-yl}ethyl)-2,4-dioxo-1,2,3,4-tetrahydroquinazolin-7-yl]-3-methyl-N'-[(1S,2S,3S,5R)-2,6,6-trimethylbicyclo[3.1.1]hept-3-yl]piperazine-1-carboximidamide | 672.9 |
| 63 | Chiral | (3S)-N-{3-[2-(2,4-dichlorophenyl)ethyl]-2,4-dioxo-1,2,3,4-tetrahydroquinazolin-7-yl}-3-methyl-N'-[(1S,2S,3S,5R)-2,6,6-trimethylbicyclo[3.1.1]hept-3-yl]piperazine-1-carboximidamide | 612.6 |
| 64 | Chiral | (3S)-N-(3-{2-[2-fluoro-4-(methyloxy)phenyl]ethyl}-2,4-dioxo-1,2,3,4-tetrahydroquinazolin-7-yl)-3-methyl-N'-[(1S,2S,3S,5R)-2,6,6-trimethylbicyclo[3.1.1]hept-3-yl]piperazine-1-carboximidamide | 591.7 |

TABLE-continued of Examples 4-66

| No. | Structure | Name | MH+ |
|---|---|---|---|
| 65 | 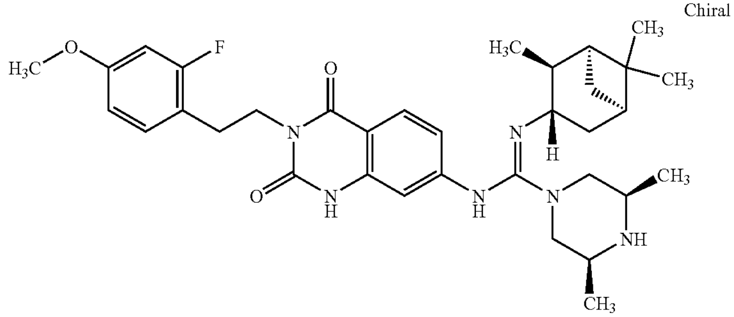 | (3R,5S)-N-(3-{2-[2-fluoro-4-(methyloxy)phenyl]ethyl}-2,4-dioxo-1,2,3,4-tetrahydroquinazolin-7-yl)-3,5-dimethyl-N'-[(1S,2S,3S,5R)-2,6,6-trimethylbicyclo[3.1.1]hept-3-yl]piperazine-1-carboximidamide | 605.8 |
| 66 | 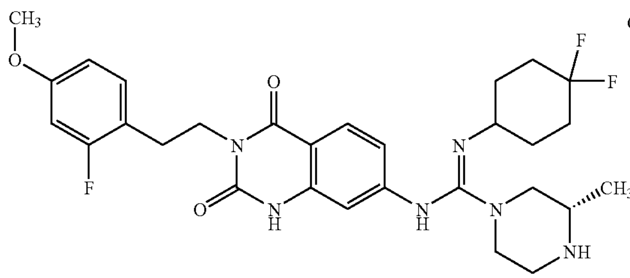 | (3S)-N'-(4,4-difluorocyclohexyl)-N-(3-{2-[2-fluoro-4-(methyloxy)phenyl]ethyl}-2,4-dioxo-1,2,3,4-tetrahydroquinazolin-7-yl)-3-methylpiperazine-1-carboximidamide | 573.6 |

The compounds in the following table were prepared using the methodology described in the previous Examples and Methods. The starting materials used in the syntheses are recognizable to one of skill in the art and are commercially available or may be prepared using known methods.

TABLE of Examples 67-101

| No. | Structure | Name | MH+ |
|---|---|---|---|
| 67 | 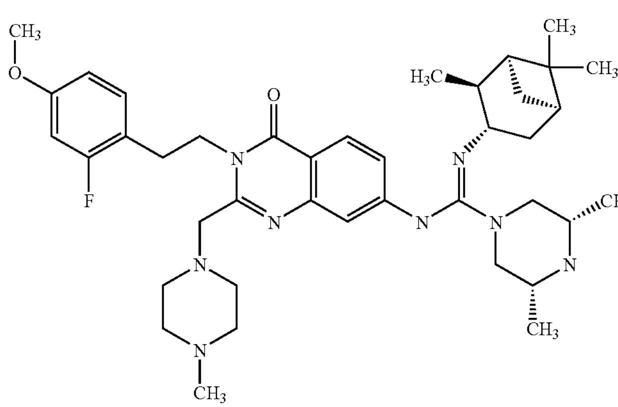 | (3R,5S)-N-{3-{2-[2-fluoro-4-(methyloxy)phenyl]ethyl}-2-[(4-methylpiperazin-1-yl)methyl]-4-oxo-3,4-dihydroquinazolin-7-yl}-3,5-dimethyl-N'-[(1S,2S,3S,5R)-2,6,6-trimethylbicyclo[3.1.1]hept-3-yl]piperazine-1-carboximidamide | 701.9 |

TABLE-continued of Examples 67-101

| No. | Structure | Name | MH+ |
|---|---|---|---|
| 68 | Chiral | (3S)-N-{3-{2-[2-fluoro-4-(methyloxy)phenyl]ethyl}-2-[(methyloxy)methyl]-4-oxo-3,4-dihydroquinazolin-7-yl}-3-methyl-N'-[(1S,2S,5R)-2,6,6-trimethylbicyclo[3.1.1]hept-3-yl]piperazine-1-carboximidamide | 619.8 |
| 69 | Chiral | (3S)-N-{3-[2-(4-fluorophenyl)ethyl]-2-[(4-methylpiperazin-1-yl)methyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 657.9 |
| 70 | Chiral | (3S)-N-[3-[2-(4-fluorophenyl)ethyl]-2-(1H-imidazol-1-ylmethyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 625.8 |
| 71 | Chiral | (3S)-N-{3-{2-[2-fluoro-4-(methyloxy)phenyl]ethyl}-2-[imino(4-methylpiperazin-1-yl)methyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 700.9 |

TABLE-continued of Examples 67-101

| No. | Structure | Name | MH+ |
|---|---|---|---|
| 72 | 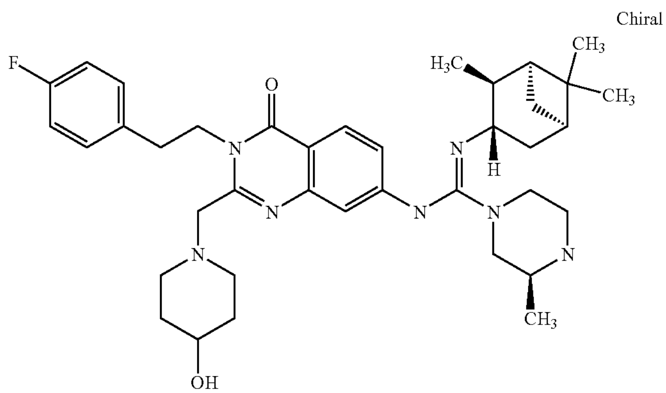 | (3S)-N-{3-[2-(4-fluorophenyl)ethyl]-2-[(4-hydroxypiperidin-1-yl)methyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 658.9 |
| 73 | 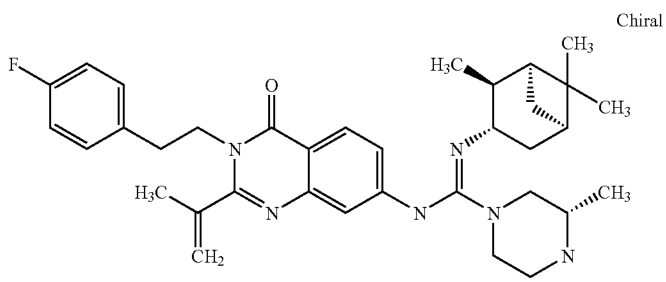 | (3S)-N-[3-[2-(4-fluorophenyl)ethyl]-2-(1-methylethenyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 585.8 |
| 74 | 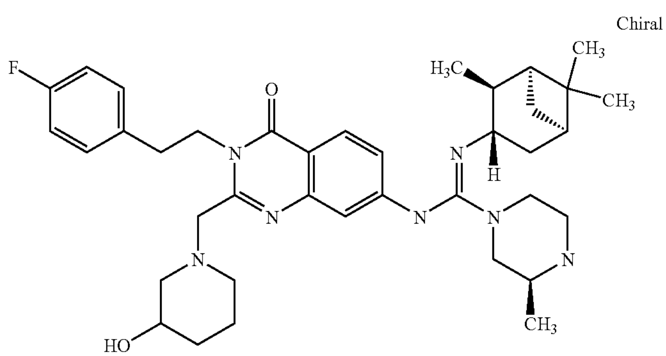 | (3S)-N-{3-[2-(4-fluorophenyl)ethyl]-2-[(3-hydroxypiperidin-1-yl)methyl]-4-oxo-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 658.9 |
| 75 | 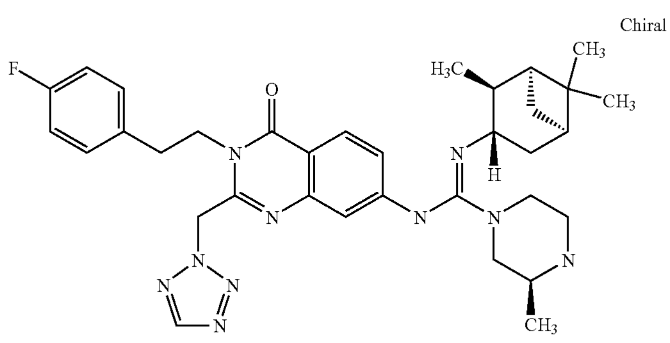 | (3S)-N-[3-[2-(4-fluorophenyl)ethyl]-4-oxo-2-(2H-tetrazol-2-ylmethyl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 627.8 |

TABLE-continued of Examples 67-101

| No. | Structure | Name | MH+ |
|---|---|---|---|
| 76 | 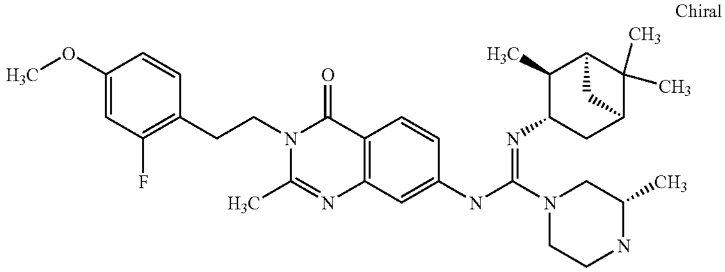 | Chiral (3S)-N-(3-{2-[2-fluoro-4-(methyloxy)phenyl]ethyl}-2-methyl-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 589.8 |
| 77 | 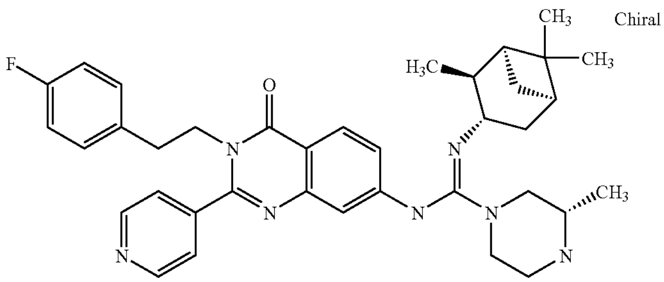 | Chiral (3S)-N-{3-[2-(4-fluorophenyl)ethyl]-4-oxo-2-pyridin-4-yl-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 622.8 |
| 78 | 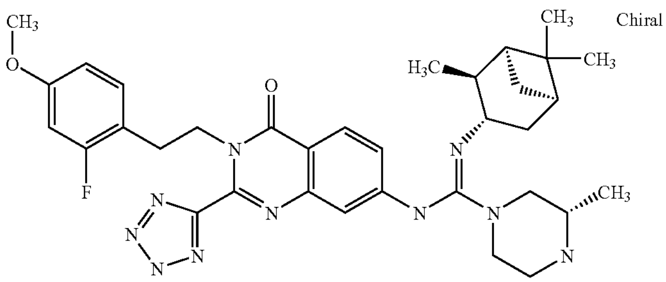 | Chiral (3S)-N-[3-{2-[2-fluoro-4-(methyloxy)phenyl]ethyl}-4-oxo-2-(2H-tetrazol-5-yl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 643.8 |
| 79 | 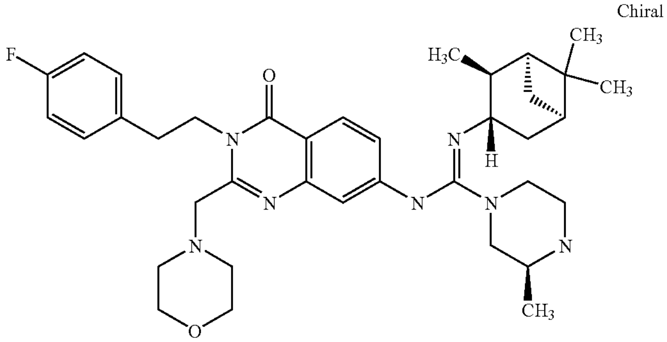 | Chiral (3S)-N-[3-[2-(4-fluorophenyl)ethyl]-2-(morpholin-4-ylmethyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 644.8 |
| 80 | 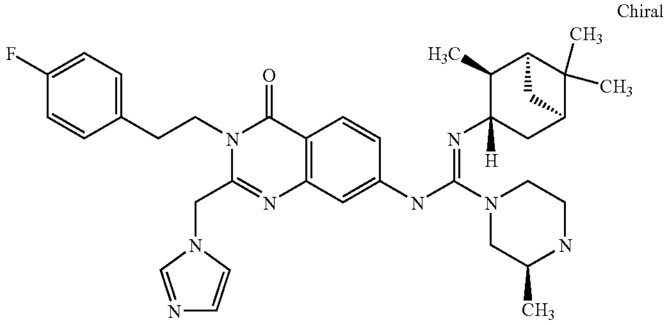 | Chiral (3S)-N-[3-[2-(4-fluorophenyl)ethyl]-2-(1H-imidazol-1-ylmethyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 625.8 |

TABLE-continued of Examples 67-101

| No. | Structure | Name | MH+ |
|---|---|---|---|
| 81 | Chiral | (3S)-N-[3-[2-(4-fluorophenyl)ethyl]-4-oxo-2-(1H-tetrazol-1-ylmethyl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 627.8 |
| 82 | Chiral | (3S)-N-{3-[2-(4-fluorophenyl)ethyl]-4-oxo-2-phenyl-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 621.8 |
| 83 | Chiral | (3S)-N-[3-[2-(4-fluorophenyl)ethyl]-2-(2-methylpropyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 601.8 |
| 84 | Chiral | (3S)-N-(3-[2-(4-fluorophenyl)ethyl]-2-{2-[4-(methyloxy)phenyl]ethyl}-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 679.9 |
| 85 | Chiral | (3S)-N-[3-[2-(4-fluorophenyl)ethyl]-2-(4-methylcyclohexyl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 641.9 |

TABLE-continued of Examples 67-101

| No. | Structure | Name | MH+ |
|---|---|---|---|
| 86 | 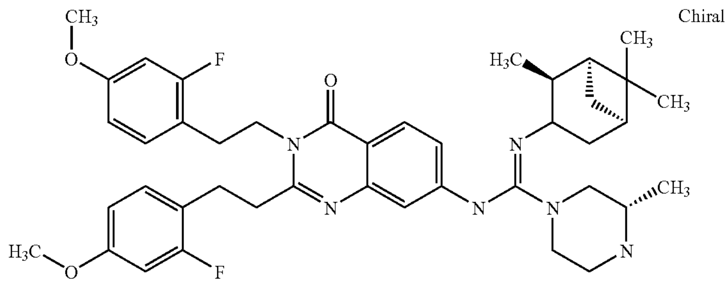 | (3S)-N-(2,3-bis{2-[2-fluoro-4-(methyloxy) phenyl]ethyl}-4-oxo-3,4-dihydroquinazolin-7-yl)-3-methyl-N'-[(1S,2S,5R)-2,6,6-trimethylbicyclo[3.1.1] hept-3-yl]piperazine-1-carboximidamide | 727.9 |
| 87 | 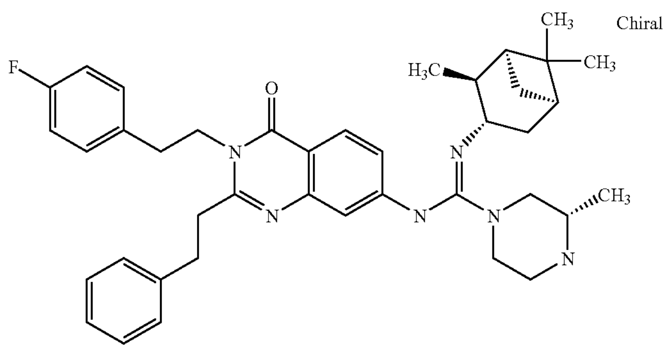 | (3S)-N-[3-[2-(4-fluorophenyl)ethyl]-4-oxo-2-(2-phenylethyl)-3,4-dihydroquinazolin-7-yl]-3-methyl-N'-[(1S,2S,3S,5R)-2,6,6-trimethylbicyclo [3.1.1]hept-3-yl]piperazine-1-carboximidamide | 649.9 |
| 88 | 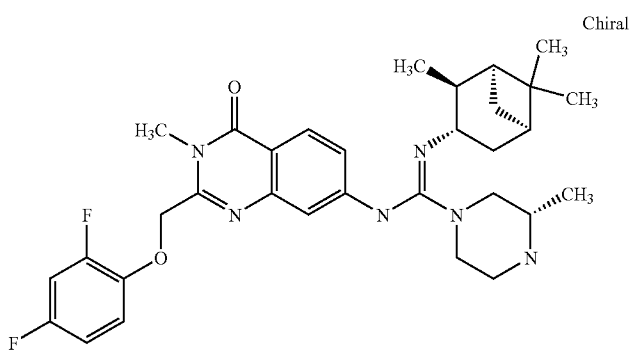 | (3S)-N-(2-{[(2,4-difluorophenyl)oxy]methyl{-3-methyl-4-oxo-3,4-dihydroquinazolin-7-yl)-3-methyl-N'-[(1S,2S,5R)-2,6,6-trimethylbicyclo[3.1.1] hept-3-yl]piperazine-1-carboximidamide | 580.7 |
| 89 | 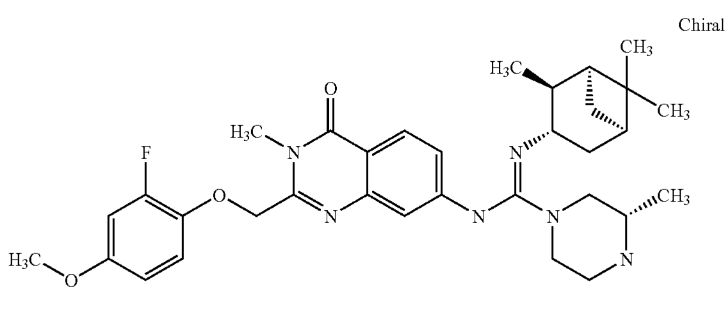 | (3S)-N-[2-({[2-fluoro-4-(methyloxy) phenyl]oxy}methyl)-3-methyl-4-oxo-3,4-dihydroquinazolin-7-yl]-3-methyl-N'-[(1S,2S,3S,5R)-2,6,6-trimethylbicyclo [3.1.1]hept-3-yl]piperazine-1-carboximidamide | 592.7 |

TABLE-continued of Examples 67-101

| No. | Structure | Name | MH+ |
|---|---|---|---|
| 90 | Chiral | (3S)-N-(2-{2-[2-fluoro-4-(methyloxy)phenyl]ethyl}-3-methyl-4-oxo-3,4-dihydroquinazolin-7-yl)-3-methyl-N'-[(1S,2S,5R)-2,6,6-trimethylbicyclo[3.1.1]hept-3-yl]piperazine-1-carboximidamide | 590.8 |
| 91 | Chiral | (3S)-3-methyl-N-[3-methyl-4-oxo-2-(1H-tetrazol-1-ylmethyl)-3,4-dihydroquinazolin-7-yl]-N'-[(1S,2S,5R)-2,6,6-trimethylbicyclo[3.1.1]hept-3-yl]piperazine-1-carboximidamide | 520.7 |
| 92 | Chiral | (3S)-N-(2-{[(4-fluorophenyl)oxy]methyl}-3-methyl-4-oxo-3,4-dihydroquinazolin-7-yl)-3-methyl-N'-[(1S,2S,5R)-2,6,6-trimethylbicyclo[3.1.1]hept-3-yl]piperazine-1-carboximidamide | 562.7 |
| 93 | Chiral | (3S)-N-(2-{[(4-chlorophenyl)oxy]methyl}-3-methyl-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 579.2 |

TABLE-continued of Examples 67-101

| No. | Structure | Name | MH+ |
|---|---|---|---|
| 94 | 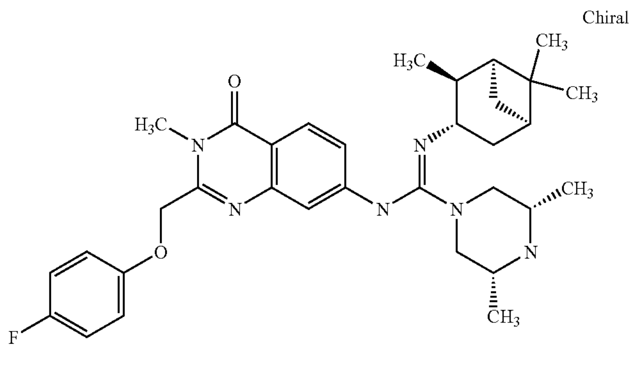 | (3R,5S)-N-(2-{[(4-fluorophenyl)oxy]methyl}-3-methyl-4-oxo-3,4-dihydroquinazolin-7-yl)-3,5-dimethyl-N'-[(1S,2S,3S,5R)-2,6,6-trimethylbicyclo[3.1.1]hept-3-yl]piperazine-1-carboximidamide | 576.7 |
| 95 | 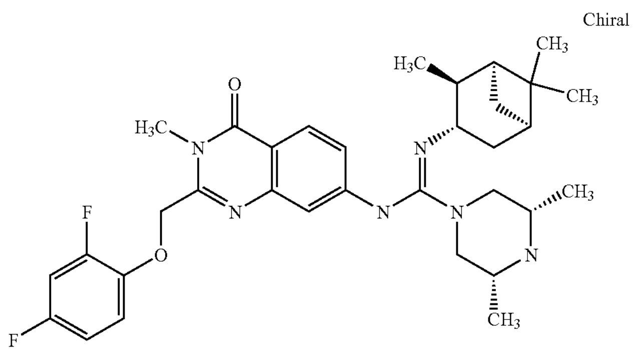 | (3R,5S)-N-(2-{[(2,4-difluorophenyl)oxy]methyl}-3-methyl-4-oxo-3,4-dihydroquinazolin-7-yl)-3,5-dimethyl-N'-[(1S,2S,5R)-2,6,6-trimethylbicyclo[3.1.1]hept-3-yl]piperazine-1-carboximidamide | 597.7 |
| 96 | 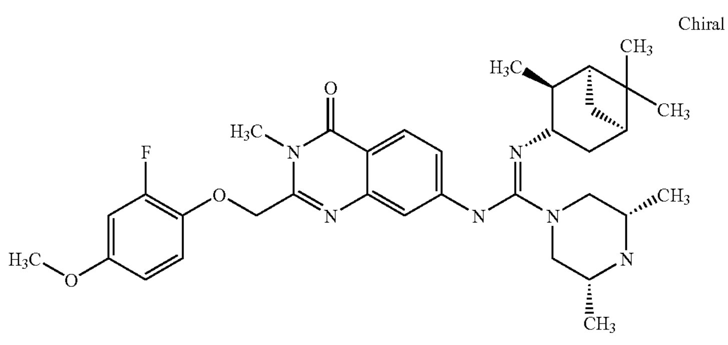 | (3R,5S)-N-[2-({[2-fluoro-4-methyloxy)phenyl]oxy}methyl)-3-methyl-4-oxo-3,4-dihydroquinazolin-7-yl]-3,5-dimethyl-N'-[(1S,2S,3S,5R)-2,6,6-trimethylbicyclo[3.1.1]hept-3-yl]piperazine-1-carboximidamide | 606.8 |
| 97 | 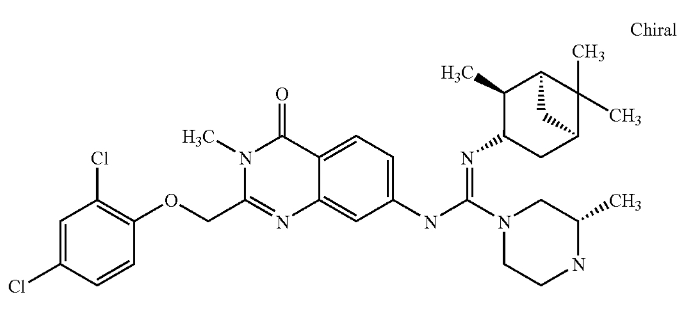 | (3S)-N-(2-{[(2,4-dichlorophenyl)oxy]methyl}-3-methyl-4-oxo-3,4-dihydroquinazolin-7-yl)-3-methyl-N'-[(1S,2S,3S,5R)-2,6,6-trimethylbicyclo[3.1.1]hept-3-yl]piperazine-1-carboximidamide | 613.6 |

TABLE-continued of Examples 67-101

| No. | Structure | Name | MH+ |
|---|---|---|---|
| 98 | Chiral | (3R,5S)-N-(2-{[(2,4-dichlorophenyl)oxy]methyl}-3-methyl-4-oxo-3,4-dihydroquinazolin-7-yl)-3-methyl-N'-[(1S,2S,5R)-2,6,6-trimethylbicyclo[3.1.1]hept-3-yl]piperazine-1-carboximidamide | 627.6 |
| 99 | Chiral | (3S)-N-[3-{2-[2-fluoro-4-(methyloxy)phenyl]ethyl}-2-(4-methylpiperazin-1-yl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 673.9 |
| 100 | Chiral | (3S)-N-[2-({[2-fluoro-4-(methyloxy)phenyl]oxy}methyl)-4-oxo-3-(phenylmethyl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 667.8 |
| 101 | Chiral | (3S)-3-methyl-N-{2-[(4-methylpiperazin-1-yl)methyl]-4-oxo-3-prop-2-enyl-3,4-dihydroquinazolin-7-yl}-N'-[(1S,2S,3S,5R)-2,6,6-trimethylbicyclo[3.1.1]hept-3-yl]piperazine-1-carboximidamide | 575.8 |

The compounds in the following table were prepared using the methodology described in the previous Examples and Methods. The starting materials used in the syntheses are recognizable to one of skill in the art and are commercially available or may be prepared using known methods.

TABLE of Examples 102-112

| No. | Structure | Name | MH+ |
|---|---|---|---|
| 102 | Chiral | (3R,5S)-N-(3-{2-[2-fluoro-4-(methyloxy)phenyl]ethyl}-4-oxo-3,4-dihydro-1,2,3-benzotriazin-7-yl)-3,5-dimethyl-N'-[(1S,2S,3S,5R)-2,6,6-trimethylbicyclo[3.1.1]hept-3-yl]piperazine-1-carboximidamide | 590.8 |
| 103 | Chiral | (3R,5S)-N-(2-{2-[2-fluoro-4-(methyloxy)phenyl]ethyl}-1-oxo-1,2-dihydroisoquinolin-6-yl)-3,5-dimethyl-N'-[(1S,2S,3S,5R)-2,6,6-trimethylbicyclo[3.1.1]hept-3-yl]piperazine-1-carboximidamide | 588.8 |
| 104 | 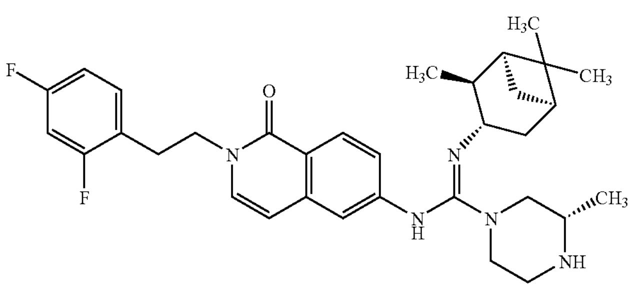 | (3S)-N-{2-[2-(2,4-difluorophenyl)ethyl]-1-oxo-1,2-dihydroisoquinolin-6-yl}-3-methyl-N'-[(1S,2S,3S,5R)-2,6,6-trimethylbicyclo[3.1.1]hept-3-yl]piperazine-1-carboximidamide | 562.7 |
| 105 | 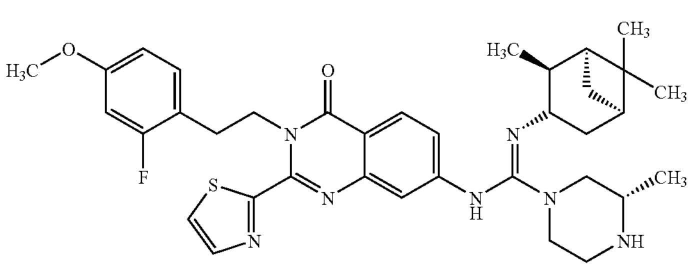 | (3S)-N-[3-{2-[2-fluoro-4-(methyloxy)phenyl]ethyl}-4-oxo-2-(1,3-thiazol-2-yl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 658.9 |

TABLE-continued of Examples 102-112

| No. | Structure | | Name | MH+ |
|---|---|---|---|---|
| 106 | 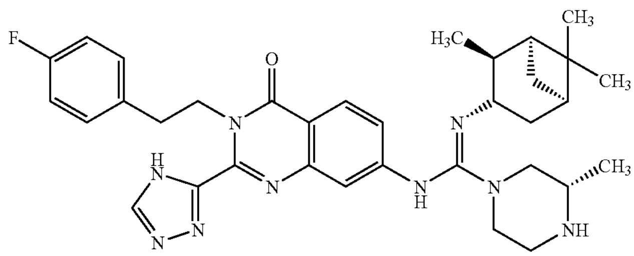 | | (3S)-N-[3-[2-(4-fluorophenyl)ethyl]-4-oxo-2-(4H-1,2,4-triazol-3-yl)-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 612.8 |
| 107 | 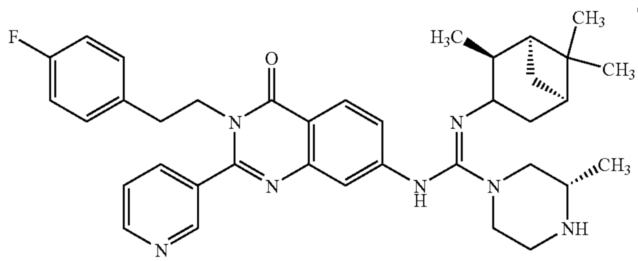 | Chiral | (3S)-N-{3-[2-(4-fluorophenyl)ethyl]-4-oxo-2-pyridin-3-yl-3,4-dihydroquinazolin-7-yl}-3-methyl-N'-[(1S,2S,5R)-2,6,6-trimethylbicyclo[3.1.1]hept-3-yl]piperazine-1-carboximidamide | 622.8 |
| 108 | 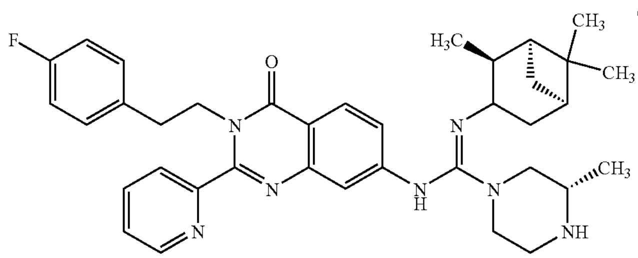 | Chiral | (3S)-N-{3-[2-(4-fluorophenyl)ethyl]-4-oxo-2-pyridin-3-yl-3,4-dihydroquinazolin-7-yl}-3-methyl-N'-[(1S,2S,5R)-2,6,6-trimethylbicyclo[3.1.1]hept-3-yl]piperazine-1-carboximidamide | 622.8 |
| 109 | 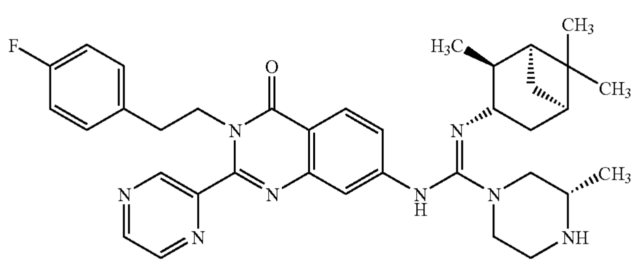 | Chiral | (3S)-N-{3-[2-(4-fluorophenyl)ethyl]-4-oxo-2-pyrazin-3-yl-3,4-dihydroquinazolin-7-yl}-3-methyl-N'-[(1S,2S,3S,5R)-2,6,6-trimethylbicyclo[3.1.1]hept-3-yl]piperazine-1-carboximidamide | 623.8 |
| 110 | 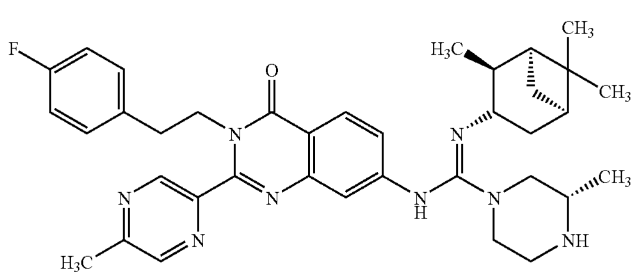 | Chiral | (3S)-N-[3-[2-(4-fluorophenyl)ethyl]-2-(5-methylpyrazin-2-yl)-4-oxo-3,4-dihydroquinazolin-7-yl]-3-methyl-N'-[(1S,2S,3S,5R)-2,6,6-trimethylbicyclo[3.1.1]hept-3-yl]piperazine-1-carboximidamide | 637.8 |

TABLE-continued of Examples 102-112

| No. | Structure | Name | MH+ |
|---|---|---|---|
| 111 | *(structure shown, Chiral)* | (3R)-3-(fluoromethyl)-N-(3-{2-[2-fluoro-4-(methyloxy)phenyl]ethyl}-4-oxo-3,4-dihydroquinazolin-7-yl)-N'-[(1S,2S,3S,5R)-2,6,6-trimethylbicyclo[3.1.1]hept-3-yl]piperazine-1-carboximidamide | 593.7 |
| 112 | *(structure shown, Chiral)* | (3R)-N-(3-{2-[2-fluoro-4-(methyloxy)phenyl]ethyl}-4-oxo-3,4-dihydroquinazolin-7-yl)-3-(trifluoromethyl)-N'-[(1S,2S,3S,5R)-2,6,6-trimethylbicyclo[3.1.1]hept-3-yl]piperazine-1-carboximidamide | 629.7 |

$EC_{50}$ values of test compounds were determined by treating cells expressing MC4-R with test compound and lysing the cells and measuring intercellular cAMP concentration with an Amersham-Pharmacia RPA-559 cAMP Scintillation Proximity Assay (SPA) kit. The compounds described above were synthesized and tested according to this assay. Each of the named compounds of Examples 1-104 exhibited $-\log EC_{50}$ values above about 3. Examples 105-112 will be found to exhibit $-\log EC_{50}$ values above about 3. For this reason, each of the exemplary compounds are individually preferred and are preferred as a group. Furthermore, the groups corresponding to $R^1$ through $R^9$, $R^{1'}$ through $R^{4'}$, L, Y, and W for each of the named compounds of Examples 1-112 are also preferred. Nomenclature for these compounds was provided using ACD Name version 5.07 software (Nov. 14, 2001) available from Advanced Chemistry Development, Inc and ChemInnovation NamExpert+Nomenclator™ brand software available from ChemInnovation Software, Inc. Some of the starting materials were named using standard IUPAC nomenclature. Example compounds 1-112 are illustrative and should not be construed as limiting of the instant invention.

In Vivo Studies of MC4-R Agonists on Energy Intake, Body Weight, Hyperinsulinemia, and Glucose Levels In vivo studies are conducted to observe the effect of MCR-4 agonists on energy intake, body weight, hyperinsulinemia, and glucose levels. All studies are conducted with male 9-10 week old ob/ob mice which display early onset of obesity, insulin resistance and diabetes due to leptin deficiency. Mice are acclimated in the facility for 1 week before studies and are caged individually. Vehicle-treated (control) and drug treated mice studies are always run in parallel. In multi-day studies, mice (8-15 per group) are monitored for baseline body weight, fasting levels of glucose, insulin, blood lipids and energy expenditure and then injected twice daily (9 a.m. and 5 p.m.) with 3 mg/kg of a MC4-R agonist of the present invention for 4 weeks. Body weight as well as food and water intake are monitored daily. Animals are fasted overnight for measurements of fasting levels of glucose, insulin, and lipids once a week until the end of the study. Energy expenditure (resting metabolic rate, i.e., $O_2$ consumption and $CO_2$ production) are monitored in air tight chambers at the end of the study on fed animals. $O_2$ consumption and $CO_2$ production are measured using Oxymax systems (Columbus Instruments). Oral glucose tolerance test (OGTT—a routine test for diabetes and glucose intolerance) is performed on overnight fasted mice at the end of the study. Blood glucose and oral glucose tolerance are measured using a glucose monitor (Onetouch sold by Lifescan). Free fatty acids are measured using an non-esterified free fatty acids enzymatic assay (Waco Chemicals). Serum Insulin levels are measured by immunoassay (Alpco).

Results

The effect of the compounds of the present invention on food intake is determined by measuring grams/mouse/day throughout a 4 week study. Food is monitored every morning. Cumulative food intake represents the total amount of grams the mice consume during the study. A significant reduction in food intake is demonstrated in those mice treated IP with the compounds of the present invention.

The effect of the compounds of the present invention on body weight is determined by measuring grams/mouse throughout a 4 week study. Mice are weighed every morning. A significant body weight reduction is demonstrated in those mice treated IP with the compounds of the present invention.

The effect of the compounds of the present invention on blood glucose levels is determined by measuring blood glucose levels as represented as mg of glucose/dL of blood. Mice are fasted overnight and glucose levels are measured the following morning. Vehicle treated mice show an increase in blood glucose consistent with the rapid progression of diabetes in this mouse strain whereas, diabetes is slowed down considerably in drug treated mice. A significant reduction in fasting glucose levels is demonstrated in those mice treated IP with the compounds of this invention.

The effect of the compounds of the present invention on glucose levels during oral glucose tolerance test (OGTT) is determined by measuring blood glucose in overnight fasted mice. Blood glucose is represented as mg of glucose/dL of blood. Glucose levels are measured the following morning. Orally administered glucose quickly elevates blood glucose, similar to a meal, and the response to this exogenous glucose gives a measure of how well the body regulated glucose homeostasis. Vehicle treated mice show an elevated response to glucose consistent with their diabetic state, whereas drug treated mice show a very much improved glucose disposal.

The effect of the compounds of the present invention on free fatty acid (FFA) levels is determined by measuring mmoles of FFA/L of serum. Mice are fasted overnight and free fatty acid levels are measured the following morning. Vehicle treated mice show elevated levels of FFA throughout the study consistent with their obese state, whereas the drug treated mice diabetes show a dramatic decrease.

The effect of the compounds of the present invention on serum insulin levels is determined by measuring serum insulin levels one hour after single IP dosing of 1 and 3 mg/kg in overnight fasted ob/ob mice. Serum insulin levels are represented as ng of insulin/mL of serum. Drug treated mice show a dose dependent decrease relative to vehicle.

It is understood that the invention is not limited to the embodiments set forth herein for illustration, but embraces all such forms thereof as come within the scope of the following claims.

What is claimed is:

1. A compound of formula ID

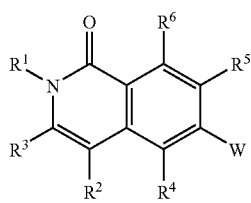

ID wherein $R^1$ is an arylalkyl group optionally substituted with one or more substituents independently selected from the group consisting of alkyl, cyano, F, Cl, Br, I, hydroxyl, alkoxy, aryloxy, ester, thiol, alkyl sulfide, aryl sulfide, sulfone, sulfonyl, sulfoxide, amine, amide, alkylamine, dialkylamine, arylamine, alkylarylamine, diarylamine, N-oxide, imide, enamine, trialkylsilyl, dialkylarylsilyl, alkyldiarylsilyl, and triarylsilyl;

$R^2$ and $R^3$ are each H;
$R^4$, $R^5$, and $R^6$ are each H;
W is a group of formula IIA or IIB;

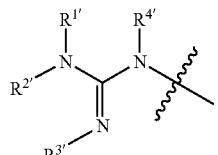

IIA

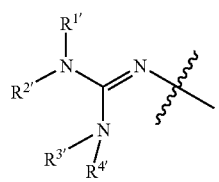

IIB $R^{1'}$ and $R^{2'}$, together with the nitrogen to which they are bound, form a piperazine optionally substituted with one or more substituents independently selected from the group consisting of F, Cl, Br, I, alkyl, cyano, hydroxyl, alkoxy, aryloxy, ester, thiol, alkyl sulfide, aryl sulfide, sulfone, sulfonyl, sulfoxide, amine, amide, alkylamine, dialkylamine, arylamine, alkylarylamine, diarylamine, N-oxide, imide, enamine, trialkylsilyl, dialkylarylsilyl, alkyldiarylsilyl, and triarylsilyl;

$R^{3'}$ is a cycloalkyl group optionally substituted with one or more substituents independently selected from the group consisting of F, Cl, Br, I, alkyl, hydroxyl, alkoxy, aryloxy, ester, thiol, alkyl sulfide, aryl sulfide, sulfone, sulfonyl, sulfoxide, amine, amide, alkylamine, dialkylamine, arylamine, alkylarylamine, diarylamine, N-oxide, imide, enamine, trialkylsilyl, dialkylarylsilyl, alkyldiarylsilyl, triarylsilyl, carbonyl, carboxyl, imine, oxime, hydrazone, and nitrile; and $R^{4'}$ is H;

or a pharmaceutically acceptable salt, stereoisomer or tautomer thereof.

2. The compound of claim 1, wherein $R^1$ is a 2,4-disubstituted phenylethyl group wherein the substituents are independently selected from the group consisting of F, Cl, Br, I, alkyl, cyano, hydroxyl, alkoxy, aryloxy, ester, thiol, alkyl sulfide, aryl sulfide, sulfone, sulfonyl, sulfoxide, amine, amide, alkylamine, dialkylamine, arylamine, alkylarylamine, diarylamine, N-oxide, imide, enamine, trialkylsilyl, dialkylarylsilyl, alkyldiarylsilyl, and triarylsilyl.

3. The compound of claim 1, wherein $R^1$ is selected from the group consisting of phenylethyl, 2,4-dichlorophenylethyl, 4-methoxyphenylethyl, 4-phenoxyphenylethyl, 4-bromophenylethyl, 4-methylphenylethyl, 4-chlorophenylethyl, 4-ethylphenylethyl, 2-methoxyphenylethyl, 2-chlorophenylethyl, 2-fluorophenylethyl, 3-methoxyphenylethyl, 3-fluorophenylethyl, 4-hydroxyphenylethyl, 3,4-dimethoxyphenylethyl, 2-chloro-4-iodophenylethyl, 2-fluoro-4-methylphenylethyl, 2-fluoro-4-chlorophenylethyl, 2-fluoro-4-bromophenylethyl, 2-fluoro-4-methoxyphenylethyl, 2,4-difluorophenylethyl, 2,4-dimethylphenylethyl, 2,4-dimethoxyphenylethyl groups, and (phenyl)(hydroxymethyl) ethyl groups.

4. The compound of claim 1 wherein $R^{3'}$ is selected from the group consisting of unsubstituted cyclohexyl, 2-alkylcyclohexyl, 2,2-dialkylcyclohexyl, 2,3-dialkylcyclohexyl, 2,4-dialkylcyclohexyl, 2,5-dialkylcyclohexyl, 2,6-dialkylcyclohexyl, 3,4-dialkylcyclohexyl, 3-alkylcyclohexyl, 4-alkylcyclohexyl, 3,3,5-trialkylcyclohexyl, 2-aminocyclohexyl, 3-aminocyclohexyl, 4-aminocyclohexyl, 2,3-diaminocyclohexyl, 2,4-diaminocyclohexyl, 3,4-diaminocyclohexyl, 2,5-diaminocyclohexyl, 2,6-diaminocyclohexyl, 2,2-diaminocyclohexyl, 2-alkoxycyclohexyl, 3-alkoxycyclohexyl, 4-alkoxycyclohexyl, 2,3-dialkoxycyclohexyl, 2,4-dialkoxycyclohexyl, 3,4-dialkoxycyclohexyl, 2,5-dialkoxycyclohexyl, 2,6-dialkoxycyclohexyl, 2,2-dialkoxycyclohexyl, 2-alkylthiocyclohexyl, 3-alkylthiocyclohexyl, 4-alkylthiocyclohexyl, 2,3-dialkylthiocyclohexyl, 2,4-dialkylthiocyclohexyl, 3,4-dialkylthiocyclohexyl, 2,5-dialkylthiocyclohexyl, 2,6-dialkylthiocyclohexyl, 2,2-dialkylthiocyclohexyl, fluorocycloalkyl, cyclopentyl, cycloheptyl, cyclooctyl, adamantyl, isocamphenyl, carenyl, 7,7-dialkylnorbornyl, bornyl, norbornyl, and decalinyl groups.

5. The compound of claim 1 wherein $R^{3'}$ is selected from the group consisting of 2-methylcyclohexyl, 2,2-dimethylcyclohexyl, 2,3-dimethylcyclohexyl, 2,4-dimethylcyclohexyl, 2,5-dimethylcyclohexyl, 2,6-dimethylcyclohexyl, 3,4-dimethylcyclohexyl, 3-methylcyclohexyl, 4-methylcyclohexyl, 3,3,5-trimethylcyclohexyl, 4-t-butylcyclohexyl, isopinocampheyl, 7,7-dimethylnorbornyl, 4-isopropylcyclohexyl, 3-methylcycloheptyl, 2-fluoro-4-methylcyclohexyl, 4-fluoro-2-methylcyclohexyl, 4,4-difluoro-2-methylcyclohexyl, 2 and fluoro(polycyclic cycloalkyl) groups.

6. The compound of claim 1 wherein $R^{1'}$ and $R^{2'}$, together with the nitrogen to which they are bound, form a piperazine optionally substituted with one or two alkyl.

7. The compound of claim 1 wherein $R^{1'}$ and $R^{2'}$, together with the nitrogen to which they are bound, form a piperazine optionally substituted with one or two methyl.

8. The compound of claim 1 which compound is selected from the group consisting of:
  (3R,5S)-N-(2-{2-[2-fluoro-4-(methyloxy)phenyl]ethyl}-1-oxo-1,2-dihydroisoquinolin-6-yl)-3,5-dimethyl-N'-[(1S,2S,3S,5R)-2,6,6-trimethylbicyclo[3.1.1]hept-3-yl]piperazine-1-carboximidamide; and
  (3S)-N-{2-[2-(2,4-difluoropheny)ethyl]-1-oxo-1,2-dihydroisoquinolin-6-yl}-3-methyl-N'-[(1S,2S,3S,5R)-2,6,6-trimethylbicyclo[3.1.1]hept-3-yl]piperazine-1-carboximidamide;
  or a pharmaceutically acceptable salt, stereoisomer or tautomer thereof.

9. A composition comprising the compound of claim 1 and a pharmaceutically acceptable carrier.

* * * * *